(12) United States Patent
Tabibiazar et al.

(10) Patent No.: US 8,965,708 B2
(45) Date of Patent: Feb. 24, 2015

(54) METHOD FOR THE TREATMENT OF ACQUIRED LYMPHEDEMA

(75) Inventors: Raymond Tabibiazar, Menlo Park, CA (US); Stanley G. Rockson, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 212 days.

(21) Appl. No.: 13/136,372

(22) Filed: Jul. 28, 2011

(65) Prior Publication Data

US 2012/0076731 A1    Mar. 29, 2012

Related U.S. Application Data

(63) Continuation-in-part of application No. 11/707,362, filed on Feb. 16, 2007, now abandoned.

(60) Provisional application No. 61/400,601, filed on Jul. 30, 2010, provisional application No. 60/774,964, filed on Feb. 17, 2006.

(51) Int. Cl.
   *G01N 33/48* (2006.01)
   *A61B 5/00* (2006.01)
   *C12Q 1/68* (2006.01)

(52) U.S. Cl.
   CPC .............. *A61B 5/411* (2013.01); *A61B 5/415* (2013.01); *A61B 5/418* (2013.01); *A61B 5/441* (2013.01); *C12Q 1/6883* (2013.01); *C12Q 2600/158* (2013.01); *C12Q 2600/106* (2013.01); *C12Q 2600/112* (2013.01); *C12Q 2600/136* (2013.01)
   USPC .......................................................... 702/19

(58) Field of Classification Search
   None
   See application file for complete search history.

(56) References Cited

U.S. PATENT DOCUMENTS

| | | | |
|---|---|---|---|
| 5,976,547 A | 11/1999 | Archer et al. | |
| 6,764,820 B2 | 7/2004 | Ferrell et al. | |
| 6,855,806 B1 | 2/2005 | Prayaga et al. | |
| 2002/0147140 A1* | 10/2002 | Rosen et al. .................... 514/12 |
| 2002/0151489 A1 | 10/2002 | Gravereaux et al. | |
| 2003/0049640 A1 | 3/2003 | Herman et al. | |
| 2006/0088532 A1 | 4/2006 | Alitalo et al. | |
| 2007/0149453 A1 | 6/2007 | Gatanaga et al. | |
| 2008/0051644 A1 | 2/2008 | Tabibiazar et al. | |

OTHER PUBLICATIONS

Badger et al. (Cochrane Database of Systematic Reviews 2004, Issue 2, pp. 1-15).*
Nieto et al. (Dig Dis Sci., 2002, 47(4):905-13).*
Szuba et al. (Vascular Medicine 1998; 3: 145-156).*
Debrah; et al., "Plasma Vascular Endothelial Growth Factor-A (VEGF-A) and VEGF-A Gene Polymorphism are Associated with Hydrocele Development in Lymphatic Filariasis", Am J Trop Med Hyg (2007), 77(4):601-608.
Nakamura; et al., "Anti-Inflammatory Pharmacotherapy with Ketoprofen Ameliorates Experimental Lymphatic Vascular Insufficiency in Mice", PLoS ONE (2009), 4(12):e8380, 7 pgs.
Wikipedia, "Lymphedema" (2010), Retrieved from the internet Jan. 24, 2012: <URL:http://en.wikipedia.org/w/index/php?title=Lymphedema&oldid=374163991>, 9 pgs.
Hirakawa et al., "Identification of vascular lineage-specific genes by transcriptional profiling of isolated blood vascular and lymphatic endothelial cells", Am J Pathol (2003), 162(2):575-586.
Leak; et al., "Proteomic analysis of lymph", Proteomics (2004), 4:753-765.
Lymboussaki; et al., "Expression of the Vascular Endothelial Growth Factor C Receptor VEGFR-3 in Lymphatic Endothelium of the Skin and in Vascular Tumors", American Journal of Pathology (1998), 153:395-403.
Nakamura; et al., "Anti-Inflammatory Pharmacotherapy with Ketoprofen Ameliorates Experimental Lymphatic Vascular Insufficiency in Mice", PLoS one (2009), 4(12):e8380, 7 pages.
Podgrabinska; et al.,"Molecular characterization of lymphatic endothelial cells", PNAS (2002), 99(25):16069-16074.
Rockson, "Lymphedema", Am J Med (2001), 110(4):288-295.
Shin; et al., "Animal models for the study of lymphatic Insufficiency", Lymphat Res Biol (2003), 1(2):159-69.
Tabibiazar; et al., "Inflammatory manifestations of experimental lymphatic insufficiency", PLoS Med. (2006), 3(7):e254, 1114-1139.
Wong; et al., "VEGF and HIF1alpha expression are increased in advanced stages of epithelial ovarian cancer", Gynecologic Oncology (2003), 91:513-517.
Karkkainen; et al., "A model for gene therapy of human hereditary lymphedema", PNAS (2001), 98(22):12677-82.

* cited by examiner

*Primary Examiner* — Pablo S Whaley
(74) *Attorney, Agent, or Firm* — Bozicevic, Field & Francis LLP; Pamela J. Sherwood

(57) ABSTRACT

The present invention identifies genes whose gene products are differentially expressed in lymphedema tissues, particularly cutaneous tissue involved in whole organ response to lymphedema. The invention provides methods for diagnosing or assessing an individual's susceptibility to lymphedema. Also provided are therapeutic methods for treating a patient or methods for prophylactically treating an individual susceptible to lymphedema. Additionally, the invention describes screening methods for identifying agents that can be administered to treat individuals that have or at risk of developing lymphedema.

5 Claims, 34 Drawing Sheets
(14 of 34 Drawing Sheet(s) Filed in Color)

A.

B.

A.

2-(3-Benzoylphenyl)propionic acid 2-arylpropionic acid core

Chemical Formula - $C_{16}H_{14}O_3$
White crystalline powder
MW 254.28
MP 94-97º C
Insoluble in water

B.

METHOD FOR THE TREATMENT OF ACQUIRED LYMPHEDEMA

CROSS REFERENCE TO RELATED APPLICATIONS

Pursuant to 35 U.S.C. §119 (e), this application claims priority to U.S. Provisional Patent Application Ser. No. 61/400,601, filed Jul. 30, 2010; and is a Continuation-in-Part of U.S. patent application Ser. No. 11/707,362, filed Feb. 16, 2007, which claims priority to U.S. Provisional Patent Application Ser. No. 60/774,964, filed Feb. 17, 2006; the disclosures of which are herein incorporated by reference.

ACKNOWLEDGMENT OF GOVERNMENT SUPPORT

This invention was made with Government support under contract HL100344 awarded by the National Institutes of Health. The Government has certain rights in this invention.

INTRODUCTION

Acquired lymphedema is a common, important and often devastating consequence of successful surgical and adjuvant therapy of breast cancer and other malignancies. It is characterized by the stagnation and accumulation of excessive interstitial fluid, with accompanying swelling of subcutaneous tissues. Lymphedema occurs with obstruction, destruction, or functional inadequacy of lymph vessels. The resultant accumulation of interstitial fluid, containing high molecular weight proteins and other cellular debris, produces a condition with a complex biology that extends far beyond edema. This condition underscores the tremendous importance of a normally functioning lymphatic system, which exists to return proteins, lipids, and water from the interstitium to the intravascular space. Forty to 50% of serum proteins are transported by this route each day. High hydrostatic pressures in arterial capillaries force proteinaceous fluid into the interstitium, resulting in increased interstitial oncotic pressure that draws in additional water. Interstitial fluid normally contributes to the nourishment of tissues. About 10% of the fluid is composed of high molecular weight proteins and their oncotically-associated water, which must ultimately enter the lymphatic capillaries. The protein rich fluid then travels as lymph through numerous filtering lymph nodes, ultimately joining the venous circulation.

In a diseased state, the lymphatic transport capacity is reduced. This causes the normal volume of interstitial fluid formation to exceed the rate of lymphatic return, resulting in the stagnation of high molecular weight proteins in the interstitium. It usually occurs after flow has been reduced by 80% or more. The result is high-protein edema, or lymphedema, with protein concentrations of 1.0-5.5 g/mL. This high oncotic pressure in the interstitium favors the accumulation of additional water.

Accumulation of interstitial fluid leads to massive dilatation of the remaining outflow tracts and valvular incompetence that causes reversal of flow from subcutaneous tissues into the dermal plexus. Lymph nodes harden and shrink, losing their normal architecture. In the interstitium, protein and fluid accumulation initiates a marked inflammatory reaction. Macrophage activity is increased, resulting in destruction of elastic fibers and production of fibrosclerotic tissue. Tissue inflammation in lymphedema may reflect either an active or passive consequence of impaired immune traffic. The result of this inflammatory reaction is a change from the initial pitting edema to the brawny nonpitting edema characteristic of lymphedema. The overlying skin can become thickened, forming thick scaly deposits of keratinized debris and may display a warty verrucosis. Cracks and furrows often develop and accommodate debris and bacteria, leading to lymphorrhea, the leakage of lymph onto the surface of the skin.

Lymphedema may be primary or secondary. Primary lymphedema can be present from birth (congenital lymphedema), may occur during puberty (lymphedema praecox), and is less often present later in life (lymphedema tarda).

Secondary lymphedema is often a result of infection, especially dermatophytosis in the foot. In older persons, it may be due to malignant disease in the pelvis or groin and may follow surgical removal of lymph nodes and/or radiotherapy. Lymphedema may be complicated by infection (lymphangitis), which is manifested by chills, high fever, toxicity, and a red, hot, swollen leg. Lymphangitic streaks may be seen in the skin, and lymph nodes in the groin are usually enlarged and tender. These features differentiate lymphangitis from acute thrombophlebitis. Lymphedema patients are also prone to recurrent attacks of soft tissue bacterial infection (cellulites or erysipelas; the accompanying signs of infection are often blunted. These recurrent infections are the source of substantial morbidity and are difficult to prevent or eradicate In the United States, the highest incidence of lymphedema is observed following breast cancer surgery, particularly among those who undergo radiation therapy following axillary lymphadenectomy. Among this population, 10-40% develop some degree of ipsilateral upper extremity lymphedema. Worldwide, 140-250 million cases of lymphedema are estimated to exist, with filariasis being the most common cause. Prevalence estimates of lymphedema, both in the United States and worldwide, are indirect, and likely reflect an undestimation of the burden of disease.

The goal of conservative therapy is to eliminate protein stagnation and restore normal lymphatic circulation. These techniques are often cumbersome, uncomfortable, inconvenient, and time-consuming. Strict compliance is essential, and treatment lasts throughout the lifetime of the individual. Current treatment often includes careful hygiene and antimicrobial therapy. Patients often wear compression garments continuously during the day. Intermittent pneumatic pump compression therapy may also be instituted on an outpatient basis or in the home.

Benzopyrenes, including flavonoids and coumarin, have becobeen advocated as adjunctive therapy in other countries but are currently not available for clinical use in the United States. These drugs bind to accumulated interstitial proteins, inducing macrophage phagocytosis and proteolysis. The resulting protein fragments theoretically pass more readily into the venous capillaries and are removed by the vascular system.

Patients with chronic lymphedema for more than 10 years have a small, but identifiable, risk of developing lymphangiosarcoma. Patients with this tumor commonly present with a reddish purple discoloration or nodule that tends to form satellite lesions. This tumor is highly aggressive, requires radical amputation of the involved extremity, and has a very poor prognosis. Other complications of lymphedema include recurrent bouts of cellulitis and/or lymphangitis, deep venous thrombosis, severe functional impairment, and necessary amputation. Complications following surgery are common and include partial wound separation, seroma, hematoma, skin necrosis, and exacerbation of foot or hand edema.

Surgical treatment is palliative, not curative, and it does not obviate the need for continued medical therapy. Moreover, it is rarely indicated as the primary treatment modality. Many surgical procedures have been advocated. None of the physiological techniques has clearly documented favorable long-term results.

Improved diagnosis and treatment of lymphedema is of great clinical and scientific interest. The present invention addresses this issue.

SUMMARY OF THE INVENTION

The present invention provides methods and compositions for the diagnosis and treatment of lymphedema. Specifically, genes are identified and described herein that are differentially expressed in lymphedema, particularly in cutaneous samples from lymphedemous regions or in the blood of lymphedema patients. The detection of the coding sequence and/or polypeptide products of these genes, as well as molecular pathways in which sets of genes and gene products are involved, provides useful methods for early detection, diagnosis, staging, and monitoring of conditions, e.g. by the analysis of blood samples, biopsy material, in vivo imaging, metabolic assays for enzymatic activities, and the like.

In some aspect of the invention, methods are provided for diagnosing lymphedema or providing a prognosis about the lymphedemous condition. In these embodiments, a lymphedema dataset, i.e. the expression profile or "expression signature" of at least one lymphedema associated gene product, is evaluated for expression levels indicative of lymphedema or of various stages of lymphedema and clinical sequelae thereof. In some embodiments, a panel of genes is evaluated. Such a panel may provide a level of discrimination not found with individual markers. In some embodiments, a cutaneous sample is assayed, e.g. a sample comprising dermal or epidermal tissue. In some embodiments, a blood sample is assayed, e.g. a whole blood sample, or a serum sample. In some embodiments, the lymphedema associated gene products are proteins. In some embodiments, the lymphedema associated gene products are mRNAs. In some embodiments, the lymphedema associated gene(s) is selected from the genes in Table 6 below. In certain embodiments, the lymphedema associated gene(s) in Table 6 is selected from the group consisting of Adrenomedullin (ADM), fibroblast growth factor 10 (FGF10), vascular endothelial growth factor A (VEGF), Angiopoietin 2 (ANGPT2), interleukin 1, alpha (IL1), interleukin 13 (IL-13), interferon, gamma (IFNG), leptin (LEP), hepatocyte growth factor (HGF), tumor necrosis factor alpha (TNFa), chorionic somatomammotropin hormone 1 (CSH), and Kallikrein-related peptidase 3 (KLK3).

In some aspects of the invention, methods are provided for assessing the responsiveness of a patient to a therapeutic regimen. In a single time point or a time course, a lymphedema dataset is evaluated before, during, and/or after a patient has been exposed to a therapy, which may include a drug, combination of drugs, non-pharmacologic intervention, and the like.

In some aspects of the invention, methods are provided for identifying compounds that modulate the expression of genes or the activity of gene products in lymphedema, as well as methods for the treatment of disease by administering such compounds to individuals exhibiting symptoms or tendencies. In some embodiments, the method of screening biologically active agents relies upon an analysis of a lymphedema dataset. In such methods, cells associated with lymphedema, e.g. skin cells of the dermis, subdermis, etc., are contacted in culture or in vivo with a candidate agent, and the effect on expression of one or more of the markers, e.g. a panel of markers, is determined. In some embodiments, the method of screening biologically active agents relies upon an analysis of an animal model of lymphedema. In some aspects of the invention, a useful model for lymphedema that allows molecular imaging methods is provided. Such imaging methods are useful in the screening of therapies, e.g. the suppression or activation of genes identified herein, in addition to other genetic, dietary, therapeutic, and other perturbation in lymphatic system. Such screening methods permit evaluation of the efficacy of treatments, and development of novel therapeutics for lymphedema.

Methods of analysis may include, without limitation, establishing a training dataset, and comparing the unknown sample to the training dataset as test datasets. Alternatively, simple quantitative measure of a panel of genes or gene products may be performed, and compared to a reference to determine differential expression. Other methods may utilize decision tree analysis, classification algorithms, regression analysis, and combinations thereof.

In some aspect of the invention, compounds and methods for the treatment of lymphedema are provided. In some embodiments, these compounds are NSAIDs. In some embodiments, these compounds are ketoprofen agents, e.g. ketoprofen or ketoprofen derivatives. In some embodiments, these compounds are formulated for topical delivery and administered topically. In some embodiments, these compounds are co-administered with a diuretic. In some embodiments, the volume of the affected tissue, i.e. the lymphedemous tissue, is measured. In some embodiments, 100 milliliters or more volume is lost from the affected tissue following treatment. In some embodiments, the architecture of the affected tissue is assayed. In some embodiments, the architecture of the affected tissue after treatment resembles the architecture of unaffected tissue.

In some aspect of the invention, compounds and methods for the prevention of lymphedema are provided. In some embodiments, these compounds are NSAIDs. In some embodiments, these compounds are ketoprofen agents, e.g. ketoprofen or ketoprofen derivatives, e.g. ketoprofen esters. In some embodiments, these compounds are formulated for topical delivery and administered topically. In some embodiments, the ketoprofen agent is administered prior to the predicted onset of lymphedema, e.g. prior to a surgical procedure that could induce lymphedema. In some embodiments, the ketoprofen agent is administered after the predicted onset of lymphedema, e.g. following a surgical procedure that could induce lymphedema. In some embodiments, these compounds are co-administered with a diuretic.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
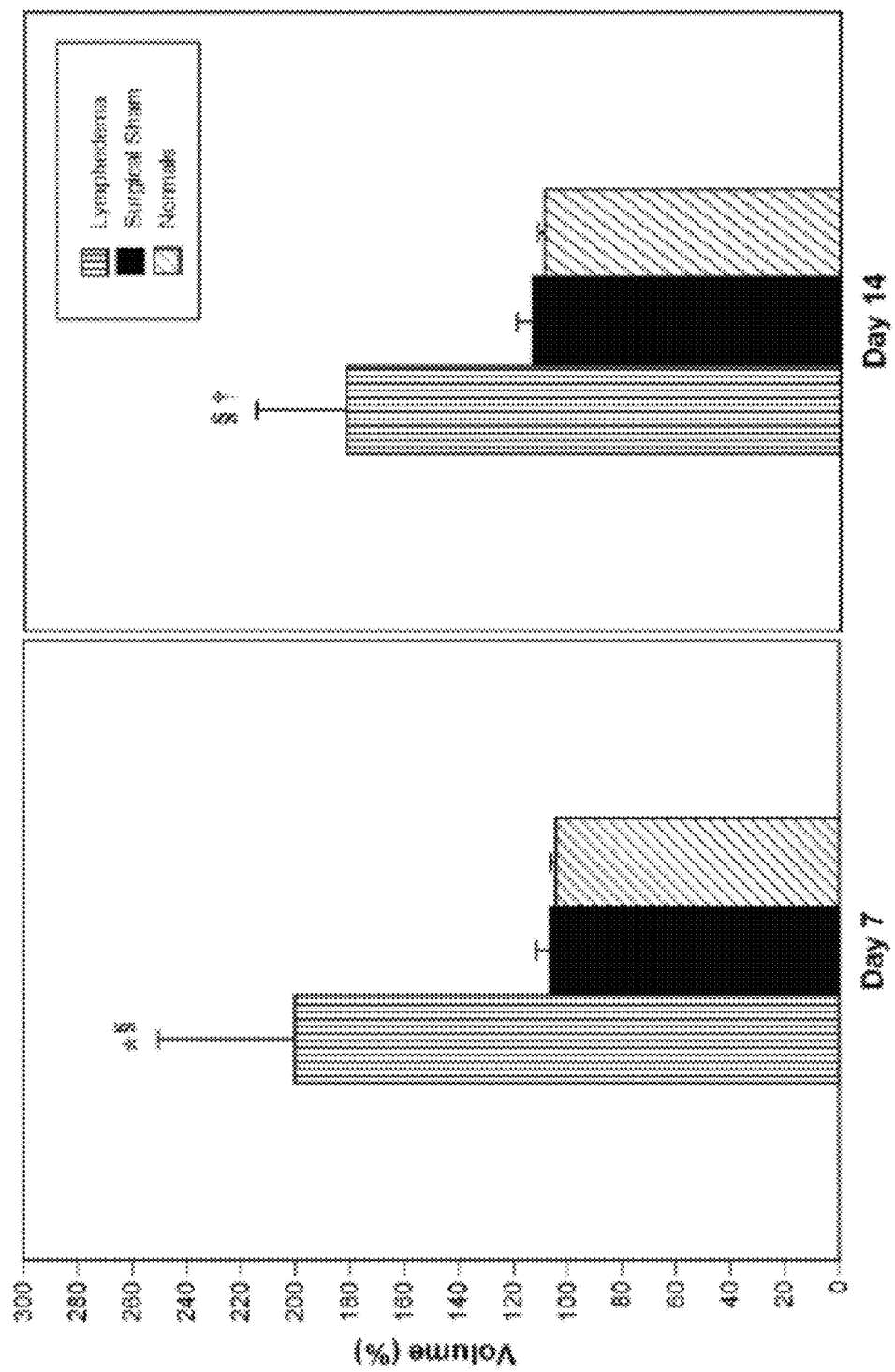
FIG. 1. Tail volume changes at post-surgical day 7 and at day 14.

Methods and compositions for the diagnosis and treatment of lymphedema are provided. The invention is based, in part, on the evaluation of the expression and role of genes that are differentially expressed in cutaneous samples, which genes provide a signature that is characteristic of lymphedema. Such sequences and signature profiles are useful in the diagnosis and monitoring of disease. The gene products are also useful as therapeutic targets for drug screening and action. As used herein, gene products may refer to mRNA transcribed from a gene, polypeptides encoded by a gene, or derivatives thereof, e.g. cDNA derived from an mRNA, polypeptide derived from an mRNA, and the like.

Lymphedema Expression Signatures

In some embodiments of the invention, a signature profile comprises expression information of one or more sequences set forth in Table 5 or Table 6, where the profile may include down-regulated sequences, up-regulated sequences, or both. One or more genes may be selected, i.e. two, three or four genes, sometimes five, six or seven genes, sometimes 8, 10 or 15 genes, sometimes 20 or more genes, e.g. 25, 30, 35, 40, 45 or more genes. The sequences may be selected for those that are more highly up-regulated, e.g. upregulated at least about 2-fold, at least about 3-fold, at least about 4-fold, at least about 5-fold or more, as set forth, for example, in Table 5. The sequences may be selected for those sequences involved in acute inflammation; for complement cascade; for wound healing; for stress response; for angiogenesis; for cytoskeletal proteins; for Wnt pathway; and for adipogenesis, as set forth, for example, in Table 5. The sequences may be selected for those sequences that encode for proteins that are secreted, or proteins located at the cell surface as set forth, for example, in Table 6.

Among the most highly upregulated sequences of Table 5 (upregulated greater than 2.5 fold) are included those involved in inflammation and immune responses, e.g. calgranulin B; tenascin C; lipocalin; stefin A3; secretory granule proteoglycan; L-plastin 2; follistatin; procollagen type IV; arachidonate 5-lipoxygenase activating protein; stromal cell-derived factor 1; thymosin beta 10; ferritin light chain 1; legumain; cathepsin C and cathepsin Z; lipocalin; cytotoxic T lymphocyte associated protein 2α; Fc receptor, IgE, high affinity I, γ polypeptide; Beta 2 microglobulin; and galactose binding lectin; those involved in the complement cascade, e.g. complement component factor B and complement component 1q; those involved in stress response, e.g. seleoprotein p; DNAj (hsp40) homolog; those involved in angiogenesis, e.g. thymosin beta 10; cytoskeletal proteins, e.g. caldesmon 1; and wnt pathway proteins, e.g. tenascin C.

Among the highly statistically upregulated human sequences of Table 6 are included those that encode for secreted proteins, for example, Adrenomedullin (ADM), fibroblast growth factor 10 (FGF10), vascular endothelial growth factor A (VEGF), Angiopoietin 2 (ANGPT2), interleukin 1, alpha (IL1), interleukin 13 (IL-13), interferon, gamma (IFNG), leptin (LEP), hepatocyte growth factor (HGF), tumor necrosis factor alpha (TNFa), chorionic somatomammotropin hormone 1 (CSH), and Kallikrein-related peptidase 3 (KLK3).

To systematically investigate the changes that mediate lymphedema processes; in vivo imaging of impaired immune traffic was performed in a model for acquired lymphatic insufficiency, with demonstration of impaired mobilization of immunocompetent cells from the lymphedematous region. These findings correlated with histopathological alterations and large-scale transcriptional profiling results. The transcriptional profiling of lymphedema tissue utilized a comprehensive cDNA microarray to investigate the molecular mechanisms of tissue response to lymphatic vascular insufficiency. The patterns of gene expression in lymphedema were contrasted with those observed in normal and surgical sham controls. Using rigorous statistical tools for analysis of the microarray data, patterns of cutaneous gene expression were identified that correlate with the imaging and light microscopic abnormalities and, thus, distinguish the tissue responses to persistent disruption of lymphatic function in the skin. Intense inflammatory changes in the dermis and the subdermis were found. The molecular pattern is predominated by the upregulation of genes related to acute inflammation, immune response, complement activation, wound healing, fibrosis, and oxidative stress response. Clustering of genes with known functions provides insights into processes and signaling pathways that comprise the chronic phase of this disease.

In some aspects of the invention, an investigative platform is provided that defines the inflammatory substrate of lymphedema and provides a relevant basis for future investigation of therapeutic interventions designed to ameliorate the disease and its deleterious effects upon the end-organ cutaneous and subcutaneous structures.

In some aspects of the invention, novel pathways that are implicated in the pathogenesis of the disease are provided, allowing assessment of the disease and its responses to therapeutic intervention.

In some aspects of the invention, therapeutic methods are provided for the prevention and/or treatment of lymphedema with molecular agents that can reduce inflammation, mitigate the immune response, reduce oxidative stress, and reduce the fibrotic response to wound healing. Treatments of particular interest include therapy initiated following an event involved in acquired lymphedema, e.g. following surgery for breast cancer. In one such embodiment, treatment with an anti-inflammatory agent or immunosuppressive agent, e.g. an NSAID, is initiated prior to overt evidence of lymphedema.

Such methods may prevent the induction of lymphedema or decrease the indicia of lymphedema when compared to a control in which the treatment is not provided. Alternatively, treatment with an anti-inflammatory agent or immunosuppressive agent, e.g. an NSAID, is initiated following initial indicia of lymphedema, and reduces the undesirable indicia of the condition relative to a control in which the treatment is not provided. In some embodiments, a second agent is provided to reduce the retention of fluid, i.e. a diurectic agent. The following criteria have been used in the literature to measure lymphedema: absolute increase in volume or percentage increase in volume as determined by water displacement, circumferential measurements and patient symptoms. It has been reported that both circumferential measurements and water displacement volumetry in women, with breast cancer had excellent interrater and test-retest reliability. Circumferential measurements are widely used because tape measures are readily available and because volumetric measurement is logistically difficult. One common approach involves measuring the circumferences of both arms at points 13 to 15 cm proximal and 10 cm distal to the lateral epicondyle of the humerus. Differences greater than 2.0 cm at any point may be defined by some as clinically significant. Other methods for assessing lymphedema include lymphoscintigraphy, MRI, CT scanning and ultrasound. In other embodiments, the indicia for lymphedema is or includes a gene expression profile as described herein. Such indicia may be decreased by at least 10%, by at least 20%, by at least 30%, by at least 50%, by at least 75%, by at least 90% or more by the methods of treatment provided herein.

For some methods of the invention, a panel of sequences will be selected for a gene expression signature, comprising, for example, at least one, at least two, at least three, at least four, at least five, at least ten, at least 15, at least 20, and may include substantially all the sequences of a specific Table (i.e. Table 2, Table 5, Table 6, particularly Table 6), or may be limited to not more than about 100 distinct sequences, not more than about 80 distinct sequences, not more than about 25 distinct sequences, not more than about 6 sequences, and the like. The selection of sequences for inclusion in arrays, use in diagnostic panels, and the like may be based on representation of a sequence in one or more of the pathways, e.g. selecting sequences present in specific pathways as described above and as known in the art, sequences that encode secreted or cell surface proteins, and the like. The use of human homologs of the sequences is of particular interest. Selection of sequences may alternatively be based on a cut-off for significance or for fold-change in expression, e.g. those sequences have a fold-change of at least about 2, about 3, at least about 6, at least 10, or more. Selection of sequences may also be based on biological activity grouping, e.g. as set forth in above, or in Table 5, or as known in the art, where genes can be divided into acute inflammation pathways, immune response pathways, complement cascade, wound healing and fibrosis, stress response, angiogenesis, cytoskeletal genes, wnt pathway genes, and adipogenesis genes.

The identification of lymphedema-associated genes provides diagnostic and prognostic methods, which detect the occurrence of the disorder; or assess an individual's susceptibility to such disease, by detecting altered expression of lymphedema associated genes. Early detection of genes or their products can be used to determine the occurrence of developing disease, thereby allowing for intervention with appropriate preventive or protective measures.

Various techniques and reagents find use in the diagnostic methods of the present invention. In some embodiments of the invention, a blood sample, e.g. a whole blood, or a serum or cell sample derived therefrom, is assayed for the presence of the gene products encoded by lymphedema associated genes. In some embodiments of the invention, skin (cutaneous) samples, or samples derived from skin, are assayed for the presence of genes or gene products encoded by lymphedema associated genes. Such genes or gene products may be detected through specific binding members. Various formats find use for such assays, including qPCR, polynucleotide arrays, antibody arrays; ELISA and RIA formats; binding of labeled antibodies in suspension/solution and detection by flow cytometry, mass spectroscopy, and the like.

The aforementioned lymphedema-associated genes and their products also provide points of intervention to block, i.e. prevent, the pathophysiologic processes leading to disease, and also provides therapeutic intervention, i.e. treatment. Functional modulation of these genes and their products can be used to prevent, attenuate or reduce damage in prophylactic strategies in patients at high-risk of lymphedema.

Animal Models of Lymphedema

In some embodiments of the invention, an animal model is provided for screening of candidate agents for the treatment of lymphedema. The tissue responses to lymphatic vascular insufficiency, are assessed utilizing dynamic, in vivo imaging of the impaired immune traffic in a murine model of acquired lymphatic insufficiency that simulates lymphatic dysfunction of post-surgical lymphedema. Data thus obtained is optionally correlated with an assessment of the cutaneous histopathology in the lymphedema tissue.

In the animal model of the invention, a mouse or rat is surgically treated, to produce lymphatic ablation of the tail. Post-surgical edematous enlargement of the tails is observed typically after post-surgical day 2, and persists for at least about 2 weeks, or longer. Histological specimens derived from the lymphedematous tails are characterized by the presence of marked acute inflammatory changes. There is a notable increase in cellularity, with an increase in the number of observed fibroblasts and histiocytes, as well as a large infiltration of neutrophils. Granulation tissue is observed closer to the center of the section, with bystander destruction of muscle tissue. In addition, there is hyperkeratosis and spongiosis and edema of the epidermis, with irregularity of the epidermal/dermal junction, elongation of the dermal papillae, and a 2-3× expansion of tissue between the bone and the epidermis.

The lymphatic vasculature participates in the immune response through the continuous transportation of white blood cells and antigen-presenting cells. The constellation of histological observations in this model, otherwise unexplained by impaired interstitial fluid mobilization, suggests that derangements in lymphatic immune traffic contribute to the biology of lymph stagnation. In the methods of the invention, quantifiable changes in immune traffic may be used as a method of assessing lymphedema. In such methods, a sample of bioluminescent immune cells, e.g. cells expressing a luciferase marker, etc. are introduced into the distal tail, and the clearance of cells from the tail is then monitored. The relative photon density present in the tail, compared to a control animal, e.g. an untreated animal, a lymphedematous animal in the absence or presence of a treatment of interest, etc., is measured. It is found that the presence of lymphedema causes an increase in the retention of the labeled cells in the tail, which increase is readily measured by photon density.

Identification of Genes Associated with Lymphedema

In order to identify lymphedema-associated genes, a biopsy is taken from cutaneous tissue affected by lymphedema, and from control, unaffected tissue. In some instances, the tissue is mouse. In some instances, the tissue is human tissue. Examples 1 and 2 below are illustrative of such screens in mice and humans, respectively. In some instances, e.g. Example 2, lymphedemous and control tissues are taken from the same individual. In other words, a "paired analysis" is performed. RNA, either total or mRNA, is isolated from such tissues. See, for example, Sambrook et al., 1989, Molecular Cloning, A Laboratory Manual, Cold Spring Harbor Press, New York; and Ausubel, F. M. et al., eds., 1987-1993, Current Protocols in Molecular Biology, John Wiley & Sons, Inc., New York, both of which are incorporated herein by reference in their entirety. Differentially expressed genes are detected by comparing gene expression levels between the affected and control tissue. Transcripts within the collected RNA samples that represent differentially expressed genes may be identified by utilizing a variety of methods known to those of skill in the art, including differential screening, subtractive hybridization, differential display, or hybridization to an array comprising a plurality of gene sequences.

"Differential expression" as used herein refers to both quantitative as well as qualitative differences in the genes' temporal and/or tissue expression patterns. Thus, a differentially expressed gene may have its expression activated or inactivated in normal versus disease conditions, or in control versus experimental conditions. Preferably, a regulated gene will exhibit an expression pattern within a given tissue or cell type that is detectable in either control or disease subjects, but is not detectable in both. Detectable, as used herein, refers to an RNA expression pattern or presence of polypeptide product that is detectable via the standard techniques of differential display, reverse transcription- (RT-) PCR and/or Northern analyses, ELISA, RIA, metabolic assays, etc., which are well known to those of skill in the art. Generally, differential expression means that there is at least a 20% change, and in other instances at least a 2-, 3-, 5- or 10-fold difference between disease and control tissue expression. The difference usually is one that is statistically significant, meaning that the probability of the difference occurring by chance (the P-value) is less than some predetermined level (e.g., 5%). Usually the confidence level (P value) is <0.05, more typically <0.01, and in other instances, <0.001. The identification of genes that are differentially expressed in lymphedemous versus non-affected tissue can be made by any convenient method in the art for comparing gene-specific RNA or proteins in a tissue, e.g. microarrays, qPCR, mass spectroscopy; see, for example, the experimental section below. As discussed above, Table 2, Table 5 and Table 6 provide examples of sequences that have significantly altered expression in lymphedema, which genes may be induced or repressed as indicated in the table. In some embodiments, the sequences of interest have a "fold change" as set forth in Table 5 or Table 6 of at least about 2.5, of at least 4; of a least about 5, of at least about 6, or more.

Nucleic Acids

The sequences of lymphedema-associated genes find use in diagnostic and prognostic methods, for the recombinant production of the encoded polypeptide, and the like. A list of lymphedema associated genetic sequences is provided in Table 2, Table 5, or Table 6. The nucleic acids of the invention include nucleic acids having a high degree of sequence similarity or sequence identity to one of the sequences provided, and also include homologs, particularly human homologs. Sequence identity can be determined by hybridization under stringent conditions, for example, at 50° C. or higher and 0.1×SSC (9 mM NaCl/0.9 mM Na citrate). Hybridization methods and conditions are well known in the art, see, e.g., U.S. Pat. No. 5,707,829. Nucleic acids that are substantially identical to the provided nucleic acid sequence, e.g. allelic variants, genetically altered versions of the gene, etc., bind to one of the sequences provided in Table 12, Table 5 or Table 6. Further specific guidance regarding the preparation of nucleic acids is provided by Fleury et al. (1997) Nature Genetics 15:269-272; Tartaglia et al., PCT Publication No. WO 96/05861; and Chen et al., PCT Publication No. WO 00/06087, each of which is incorporated herein in its entirety.

The genes listed may be obtained using various methods well known to those skilled in the art, including but not limited to the use of appropriate probes to detect the genes within an appropriate cDNA or genomic DNA library, antibody screening of expression libraries to detect cloned DNA fragments with shared structural features, direct chemical synthesis, and amplification protocols. Libraries are preferably prepared from cutaneous cells. Cloning methods are described in Berger and Kimmel, Guide to Molecular Cloning Techniques, Methods in Enzymology, 152, Academic Press, Inc. San Diego, Calif.; Sambrook, et al. (1989) Molecular Cloning—A Laboratory Manual (2nd ed) Vols. 1-3, Cold Spring Harbor Laboratory, Cold Spring Harbor Press, NY; and Current Protocols (1994), a joint venture between Greene Publishing Associates, Inc. and John Wiley and Sons, Inc.

The sequence obtained from clones containing partial coding sequences or non-coding sequences can be used to obtain the entire coding region by using the RACE method (Chenchik et al. (1995) CLONTECHniques (X) 1: 5-8). Oligonucleotides can be designed based on the sequence obtained from the partial clone that can amplify a reverse transcribed mRNA encoding the entire coding sequence. Alternatively, probes can be used to screen cDNA libraries prepared from an appropriate cell or cell line in which the gene is transcribed. Once the target nucleic acid is identified, it can be isolated and cloned using well-known amplification techniques. Such techniques include the polymerase chain reaction (PCR) the ligase chain reaction (LCR), Qβ-replicase amplification, the self-sustained sequence replication system (SSR) and the transcription based amplification system (TAS). Such methods include, those described, for example, in U.S. Pat. No. 4,683,202 to Mullis et al.; PCR Protocols A Guide to Methods and Applications (Innis et al. eds) Academic Press Inc. San Diego, Calif. (1990); Kwoh et al. (1989) Proc. Natl. Acad. Sci. USA 86: 1173; Guatelli et al. (1990) Proc. Natl. Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4: 560; and Barringer et al. (1990) Gene 89: 117.

As an alternative to cloning a nucleic acid, a suitable nucleic acid can be chemically synthesized. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids can be cDNAs or genomic DNAs, as well as fragments thereof. The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding a polypeptide of the invention.

A genomic sequence of interest comprises the nucleic acid present between the initiation codon and the stop codon, as defined in the listed sequences, including all of the introns that are normally present in a native chromosome. It can further include the 3' and 5' untranslated regions found in the mature mRNA. It can further include specific transcriptional and translational regulatory sequences, such as promoters, enhancers, etc., including about 1 kb, but possibly more, of flanking genomic DNA at either the 5' or 3' end of the transcribed region. The genomic DNA flanking the coding region, either 3' or 5', or internal regulatory sequences as sometimes found in introns, contains sequences required for proper tissue; stage-specific, or disease-state specific expression, and are useful for investigating the up-regulation of expression.

Probes specific to the nucleic acid of the invention can be generated using the nucleic acid sequence disclosed in Table 2, Table 5 or Table 6. The probes are preferably at least about 18 nt, 25 nt, 50 nt or more of the corresponding contiguous sequence of one of the sequences provided in Table 2, Table 5 or Table 6, and are usually less than about 2, 1, or 0.5 kb in length. Preferably, probes are designed based on a contiguous sequence that remains unmasked following application of a masking program for masking low complexity, e.g. BLASTX. Double or single stranded fragments can be obtained from the DNA sequence by chemically synthesizing oligonucleotides in accordance with conventional methods, by restriction enzyme digestion, by PCR amplification, etc. The probes can be labeled, for example, with a radioactive, biotinylated, or fluorescent tag.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome.

The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other. For hybridization probes, it may be desirable to use nucleic acid analogs, in order to improve the stability and binding affinity. The term "nucleic acid" shall be understood to encompass such analogs.

Polypeptides

Polypeptides encoded by lymphedema-associated genes are of interest for screening methods, as reagents to raise antibodies, as therapeutics, and the like. Such polypeptides can be produced through isolation from natural sources, recombinant methods and chemical synthesis. In addition, functionally equivalent polypeptides may find use, where the equivalent polypeptide may be a homolog, e.g. a human homolog, may contain deletions, additions or substitutions of amino acid residues that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity as the polypeptide encoded by an lymphedema associated gene, as provided in Table 2, Table 5 or Table 6.

Peptide fragments find use in a variety of methods, where fragments are usually at least about 10 amino acids in length, about 20 amino acids in length, about 50 amino acids in length, or longer, up to substantially full length. Fragments of particular interest include fragments comprising an epitope, which can be used to raise specific antibodies. Soluble fragment of cell surface proteins are also of interest, e.g. truncated at transmembrane domains.

The polypeptides may be produced by recombinant DNA technology using techniques well known in the art. Methods that are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

Typically, the coding sequence is placed under the control of a promoter that is functional in the desired host cell to produce relatively large quantities of the gene product. An extremely wide variety of promoters are well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, *E. coli*, other bacterial hosts, yeast, and various higher eukaryotic cells such as the COS, CHO and HeLa cells lines and myeloma cell lines.

In mammalian host cells, a number of viral-based expression systems may be used, including retrovirus, lentivirus, adenovirus, adeno associated virus, and the like. In cases where an adenovirus is used as an expression vector, the coding sequence of interest can be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts.

Specific initiation signals may also be required for efficient translation of the genes. These signals include the ATG initiation codon and adjacent sequences. In cases where a complete gene, including its own initiation codon and adjacent sequences, is inserted into the appropriate expression vector, no additional translational control signals may be needed. However, in cases where only a portion of the gene coding sequence is inserted, exogenous translational control signals must be provided. These exogenous translational control signals and initiation codons can be of a variety of origins, both natural and synthetic. The efficiency of expression may be enhanced by the inclusion of appropriate transcription enhancer elements, transcription terminators, etc.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines that stably express the differentially expressed or pathway gene protein may be engineered. Rather than using expression vectors that contain viral origins of replication, host cells can be transformed with DNA controlled by appropriate expression control elements, and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the target protein. Such engineered cell lines may be particularly useful in screening and evaluation of compounds that affect the endogenous activity of the differentially expressed or pathway gene protein. A number of selection systems may be used, including but not limited to the herpes simplex virus thymidine kinase, hypoxanthine-guanine phosphoribosyltransferase, and adenine phosphoribosyltransferase genes. Antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

The polypeptide may be labeled, either directly or indirectly. Any of a variety of suitable labeling systems may be used, including but not limited to, radioisotopes such as $^{125}$I; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by an Fab expression library.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification, Academic Press, Inc. N.Y. (1990)).

As an option to recombinant methods, polypeptides and oligopeptides can be chemically synthesized. Such methods typically include solid-state approaches, but can also utilize solution based chemistries and combinations or combinations of solid-state and solution approaches. Examples of solid-state methodologies for synthesizing proteins are described by Merrifield (1964) J. Am. Chem. Soc. 85:2149; and Houghton (1985) Proc. Natl. Acad. Sci., 82:5132. Fragments of a protein can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993).

Databases

Also provided are databases of expression profiles of lymphedema datasets. Such databases will typically comprise expression profiles of individuals having susceptible phenotypes, negative expression profiles, etc., where such profiles are as described above.

The analysis and database storage may be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data may be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program is preferably implemented in a high level procedural or object oriented programming language to communicate with a computer system. However, the programs can be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

Nucleic acids and polypeptides in the expression signatures and databases described herein and/or as identified by the methods described above are useful in a number of applications. For example, they may be used in methods of diagnosing and prognosing lymphedema. They may be used as targets of lymphedema therapy. They may be used in methods for screening for therapeutic agents to treat and prevent lymphedema. Some of these applications are described in greater detail below.

Diagnostic and Prognostic Methods

The differential expression of lymphedema associated genes indicates that these sequences can serve as markers for diagnosis of disease, and in prognostic evaluations to detect individuals at risk for disease, to predict responsiveness to treatment, to monitor efficacy of treatment, etc. Prognostic methods can also be utilized to monitor an individual's health status prior to and after an episode, as well as in the assessment of the severity of the episode and the likelihood and extent of recovery In general, such diagnostic and prognostic methods involve detecting an altered level of expression of lymphedema associated genes or gene products in the cells or tissue of an individual or a sample therefrom, to generate an expression profile. One or more gene products may be detected, i.e. two, three or four gene products, sometimes five, six or seven gene products, sometimes 8, 10 or 15 gene products, sometimes 20 or more gene products, e.g. 25, 30, 35, 40, 45 or more gene products. A variety of different assays can be utilized to detect an increase in lymphedema associated gene expression, including both methods that detect gene transcript and protein levels. More specifically, the diagnostic and prognostic methods disclosed herein involve obtaining a sample from an individual and determining at least qualitatively, and preferably quantitatively, the level of a lymphedema associated genes product expression in the sample. Usually this determined value or test value is compared against some type of reference or baseline value.

The term expression profile is used broadly to include a genomic expression profile, e.g., an expression profile of mRNAs, or a proteomic expression profile, e.g., an expression profile of one or more different proteins. Profiles may be generated by any convenient means for determining differential gene expression between two samples, e.g. quantitative hybridization of mRNA, labeled mRNA, amplified mRNA, cRNA, etc., quantitative PCR, ELISA for protein quantitation, and the like. Expression profiles are typically a normalized representation of the expression levels of genes of interest. By "normalized", it is meant that the profiles are arrived at by comparing the expression level(s) of the gene(s) of interest to a reference level, e.g. the level of expression of a gene or genes that is constant in a non-affected and a lymphedemous sample. For example, an "RNA expression profile", or simply "RNA profile", of a patient sample is the normalized expression level of the one or more genes in a patient sample as determined by measuring the amount of RNA transcribed from the one or more genes. As another example, a "protein expression profile", or simply "protein profile", of a patient sample is the normalized expression level of the one or more genes in a patient sample as determined by measuring the amount of amino acid product encoded by a gene.

In some instances, the expression profile is converted into an expression score, and that score is then used for diagnostic or prognostic purposes. An "expression score" refers to a single metric value that represents the sum of the weighted expression levels of one or more genes of interest, more usually two or more genes of interest, in a patient sample. For example, an "RNA expression score", or simply "RNA score", of a patient sample is the weighted expression level of the one or more genes in a patient sample as determined by measuring the amount of RNA transcribed from the one or more genes. As another example, a "protein expression profile", or simply "protein profile", of a patient sample is the weighted expression level of the one or more genes in a patient sample as determined by measuring the amount of amino acid product encoded by a gene. Weighted expression levels are calculated by multiplying the normalized expression level of each gene by its "weight", the weight of each gene being determined by analysis of a reference dataset, or "training set", by, e.g. Principle Component Analysis (PCA), Linear discriminant analysis (LDA), Fisher's linear discriminant analysis, or the like, as are known in the art. The weighted expression levels are then totaled and in some cases averaged to arrive at a single weighted expression level for the one or more genes analyzed. Thus, for example, when PCA is used, the expression score is the weighted sum of expression levels of the genes of interest in a sample, where the weights are defined by their first principal component as defined by a reference dataset. Any dataset relating to patients having lymphedema may be used as a reference dataset.

The expression profile may be generated from a biological sample using any convenient protocol. While a variety of different manners of generating expression profiles are known, such as those employed in the field of differential gene expression analysis, one representative and convenient type of protocol for generating expression profiles is array based gene expression profile generation protocols. Following obtainment of the expression profile from the sample being assayed, the expression profile is compared with a reference or control profile to make a diagnosis regarding the susceptibility phenotype of the cell or tissue from which the sample was obtained/derived. Typically a comparison is made with a set of cells from an unaffected, normal source. Additionally, a reference or control profile may be a profile that is obtained from a cell/tissue known to be predisposed to lymphedema, and therefore may be a positive reference or control profile.

In certain embodiments, the obtained expression profile is compared to a single reference/control profile to obtain information regarding the phenotype of the cell/tissue being assayed. In yet other embodiments, the obtained expression profile is compared to two or more different reference/control profiles to obtain more in depth information regarding the phenotype of the assayed cell/tissue. For example, the obtained expression profile may be compared to a positive and negative reference profile to obtain confirmed information regarding whether the cell/tissue has the phenotype of interest.

The difference values, i.e. the difference in expression in the presence and absence of radiation may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference. Methods of comparing expression profiles are also described above. A statistical analysis step is then performed to obtain the weighted contribution of the set of predictive genes.

In one embodiment of the invention, blood samples, or samples derived from blood, e.g. plasma, serum, etc. are assayed for the presence of polypeptides encoded by lymphedema associated genes, e.g. cell surface and, of particular interest, secreted polypeptides. Such polypeptides may be detected through specific binding members. The use of antibodies for this purpose is of particular interest. Various formats find use for such assays, including antibody arrays; ELISA and RIA formats; binding of labeled antibodies in suspension/solution and detection by flow cytometry, mass spectroscopy, and the like. Detection may utilize one or a panel of specific binding members, e.g. specific for at least about 2, at least about 5, at least about 10, at least about 15 or more different gene products. A subset of genes and gene products of interest for assays are provided in Table 2, Table 5 or Table 6.

In another embodiment, in vivo imaging is utilized to detect the presence of lymphedema associated gene, e.g. in cutaneous tissue. Such methods may utilize, for example, labeled antibodies or ligands specific for cell surface lymphedema associated gene products. Included for such methods are gene products differentially expressed in dermal, epidermal, or whole cutaneous tissue samples, which can be localized by in situ binding of a labeled reagent. In these embodiments, a detectably-labeled moiety, e.g., an antibody, ligand, etc., which is specific for a polypeptide of interest is administered to an individual (e.g., by injection), and labeled cells are located using standard imaging techniques, including, but not limited to, magnetic resonance imaging, computed tomography scanning, and the like. Detection may utilize one or a cocktail of imaging reagents e.g. imaging reagents specific for at least about 2, at least about 5, at least about 10, at least about 15 or more different gene products.

In another embodiment, an mRNA sample from cutaneous tissue is analyzed for the genetic signature indicating lymphedema. Expression signatures typically utilize a panel of genetic sequences, e.g. a microarray format; multiplex amplification, etc., coupled with analysis of the results to determine if there is a statistically significant match with a disease signature.

Nucleic acids, e.g. primers, hybridization sequences, etc, or binding members such as antibodies that are specific for polypeptides derived from the sequence of one of the sequences provided in Table 2, Table 5, or Table 6 can be used to screen patient samples for increased expression of the corresponding mRNA or protein. Samples can be obtained from a variety of sources. For example, since the methods are designed primarily to diagnosis and assess risk factors for humans, samples are typically obtained from a human subject. However, the methods can also be utilized with samples obtained from various other mammals, such as primates, e.g. apes and chimpanzees, mice, cats, rats, and other animals. Such samples are referred to as a patient sample.

Samples can be obtained from the tissues or fluids of an individual, as well as from cell cultures or tissue homogenates. For example, samples can be obtained from whole skin, dermal layers, epidermal layers, etc. Also included in the term are derivatives and fractions of such cells and fluids. Where cells are analyzed, the number of cells in a sample will often be at least about $10^2$, usually at least $10^3$, and may be about $10^4$ or more. The cells may be dissociated, in the case of solid tissues, or tissue sections may be analyzed. Alternatively a lysate of the cells may be prepared.

Diagnostic samples are collected any time after an individual is suspected to have lymphedema, etc. or has undergone an event that predisposes to lymphedema. In prophylactic testing; samples can be obtained from an individual who present with risk factors that indicate a susceptibility, which risk factors include breast cancer surgery, etc. as part of a routine assessment of the individual's health status.

The various test values determined for a sample from an individual believed to suffer lymphedema, and/or a tendency to lymphedema typically are compared against a baseline value to assess the extent of increased or decreased expression, if any. This baseline value can be any of a number of different values. In some instances, the baseline value is a value established in a trial using a healthy cell or tissue sample that is run in parallel with the test sample. Alternatively, the baseline value can be a statistical value (e.g., a mean or average) established from a population of control cells or individuals. For example, the baseline value can be a value or range that is characteristic of a control individual or control population. For instance, the baseline value can be a statistical value or range that is reflective of expression levels for the general population, or more specifically, healthy individuals not susceptible to lymphedema.

Nucleic Acid Screening Methods

Some of the diagnostic and prognostic methods that involve the detection of a lymphedema associated gene transcript begin with the lysis of cells and subsequent purification of nucleic acids from other cellular material, particularly mRNA transcripts. A nucleic acid derived from an mRNA transcript refers to a nucleic acid for whose synthesis the mRNA transcript, or a subsequence thereof, has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample. Thus, suitable samples include, but are not limited to, mRNA transcripts of lymphedema associated genes, cDNA reverse transcribed from the mRNA, cRNA transcribed from the cDNA, DNA amplified from lymphedema associated nucleic acids, and RNA transcribed from amplified DNA.

A number of methods are available for analyzing nucleic acids for the presence of a specific sequence, e.g. upregulated expression. The nucleic acid may be amplified by conventional techniques, such as the polymerase chain reaction (PCR), to provide sufficient amounts for analysis. The use of the polymerase chain reaction is described in Saiki et al. (1985) *Science* 239:487, and a review of techniques may be found in Sambrook, et al. *Molecular Cloning: A Laboratory Manual*, CSH Press 1989, pp. 14.2-14.33.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2,7-dimethoxy-4,5-dichloro-6-carboxyfluorescein (JOE), 6-carboxy-X-rhodamine (ROX), 6-carboxy-2,4,7,4,7-hexachlorofluorescein (HEX), 5-carboxyfluorescein (5-FAM) or N,N,N,N-tetramethyl-6-carboxyrhodamine (TAMRA), radioactive labels, e.g. $^{32}P$, $^{35}S$, $^3H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified, labeled, cloned fragment, etc. is analyzed by one of a number of methods known in the art. Probes may be hybridized to northern or dot blots, or liquid hybridization reactions performed. The nucleic acid may be sequenced by dideoxy or other methods, and the sequence of bases compared to a wild-type sequence. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Fractionation is performed by gel or capillary electrophoresis, particularly acrylamide or agarose gels.

In situ hybridization methods are hybridization methods in which the cells are not lysed prior to hybridization. Because the method is performed in situ, it has the advantage that it is not necessary to prepare RNA from the cells. The method usually involves initially fixing test cells to a support (e.g., the walls of a microtiter well) and then permeabilizing the cells with an appropriate permeabilizing solution. A solution containing labeled probes for a lymphedema associated gene is then contacted with the cells and the probes allowed to hybridize with the nucleic acids. Excess probe is digested, washed away and the amount of hybridized probe measured. This approach is described in greater detail by Harris, D. W. (1996) Anal. Biochem. 243:249-256; Singer, et al. (1986) Biotechniques 4:230-250; Haase et al. (1984) Methods in Virology, vol. VII, pp. 189-226; and Nucleic Acid Hybridization: A Practical Approach (Hames, et al., eds., 1987).

A variety of so-called "real time amplification" methods or "real time quantitative PCR" methods can also be utilized to determine the quantity of lymphedema associated gene mRNA present in a sample. Such methods involve measuring the amount of amplification product formed during an amplification process. Fluorogenic nuclease assays are one specific example of a real time quantitation method that can be used to detect and quantitate lymphedema associated gene transcripts. In general such assays continuously measure PCR product accumulation using a dual-labeled fluorogenic oligonucleotide probe—an approach frequently referred to in the literature simply as the "TaqMan" method.

The probe used in such assays is typically a short (ca. 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. For measuring a lymphedema associated gene transcript, the probe is designed to have at least substantial sequence complementarity with a probe binding site on a lymphedema associated gene transcript. Upstream and downstream PCR primers that bind to regions that flank the lymphedema associated gene are also added to the reaction mixture.

When the probe is intact, energy transfer between the two fluorophors occurs and the quencher quenches emission from the reporter. During the extension phase of PCR, the probe is cleaved by the 0.5° nuclease activity of a nucleic acid polymerase such as Taq polymerase, thereby releasing the reporter dye from the polynucleotide-quencher complex and resulting in an increase of reporter emission intensity that can be measured by an appropriate detection system.

One detector which is specifically adapted for measuring fluorescence emissions such as those created during a fluorogenic assay is the ABI 7700 manufactured by Applied Biosystems, Inc. in Foster City, Calif. Computer software provided with the instrument is capable of recording the fluorescence intensity of reporter and quencher over the course of the amplification. These recorded values can then be used to calculate the increase in normalized reporter emission intensity on a continuous basis and ultimately quantify the amount of the mRNA being amplified.

Additional details regarding the theory and operation of fluorogenic methods for making real time determinations of the concentration of amplification products are described, for example, in U.S. Pat. No. 5,210,015 to Gelfand, U.S. Pat. No. 5,538,848 to Livak, et al., and U.S. Pat. No. 5,863,736 to Haaland, as well as Heid, C. A., et al., Genome Research, 6:986-994 (1996); Gibson, U. E. M, et al., Genome Research 6:995-1001 (1996); Holland, P. M., et al., Proc. Natl. Acad. Sci. USA 88:7276-7280, (1991); and Livak, K. J., et al., PCR Methods and Applications 357-362 (1995), each of which is incorporated by reference in its entirety *Polypeptide Screening Methods*

Screening for expression of the subject sequences may be based on the functional or antigenic characteristics of the protein. Various immunoassays designed to quantitate proteins encoded by the sequences corresponding to the sequences provided in Table 2, Table 5 or Table 6 may be used in screening. Functional, or metabolic, protein assays have proven to be effective screening tools. The activity of the encoded protein in oxidative phosphorylation assays, etc., may be determined by comparison with unaffected individuals.

Detection may utilize staining of cells or histological sections, performed in accordance with conventional methods, using antibodies or other specific binding members that specifically bind to the lymphedema associated polypeptides. The antibodies or other specific binding members of interest, e.g. receptor ligands, are added to a cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Final detection uses a substrate that undergoes a color change in the presence of the peroxidase. The absence or presence of antibody binding may be determined by various methods, including flow cytometry of dissociated cells, microscopy, radiography, scintillation counting, etc.

An alternative method for diagnosis depends on the in vitro detection of binding between antibodies and the polypeptide corresponding to a sequence of Table 2, Table 5 or Table 6 in a blood sample, cell lysate, etc. Measuring the concentration of the target protein in a sample or fraction thereof may be accomplished by a variety of specific assays. A conventional sandwich type assay may be used. For example, a sandwich assay may first attach specific antibodies to an insoluble surface or support. The particular manner of binding is not crucial so long as it is compatible with the reagents and overall methods of the invention. They may be bound to the plates covalently or non-covalently, preferably non-covalently.

The insoluble supports may be any compositions to which polypeptides can be bound, which is readily separated from soluble material, and which is otherwise compatible with the overall method. The surface of such supports may be solid or porous and of any convenient shape. Examples of suitable insoluble supports to which the receptor is bound include beads, e.g. magnetic beads, membranes and microtiter plates. These are typically made of glass, plastic (e.g. polystyrene), polysaccharides, nylon or nitrocellulose. Microtiter plates are especially convenient because a large number of assays can be carried out simultaneously, using small amounts of reagents and samples.

Patient sample lysates are then added to separately assayable supports (for example, separate wells of a microtiter plate) containing antibodies. Preferably, a series of standards, containing known concentrations of the test protein is assayed in parallel with the samples or aliquots thereof to serve as controls. Preferably, each sample and standard will be added to multiple wells so that mean values can be obtained for each. The incubation time should be sufficient for binding, generally, from about 0.1 to 3 hr is sufficient. After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing a second antibody is applied. The antibody will bind to one of the proteins of interest with sufficient specificity such that it can be distinguished from other components present. The second antibodies may be labeled to facilitate direct, or indirect quantification of binding. Examples of labels that permit direct measurement of second receptor binding include radiolabels, such as $^3$H or $^{125}$I, fluorescers, dyes, beads, chemiluminescers, colloidal particles, and the like. Examples of labels that permit indirect measurement of binding include enzymes where the substrate may provide for a colored or fluorescent product. In a preferred embodiment, the antibodies are labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. The incubation time should be sufficient for the labeled ligand to bind available molecules. Generally, from about 0.1 to 3 hr is sufficient, usually 1 hr sufficing.

After the second binding step, the insoluble support is again washed free of non-specifically bound material, leaving the specific complex formed between the target protein and the specific binding member. The signal produced by the bound conjugate is detected by conventional means. Where an enzyme conjugate is used, an appropriate enzyme substrate is provided so a detectable product is formed.

Other immunoassays are known in the art and may find use as diagnostics. Ouchterlony plates provide a simple determination of antibody binding. Western blots may be performed on protein gels or protein spots on filters, using a detection system specific for the lymphedema associated polypeptide as desired, conveniently using a labeling method as described for the sandwich assay.

In some cases, a competitive assay will be used. In addition to the patient sample, a competitor to the targeted protein is added to the reaction mix. The competitor and the lymphedema associated polypeptide compete for binding to the specific binding partner. Usually, the competitor molecule will be labeled and detected as previously described, where the amount of competitor binding will be proportional to the amount of target protein present. The concentration of competitor molecule will be from about 10 times the maximum anticipated protein concentration to about equal concentration in order to make the most sensitive and linear range of detection.

The detection methods can be provided as part of a kit. Thus, the invention further provides kits for detecting the presence of an mRNA corresponding to a sequence of Table I, II, or III, and/or a polypeptide encoded thereby, in a biological sample. Procedures using these kits can be performed by clinical laboratories, experimental laboratories, medical practitioners, or private individuals. The kits of the invention for detecting a polypeptide comprise a moiety that specifically binds the polypeptide, which may be a specific antibody. The kits of the invention for detecting a nucleic acid comprise a moiety that specifically hybridizes to such a nucleic acid. The kit may optionally provide additional components that are useful in the procedure, including, but not limited to, buffers, developing reagents, labels, reacting surfaces, means for detection, control samples, standards, instructions, and interpretive information.

Diagnostic Arrays

Arrays provide a high throughput technique to assay a large number of polynucleotides or polypeptides in a sample. In one aspect of the invention, an array is constructed comprising one or more probes that specifically bind to lymphedema associated genes or gene products, preferably comprising probes specific for at least 6 distinct markers, at least about 10, at least 25, at least 50 or more. This technology is used as a tool to quantitate expression. Arrays can be created by spotting a probe onto a substrate (e.g., glass, nitrocellulose, etc.) in a two-dimensional matrix or array having bound probes. The probes can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA*. 93(20):10614-9; Schena at al. (1995) *Science* 270(5235):467-70; Shalon et al. (1996) *Genome Res*. 6(7):639-45, U.S. Pat. No. 5,807,522, EP 799 897; WO 97/29212; WO 97/27317; EP 785 280; WO 97/02357; U.S. Pat. No. 5,593,839; U.S. Pat. No. 5,578,832; EP 728 520; U.S. Pat. No. 5,599,695; EP 721 016; U.S. Pat. No. 5,556,752; WO 95/22058; and U.S. Pat. No. 5,631,734.

The probes utilized in the arrays can be of varying types and can include, for example, antibodies, including antibody fragments or peptidomimetics; synthesized probes of relatively short length (e.g., a 20-mer or a 25-mer), cDNA (full length or fragments of gene), amplified DNA, fragments of DNA (generated by restriction enzymes, for example), reverse transcribed DNA, peptides, proteins, and the like. Arrays can be utilized in detecting differential expression levels.

Common physical substrates for making protein arrays include glass or silicon slides, magnetic particles or other micro beads, functionalized with aldehyde or other chemical groups to help immobilize proteins. The substrate can also be coated with PLL, nitrocellulose, PVDF membranes or modified with specific chemical reagents to adsorb capture agents. The desirable properties of an ideal surface include: chemical stability before, during, and after the coupling procedure, suitability for a wide range of capture agents (e.g., hydrophilic and hydrophobic, low MW and high MW), minimal non-specific binding, low or no intrinsic background in detection, presentation of the capture agents in a fully-functional orientation, production of spots with predictable and regular morphology (shape, signal uniformity).

The variables in the immobilization of proteins include: type of capture agent, nature of surface (including any pretreatment prior to use), and the immobilization method. Both adsorption and covalent attachment have been used for protein arrays. Orientation of the capture agent is very important in presenting it to the ligand or the surface in a functional state. Although covalent attachment using a variety of chemically activated surfaces (e.g., aldehyde, amino, epoxy) as well as attachment by specific biomolecular interactions (e.g., biotin-streptavidin) provide a stable linkage and good reproducibility, chemical derivatization of the surface may alter the biological activity of the capture agent and/or may result in multi-site attachment.

In one embodiment, arrays are made with a non-contact deposition printer. The printer uses thermal ink jet heads that can print many solutions simultaneously to produce hundreds of spots of 50-60 μm diameter with a spacing of 150 μm between spots. The droplet volume ranges between 35 pL to 1.5 nL. The heating element is made out of TaAl or other suitable materials, and is capable of achieving temperatures that can vaporize a sufficient volume of printing buffer to produce a bubble that will push out a precise volume of the antibody solution on the substrate. Selection of printing buffer is important, in that the buffer accomplishes the following: increases printing efficiency (measure of the number of spots that are printed to the total number of spots that are attempted), reduces sample spreading, promotes uniform delivery, stabilizes the capture agents that are being printed, reduces sample drying, increases the visibility of the printed spots. In addition to the printing buffer, other variables that affect printing include: size of the drops, the method of washing and drying the print head, and the speed at which the dispensing head moves. Various modifications may be within these conditions.

Both direct labeling and sandwich format approaches may find use. In the direct labeling procedure, the antibody array is interrogated with serum samples that had been derivatized with a fluorescent label, e.g. Cy3, Cy5 dye, etc. In the sandwich assay procedure, unlabeled serum is first incubated with the array to allow target proteins to be captured by immobilized capture antibodies. Next, the captured target proteins are detected by the application of a labeled detection antibody. The sandwich assay provides extra specificity and sensitivity needed to detect pg/mL concentrations of cytokines, without compromising the binding affinities of the target protein through a direct labeling procedure.

Fluorescence intensity can be determined by, for example, a scanning confocal microscope in photon counting mode. Appropriate scanning devices are described by e.g., U.S. Pat. No. 5,578,832 to Trulson et al., and U.S. Pat. No. 5,631,734 to Stern et al. and are available from Affymetrix, Inc., under the GeneChip™ label. Some types of label provide a signal that can be amplified by enzymatic methods (see Broude, et al., *Proc. Natl. Acad. Sci. U.S.A.* 91, 3072-3076 (1994)). A variety of other labels are also suitable including, for example, radioisotopes, chromophores, magnetic particles and electron dense particles.

Those locations on the probe array that are bound to sample are detected using a reader, such as described by U.S. Pat. No. 5,143,854, WO 90/15070, and U.S. Pat. No. 5,578,832. For customized arrays, the hybridization pattern can then be analyzed to determine the presence and/or relative amounts or absolute amounts of known species in samples being analyzed as described in e.g., WO 97/10365.

Other methodologies also find use. In some embodiments, a solution based methodology utilizes capillary electrophoresis (CE) and microfluidic CE platforms for detecting and quantitating protein-protein interactions, including antibody reactions with proteins associated with lymphedema. This technique can be performed easily by any laboratory with access to a standard CE DNA sequencing apparatus. With this methodology, a fluorescent marker (eTag reporter) is targeted to the analyte with one antibody, and a second sandwich antibody of different epitope specificity that is chemically coupled to a "molecular scissors" induces release of the fluorescent probe when both antibodies are in close apposition on the specific analyte. Quantitation then is focused on the liberated eTag, that is quantified with a standard DNA capillary sequencing device. The eTag Assay System can be used to measure the abundance of multiple proteins simultaneously. A critical feature of the assay is that the affinity agents (antibodies) are not immobilized on surfaces, as is required with array technologies. Solution-based binding eliminates surface-induced denaturation and non-specific binding, and improves sensitivity and reaction kinetics.

By combining different colors in the eTag reporters, both mobility and color may be used to dramatically increase the degree of multiplexing. Many binding reactions can be multiplexed in the same vessel, followed by CE to identify the released eTag reporters. Each released eTag reporter encodes the identity of the probe to which it was originally attached. As a result, it is straightforward to configure multiplexed assays to monitor various types of molecular recognition events, especially protein-protein binding.

Diagnostic Algorithms

An algorithm that combines the results of multiple gene expression level determinations, e.g. an expression profile or expression score, may be used to discriminate between individuals with lymphedema and those without, even at early stages of the disease. In order to identify profiles that are indicative of a lymphedematous disease state, a statistical test will provide a confidence level for a change in the markers between the test and control profiles to be considered significant. The raw data may be initially analyzed by measuring the values for each marker, usually in triplicate or in multiple triplicates.

A test dataset is considered to be different than the normal control if at least one, usually at least two, at least 5, at least 10 or more of the parameter values of the profile exceeds the limits that correspond to a predefined level of significance.

To provide significance ordering, the false discovery rate (FDR) may be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher at al. (2001) PNAS 98, 5116-21, herein incorporated by reference). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using, this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data may be subjected to non-supervised hierarchical clustering to reveal relationships among profiles. For example, hierarchical clustering may be performed, where the Pearson correlation is employed as the clustering metric. One approach is to consider a patient lymphedema dataset as a "learning sample" in a problem of "supervised learning". CART is a standard in applications to medicine (Singer (1999) Recursive Partitioning in the Health Sciences, Springer), which may be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

This approach has led to what is termed FlexTree (Huang (2004) PNAS 101:10529-10534). FlexTree has performed very well in simulations and when applied to SNP and other forms of data. Software automating FlexTree has been developed. Alternatively LARTree or LART may be used Fortunately, recent efforts have led to the development of such an approach, termed LARTree (or simply LART) Turnbull (2005) Classification Trees with Subset Analysis Selection by the Lasso, Stanford University. The name reflects binary trees, as in CART and FlexTree; the lasso, as has been noted; and the implementation of the lasso through what is termed LARS by Efron et al. (2004) Annals of Statistics 32:407-451. See, also, Huang et al. (2004) Tree-structured supervised learning and the genetics of hypertension. Proc Natl Acad Sci USA. 101(29):10529-34.

Other methods of analysis that may be used include logic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as PAM software and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome.

These tools and methods will be applied to several classification problems. Algorithms are developed from the following comparisons: i) all cases versus all controls, ii) all cases versus low calcium controls, iii) MI cases versus angina cases, iv) low calcium controls versus high calcium controls.

In a second analytical approach, variables chosen in the cross-sectional analysis are separately employed as predictors. Given the specific ASCVD outcome, the random lengths of time each patient will be observed, and selection of proteomic and other features, a parametric approach to analyzing survival may be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition the Cox models may be used, especially since reductions of numbers of covariates to manageable size with the lasso will significantly simplify the analysis, allowing the possibility of an entirely nonparametric approach to survival.

These statistical tools are applicable to all manner of proteomic or genetic data. A set of biomarker, clinical and genetic data that can be easily determined, and that is highly informative regarding detection of individuals with clinically significant lymphedema or risk of lymphedema is provided.

Imaging In Vivo

In some embodiments, the methods are adapted for imaging use in vivo, e.g., to locate or identify sites where lymphedema associated genes are expressed. In these embodiments, a detectably-labeled moiety, e.g., an antibody, which is specific for the lymphedema associated polypeptide is administered to an individual (e.g., by injection), and labeled cells are located using standard imaging techniques, including, but not limited to, magnetic resonance imaging, computed tomography scanning, and the like.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention. Another important factor in selecting a radionuclide for in vivo diagnosis is that its half-life be long enough that it is still detectable at the time of maximum uptake by the target tissue, but short enough that deleterious radiation of the host is minimized. A currently used method for labeling with $^{99m}$Tc is the reduction of pertechnetate ion in the presence of a chelating precursor to form the labile $^{99m}$Tc-precursor complex, which, in turn, reacts with the metal binding group of a bifunctionally modified chemotactic peptide to form a $^{99m}$Tc-chemotactic peptide conjugate.

The detectably labeled antibody is used in conjunction with imaging techniques, in order to analyze the expression of the target. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body. Among the most commonly used positron-emitting nuclides in PET are included $^{11}$C, $^{13}$N, $^{15}$O, and $^{18}$F. Isotopes that decay by electron capture and/or γ emission are used in SPECT, and include $^{123}$I and $^{99m}$Tc.

Time Course Analyses

Certain prognostic methods of assessing a patient's risk of lymphedema involve monitoring expression levels for a patient susceptible to lymphedema, to track whether there is a change in expression of a lymphedema associated gene or panel of genes over time. An increase in expression over time can indicate that the individual is at increased risk for lymphedema. As with other measures, the expression level for the patient at risk for lymphedema is compared against a baseline value. The baseline in such analyses can be a prior value determined for the same individual or a statistical value (e.g., mean or average) determined for a control group (e.g., a population of individuals with no apparent neurological risk factors). An individual showing a statistically significant increase in lymphedema associated expression levels over time can prompt the individual's physician to take prophylactic measures to lessen the individual's potential for lymphedema, e.g. treatment with prophylactic therapies of the invention, such as immunosuppressive therapy, anti-inflammatory therapy, etc.

Therapeutic/Prophylactic Treatment Methods

Agents that modulate activity of lymphedema associated genes or pathways provide a point of therapeutic or prophylactic intervention. Therapeutic agents of interest for treatment of lymphedema include agents that directly modulate the expression of proteins that modulate inflammation, e.g. expression vectors, antisense specific for a proinflammatory gene. For example, expression of a gene of interest, e.g., TNFα, can be upregulated by introduction of an expression vector comprising the TNFα gene, providing molecules that mimic the activity of a protein, e.g. NF-κB, that promotes the expression of a target gene, etc.

Reciprocally, antisense molecules can be used to downregulate expression of target genes, e.g. proinflammatory genes, e.g. COX1, COX2, prostaglandin, in cells. The antisense reagent may be antisense oligonucleotides (ODN), particularly synthetic ODN having chemical modifications from native nucleic acids, or nucleic acid constructs that express such antisense molecules as RNA. The antisense sequence is complementary to the mRNA of the targeted gene, and inhibits its expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

In some instances, RNAi technology is used. As used herein, RNAi technology refers to a process in which double-stranded RNA, either as siRNA or shRNA, is introduced into cells expressing a candidate gene to inhibit expression of the candidate gene, i.e., to "silence" its expression. The dsRNA is selected to have substantial identity with the candidate gene. In general such methods initially involve transcribing a nucleic acids containing all or part of a candidate gene into single- or double-stranded RNA. Sense and anti-sense RNA strands are allowed to anneal under appropriate conditions to form dsRNA. The resulting dsRNA is introduced into cells via various methods. Usually the dsRNA consists of two separate complementary RNA strands. However, in some instances, the dsRNA may be formed by a single strand of RNA that is self-complementary, such that the strand loops back upon itself to form a hairpin loop. Regardless of form, RNA duplex formation can occur inside or outside of a cell.

A number of options can be utilized to deliver the dsRNA into a cell or population of cells. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

Other therapeutic agents of interest for treatment of lymphedema include agents that modulate the activity of a protein of interest e.g. small organic molecules or specific antibodies and analogs thereof that promote a protein activity, e.g. of TNFα, or that inhibit a protein activity, e.g. of proinflammatory proteins such as COX2, COX2, prostaglandins and the like, etc.

Agents of interest that modulate protein activity include, but are not limited to, HMG-Co A reductase inhibitors, e.g. statins, including I atorvastatin, cerivastatin, fluvastatin, lovastatin, pravastatin, simvastatin, etc., angiotensin converting enzyme inhibitors, salicylates, nonsteroidal anti-inflammatory prostaglandin inhibitors (COX-nonspecific and COX-2 specific), p38MAPK inhibitors, and NFκB antagonists. By way of example and not limitation, NSAIDs useful in the practice of the invention include fenoprofen calcium, nalfon, flurbiprofen, Ansaid, ibuprofen, ketoprofen, naproxen, anaprox, aflaxen, oxaprozin, diclofenac sodium, diclofenac potassium, cataflam, etodolac, indomethacin, ketorolac tromethamine, nabumetone, sulindac, tolmetin sodium, fenamates, meclofenamate sodium, mefenamic acid, piroxicam, salicylic acid, diflunisal, aspirin, oxyphenbutazone, and phenylbutazone.

Other therapeutic agents include: RhoKinase inhibitors, e.g. fasudil at a concentration of from about 0.1 to 100 mg/kg; TxA2 inhibitors, 5/15/12-LO inhibitors, LTB4 inhibitors; FLAP inhibitors, e.g. MK886 (Calbiochem) at a dose of from about 1 to 100 mg/kg; PAF-receptor inhibitor, PPARα agonists; PPARγ/δ antagonists, e.g. pioglitazone at a concentration of from about 0.1 to 100 mg/kg; STAT 5 inhibitors, JAK3 inhibitors, VLA4 antagonist, VCAM1 antagonist, chemokine antagonists, chemokine receptor blockers, PGI agonists, cathepsin inhibitors, PDE4i, and annexin inhibitors/agonist.

Therapeutic agents of interest also include derivatives of the aforementioned agents. In some instances, derivativization improves therapeutic efficacy, by, for example, increasing the stability and bioavailability of a compound. Examples of derivatives include the addition of methyl groups, ethyl groups, or isopropyl groups. Such derivativization may improve bioavailability and therapeutic efficacy by 2-fold or more, 3-fold or more, 4-fold or more, sometimes 5-fold or more, 10 fold or more, 15-fold or more, or 20-fold or more, e.g. 25-fold or more, 50-fold or more.

Therapeutic agents will have the effect of reducing, or decreasing, the volume of lymphedemous tissue. In some instances, volume is decreased 2-fold or more after treatment, i.e. as compared to the volume before treatment, for example, 2-fold or more, 3-fold or more, 4-fold or more, sometimes 5-fold or more, 10-fold or more, 15-fold or more, in some instances 20-fold or more, 50 fold- or more, etc. In other words, the volume is decreased by about 50 milliliters or more, 100 milliliters or more, 200 milliliters or more, 300 milliliters or more, 400 milliliters or more, 500 milliliters or more. In some instances, the volume is restored to normal volume, i.e. the volume prior to the onset of the lymphedema, e.g. the volume of the unaffected bilateral tissue. Volume can be measured by any of a number of methods in the art, e.g. circumferential measurements, water displacement volumetry, etc.

Therapeutic agents will also have the effect of restoring the architecture of the tissue, i.e. skin, to its condition pre-lymphedema. In other words, the architecture of the affected tissue will resemble the architecture of normal, unaffected tissue. Most notably, the dermis and subdermis return to a normal thickness, and eosinophils and lymphademic deposits are absent. See, for example, Example 5 below. The architecture of the tissue may be assayed by any convenient means, e.g. biopsy.

Therapeutic agents will also affect the gene expression profile of lymphedema datasets as described herein. For example, therapeutic agents will reduce the expression levels of lymphedema-associated genes that are upregulated in lymphedemous conditions. Such indicia may be decreased by at least 10%, by at least 20%, by at least 30%, by at least 50%, by at least 75%, by at least 90% or more by the methods of treatment provided herein. The lymphedema datasets may be measured as described herein or as known in the art.

Therapeutic agents can serve as the active ingredient in pharmaceutical compositions formulated for the treatment of lymphedema, including a propensity for lymphedema. The compositions can also include various other agents to enhance delivery and efficacy. The compositions can also include various agents to enhance delivery and stability of the active ingredients.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, and intrathecal methods.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations suitable for enteral administration, such as, for example, administration topically (e.g., as solutions, lotions, creams, paste, emulsions, suspensions, etc.), orally, rectally, vaginally, or by inhalation, include capsules, liquid solutions, emulsions, suspensions, and elixirs. For example, if prepared for topical applications, the compositions may comprise a biocompatible organic solvent, e.g. an isopropyl ester such as isopropyl myristate and isopropyl palmitate; a polar lipid, e.g. lecithin, phosphatidylcholine, etc., a surfactant, e.g. docusate sodium, docusate sodium benzoate, docusate calcium, tween 80, polysorbate 80; water; and/or urea (present at a concentration of about 5 to 20% by mass of the final composition). In some instances, a topical formulation will comprise an enhancer for skin penetration, such as SEPA 09. Examples of topical formulations may be found in, e.g. U.S. Pat. No. 5,654,337, U.S. Pat. No. 5,093,133, U.S. Pat. No. 5,210,099, U.S. Pat. No. 3,957,971, U.S. Pat. No. 5,016,652, the complete disclosures of which are incorporated herein by reference.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions Compound Screening Compound screening may be performed using an in vitro model, a genetically altered cell or animal, the bioluminescent animal model described herein, or purified protein corresponding to any one of the provided lymphedema associated genes. One can identify ligands or substrates that bind to, inhibit, modulate or mimic the action of the encoded polypeptide.

The polypeptides include those encoded by the provided genetic sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues that are not necessary for function. Variants can be designed so as to retain or have enhanced biological activity of a particular region of the protein (e.g., a functional domain and/or, where the polypeptide is a member of a protein family, a region associated with a consensus sequence). Variants also include fragments of the polypeptides disclosed herein, particularly biologically active fragments and/or fragments corresponding to functional domains. Fragments of interest will typically be at least about 10 aa to at least about 15 aa in length, usually at least about 50 aa in length, and can be as long as 300 aa in length or longer, but will usually not exceed about 500 aa in length, where the fragment will have a contiguous stretch of amino acids that is identical to a polypeptide encoded by a lymphedema associated gene, or a homolog thereof.

Compound screening identifies agents that modulate function of the lymphedema associated gene. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. Knowledge of the 3-dimensional structure of the encoded protein, derived from crystallization of purified recombinant protein, could lead to the rational design of small drugs that specifically inhibit activity. These drugs may be directed at specific domains.

The term "agent" as used herein describes any molecule, e.g. protein or pharmaceutical, with the capability of altering or mimicking the physiological function of a lymphedema associated gene. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Preliminary screens can be conducted by screening for compounds capable of interfering in a lymphedema pathway. The binding assays usually involve contacting a protein with one or more test compounds and allowing sufficient time for the protein and test compounds to form a binding complex. Any binding complexes formed can be detected using any of a number of established analytical techniques. Protein binding assays include, but are not limited to, methods that measure co-precipitation, co-migration on non-denaturing SDS-polyacrylamide gels, and co-migration on Western blots. The protein utilized in such assays can be naturally expressed, cloned or synthesized.

Compounds that are initially identified by virtue of acting in a lymphedema pathway or by any of the foregoing screening methods can be tested to validate the apparent activity. The basic format of such methods involves administering a lead compound identified during an initial screen to an animal that serves as a model for humans and then determining the effect on, for example, immunocyte trafficking. The animal models utilized in validation studies generally are mammals. Specific examples of suitable animals include, but are not limited to, primates, mice, and rats.

Active test agents identified by the screening methods described herein can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Once analogs have been prepared, they can be screened using the methods disclosed herein to identify those analogs that exhibit an increased ability to modulate gene product activity. Such compounds can then be subjected to further analysis to identify those compounds that appear to have the greatest potential as pharmaceutical agents. Alternatively, analogs shown to have activity through the screening methods can serve as lead compounds in the preparation of still further analogs, which can be screened by the methods described herein. The cycle of screening, synthesizing analogs and re-screening can be repeated multiple times.

Compounds identified by the screening methods described above and analogs thereof can serve as the active ingredient in pharmaceutical compositions formulated for the treatment of various disorders, including a propensity for lymphedema, as discussed above.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Transcriptional profiling has been utilized in the molecular characterization of isolated lymphatic endothelia but the molecular end-organ response to lymph stagnation remains un-addressed and poorly understood. An elucidation of whole tissue response to disease can provide insights into the important interactions between the tissue matrix and the resident, heterogeneous cellular populations that comprise the target-organ response to persistent lymph stagnation.

To investigate the tissue responses to lymphatic vascular insufficiency, we have therefore undertaken dynamic, in vivo imaging of the impaired immune traffic in a murine model of acquired lymphatic insufficiency that simulates the lymphatic dysfunction of post-surgical lymphedema. These observations were correlated with an assessment of the cutaneous histopathology in the lymphedema tissue.

To investigate the molecular mechanisms of tissue response to lymphatic vascular insufficiency, a large scale transcriptional profiling of the lymphedema tissue was performed utilizing a comprehensive mouse cDNA microarray containing 42,300 features, representing over 25,000 unique genes and ESTs. The patterns of gene expression in lymphedema were contrasted with those observed in normal and surgical sham controls. Using rigorous statistical tools for analysis of the microarray data, we have identified patterns of cutaneous gene expression that correlate with the imaging and light microscopic abnormalities and, thus, distinguish the tissue responses to persistent disruption of lymphatic function in the skin.

These studies contribute to our understanding of the pathobiology of lymphedema, and provide insights into novel strategies for molecular therapies.

Materials and Methods

Creation of Experimental Lymphedema.

Post-surgical lymphedema was experimentally created in the tails of female hairless, immunocompetent SKH-1 mice (Charles River Laboratories, Boston Mass.). Prior to surgery, the mice were anesthetized with intraperitoneal injection of 0.07 cc of a solution containing ketamine, xylazine, and saline. For each intervention, the skin of the tail was circumferentially incised proximally, at a point 16 mm distal to its base. The major lymphatic trunks were identified through subcutaneous injection of methylene blue distal to the surgical incision, followed by controlled, limited cautery ablation of these structures. In surgical controls (sham animals), skin incision alone was performed, with methylene blue injection but without lymphatic cautery. The normal control animals did not undergo any surgical manipulation. All animal subjects were sacrificed on Day 14 of observation. After sacrifice, 0.5 gm sections of the tail were harvested for paraffin embedding and RNA extraction.

Tail Volume Quantitation.

Tail volume was quantitated in each animal subject immediately prior to sacrifice. Volumetric assessment was performed with a manually adjusted caliper, with serial measurement of the tail circumference at 5 mm intervals along its axis. The tail volume was quantitated with the truncated cone formula. Immediately following sacrifice, 0.5 gm sections of the tail were harvested for histological analysis and RNA extraction. Sections extended from a point 4 mm proximal to the surgical incision to 8 mm beyond it. For examination of the responses remote from the point of injury, sections were harvested 4 cm distal the surgical site. The specimens were fixed overnight in 4% paraformaldehyde. After paraffin embedding, 5 μm sections were stained with hematoxylin and eosin (H&E, Richard-Allan Scientific). For visualization of histiocytes/mast cells, the sections were stained with a 1% toluidine blue solution (LabChem, Inc.) diluted in 1% NaCl. After deparaffinization in xylene, sections were rehydrated though a series of graded alcohol steps starting with 100% EtOH and ending in 50% EtOH. Slides remained in toluidine blue for 2 minutes and were then dehydrated through graded alcohol washes and covered with Cytoseal (Richard Allan Scientific).

LYVE-1 Immunohistochemical Staining.

5 μm-thick paraffin sections were de-paraffinized in xylene, re-hydrated in a graded series of ethanol, pretreated with target retrieval solution (Dako, Carpinteria, Calif.) in a pressure cooker, and incubated in a peroxidase block for 10 minutes. Sections were then incubated with rabbit polyclonal anti-LYVE-1 antibody (1:200, Upstate Cell Signaling Solutions, Lake Placid, N.Y.) for 1 hour at room temperature, followed by horseradish peroxidase (HRP)-conjugated secondary antibody for 30 minutes at room temperature and detection with DAB for 4 minutes (Envision System Kit, Dako). Tissue sections were counterstained with Gill 1 Hematoxylin (Richard-Allan Scientific, Kalamazoo, Mich.). for 15 seconds, then dehydrated in graded ethanol and coverslipped with CoverSafe (American Master*Tech, Lodi, Calif.).

Functional Imaging of Immune Traffic in the Lymphedema Model.

Experimental lymphedema (LE) was created surgically in the tails of FVB/N female wild type mice (Jackson Laboratories, n=3), using the technique described above. Surgical sham controls (n=5) were also created and compared with normal mice (n=5). For in vivo bioluminescence imaging, spleens from transgenic luc+ heterozygous animals were put into single cell suspension, expressing firefly luciferase under the control of a chicken beta-actin promoter as previously described. The single cell suspensions from mouse spleens consisted of different hematopoietic lineages: ~40% were CD19+ B cells, ~20% CD4+ T cells, ~10-15% were CD8+ T cells, 3% NK1.1+ NK cells and the rest were GR.1+ granulocytes, Mac-1+ macrophages, CD11c+ dendritic cells and rarer cell populations. $4 \times 10^6$ splenocytes (>97% CD45+) in PBS were injected in a volume of 20 ml into the tail interstitium, 1 cm caudal to the site of surgery, in lymphedema mice and surgical shams, respectively. Normal mice were injected at the corresponding level of the tail. Injections were performed on post-surgical day 7. Thereafter, luc+ cells were repetitively imaged in vivo, at predetermined intervals following the cell injections. In brief, mice were anesthetized by intraperitoneal co-injection of a mixture of ketamine (1 mg/mouse), xylazine (100 μg/mouse) in PBS and the substrate luciferin (150 mg/kg). Ten minutes thereafter, dorsal images were obtained with an IVIS100 CCD-imaging system. The efficiency of cellular lymphatic drainage was determined by direct imaging of light emission at each of the measured time points, with quantitation of the relative change in light emission at 20 hours after cell injection, defined as 100%.

Microsphere Quantitation of Arterial Perfusion of the Mouse Tail.

The arterial perfusion of the mails of experimental and control mice was quantitated through intracardiac microsphere injection. After induction of general anesthesia, stable labeled 15 μm microspheres (STERispheres Gold, BioPAL, Worcester, Mass.) were injected into the left ventricle. Each animal subject received $0.5 \times 10^6$ microspheres (0.2 ml) injected directly into the left ventricle. The animals were sacrificed after 12 minutes. The tails were harvested and dried overnight at 70° C. The assay to quantitate disintegrations/minute (dpm) was performed by BioPhysics Assay Laboratory (Worcester, Mass.) as previously described.

Lymphoscintigraphy in Experimental Lymphedema

Whole body lymphoscintigraphy was performed after the intradermal injection of 100 μCi/0.02 ml of filtered $^{99m}$Tc-sulfur colloid (100 nm size) into the tip of the tail. Dynamic and static images (255×255) using a parallel hole collimator were acquired in a microSPECT gamma camera (Lumigem, Gamma Medica Inc.). The dynamic images (1000 frames; 0.5 s/frame) were started 60 sec prior to the injection of the tracer. The injection lasted for 20 sec. The static images (10 min) were acquired immediately after the dynamic acquisition.

Microarray Experimental Design, RNA Preparation and Hybridization

Tissues were derived from 9 mice for each of the three biological states under study (cutaneous specimens from normal, lymphedematous, and surgical sham animals, respectively) for a total of 27 mice. All microarray hybridizations were performed with three biological replicates, using pooled samples independently derived from 3 mice each, for a total of 9 hybridizations. After tissue was harvested for histological examination, the remaining, distal portion of the tail was retrieved for RNA isolation. After completely separating the tail skin from the cartilage by blunt dissection, the tissue was separated into segments of 0.5 mm for further processing. Total RNA was isolated using a modified two-step purification protocol as described 14. RNA integrity was assessed using the Agilent 2100 Bioanalyzer System with RNA 6000 Pico LabChip Kit (Agilent). First strand cDNA was synthesized from 15 μg of total RNA derived from each pool and from whole e17.5-day embryo for reference RNA, in the presence of Cy3 or Cy5 dUTP, respectively, and hybridized to the Mouse Transcriptome Microarray. A continuously updated and annotated list of the cDNAs included on this array is available at the Stanford Microarray Database.

Data Acquisition, Analysis, and Statistical Analysis

Image acquisition of the mouse cDNA microarrays was performed on an Agilent G2565AA Microarray Scanner System. Feature Extraction was performed with GenePix 4.0 software (Axon, Inc). Numerical raw data were migrated from GenePix, without processing, into an Oracle relational database (CoBi) that has been designed specifically for microarray data analysis (GeneData, Inc, USA). The data were then analyzed using Expressionist software (GeneData, Inc, USA). After background subtraction and dye normalization, features with low signal intensity in the reference channel were filtered if signal was less than 2.5× background value, retaining a total of 8353 features for further analysis. K-nearest-neighbor (KNN) algorithm was applied to impute for missing values (<7% of remaining data). For two-group comparisons, we used the significance analysis of microarrays (SAM) algorithm. Heatmaps were generated using HeatMap builder. For enrichment analysis we used the EASE analysis software, which uses within particular gene sets.

Quantitative Real-Time Reverse Transcriptase-Polymerase Chain Reaction

Quantitative rtPCR was performed as described. Primers and probes for 10 representative differentially expressed genes were obtained from Applied Biosystems Assays-on-Demand. cDNA was synthesized from 5 µg of total RNA using Taqman Reverse Transcription Reagents (Applied Biosystems), a set which includes MultiScribe™ Reverse Transcriptase, RNase Inhibitor, dNTP Mixture, Oligo $d(T)_{16}$, Random Hexamers, 10×RT Buffer, and $MgCl_2$ Solution. Amplification was performed in triplicate at 50° C. for 2 minutes and 95° C. for 10 minutes followed by 40 cycles of 95° C. for 15 seconds and 60° C. for 1 minute. Reactions without template and/or enzyme were used as negative controls. 18S ribosomal RNA was used as an internal control. A standard curve derived from e17.5 day mouse embryonic RNA was plotted for each target gene by linear regression using SPSS version 11.0 software (Applied Biosystems). RNA quantity was expressed relative to the corresponding 18S control. Fold differences were calculated by dividing the experimental results by the pooled normal results and plotted on a log 10 scale. The primers and probes utilized in this study are listed in Table 1.

Results

Murine Model of Acute Experimental Lymphedema: Tail Volume Quantification

Forty-five 3-week-old SKH-1 hairless mice were studied in this investigation. Of these, 18 underwent post-surgical lymphatic ablation, 9 served as surgical sham controls, and the remaining 18 served as normal controls. Tail volume for each group of animals is depicted in FIG. 1. At post-surgical Day 7, the lymphedema tail volumes were 200±50% of baseline (P<0.008 when compared to surgical sham controls). In the animals subjected to lymphatic ablation, the edematous enlargement of the tails persisted until the day of sacrifice (Day 14). Of note is the fact that cutaneous healing of the wound, both in the lymphedematous and surgical sham subjects, was complete by Day 14. There was no statistically significant change in tail volume in either surgical sham or normal controls.

Histological Assessment of the Cutaneous Response to Lymphatic Interruption

Figure 2:
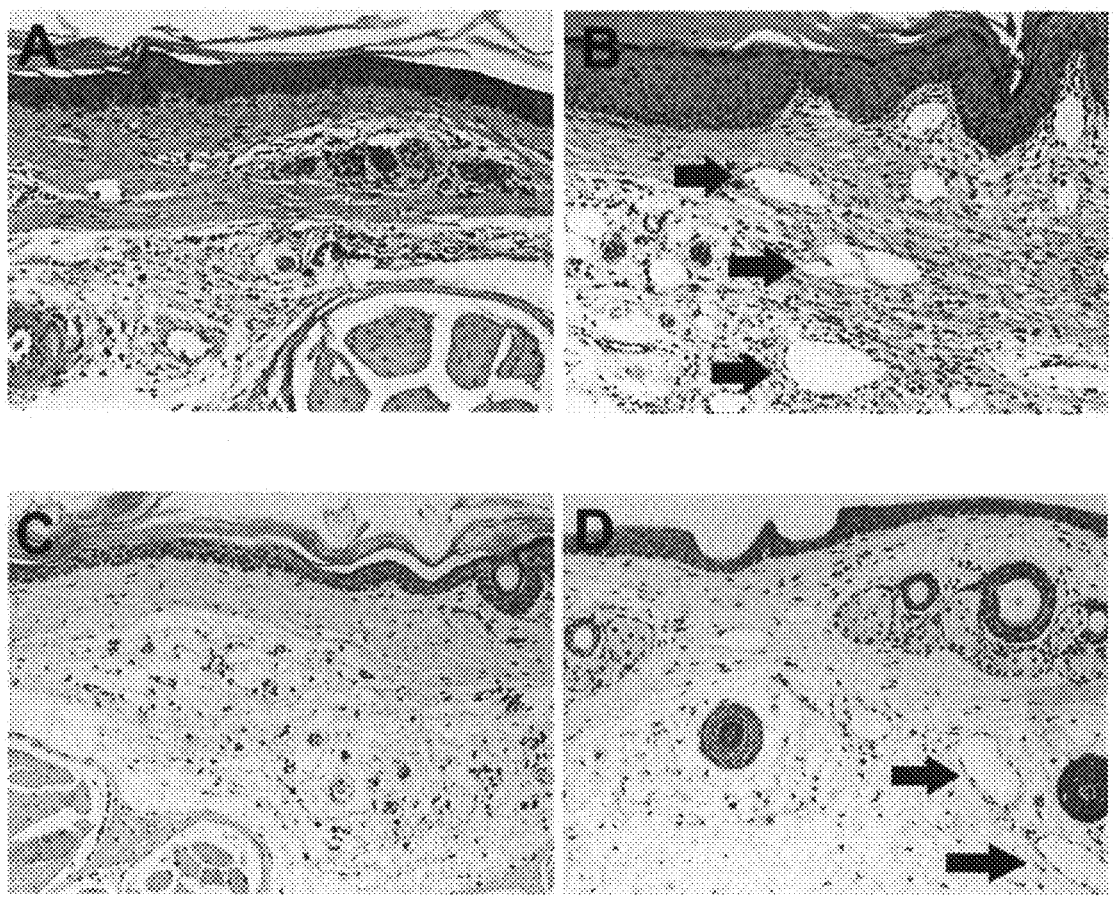
FIG. 2. Histopathology of experimental lymphedema in the murine tail. Lymphedema was characterized by the presence of marked acute inflammatory changes, both adjacent to the surgical site and within distal regions of the tail, remote from the site of surgical ablation. A. Normal tail skin, harvested 16 mm from the base of the tail. These specimens are characterized by the presence of a thin dermis and epidermis, with a normal epidermal/dermal junction. Surgical sham controls were indistinguishable from normals, with no increased cellularity in dermis or epidermis, and no enlarged nuclei or hyperkeratosis. B. Lymphedematous skin, harvested immediately distal to the site of prior surgical lymphatic ablation is characterized by the presence of marked acute inflammatory changes, absent in the tissue derived from the normal tails. There is a notable increase in cellularity, with an increase in the number of observed fibroblasts and histiocytes, as well as a large infiltration of neutrophils. There is hyperkeratosis and spongiosis and edema of the epidermis, with irregularity of the epidermal/dermal junction, elongation of the dermal papillae, and a 2-3× expansion of tissue between the bone and the epidermis. There are numerous dilated lymphatics in the dermis and subdermis (block arrows). In contrast, normal tail sections were devoid of these dilated structures. C. Normal skin derived from the distal tail. No inflammation, hypercellularity or lymphatic dilatation is observed. D. Distal skin in lymphedema. Spongiosis and lymphatic microvascular dilatation (block arrows) are once again detectable.

H&E specimens derived from the lymphedematous tails were characterized by the presence of marked acute inflammatory changes (FIG. 2B), when compared to the tissue derived from the normal tails (FIG. 2A). There was a notable increase in cellularity, with an increase in the number of observed fibroblasts and histiocytes, as well as a large infiltration of neutrophils Granulation tissue was observed closer to the center of the section, with bystander destruction of muscle tissue. In addition, there was hyperkeratosis and spongiosis and edema of the epidermis, with irregularity of the epidermal/dermal junction, elongation of the dermal papillae, and a 2-3× expansion of tissue between the bone and the epidermis. Lymphedema specimens were characterized by the presence of numerous dilated lymphatics in the dermis and subdermis, as seen in FIG. 2B. In contrast, normal tail sections were devoid of these dilated structures. The normal tissues were characterized by the presence of a thin dermis and epidermis, with a normal epidermal/dermal junction (FIG. 2A). The surgical sham controls were indistinguishable from normals, with no increased cellularity in dermis or epidermis, and no enlarged nuclei or hyperkeratosis.

In order to assess whether the lymphedematous changes created a uniform pathological response distal to the point of lymphatic ablation, the tissues were also sampled distally (4 cm distal to the point of surgical incision) in normal (FIG. 2C) and lymphedematous (FIG. 2D) tails. The observed changes were comparable to those observed adjacent to the surgical site: lymphedematous tissues were characterized by hypercellularity, inflammatory infiltration, and microlymphatic dilatation that were not present in the normal tissues.

Quantitative Assessment of Arterial Perfusion of the Murine Tail Lymphedema Model While we have taken great care to avoid concurrent injury to adjacent vascular structures during surgical lymphatic ablation, we have undertaken an evaluation to exclude inadvertent arterial injury during surgery. The mouse tails remained grossly stable throughout the post-surgical observation phase, with no evidence of frank necrosis distal to the surgical site. In order to further substantiate the absence of an arterial ischemic contribution to the histological pathology observed in lymphedema, quantatitative assessment of arterial perfusion was performed through intracardiac injection of stable 15 µm microspheres into the left ventricles of normal (n=3) and lymphedema (n=3) mice. Perfusion of the tail, measured in disintegrations/minute (dpm), did not differ statistically between the two categories (normal, 151186±69213 dpm; sham, 95581±48003 dpm, N.S.), confirming preservation of arterial supply in the lymphedema animals.

LYVE-1 Immunohistochemical Staining

Figure 3:
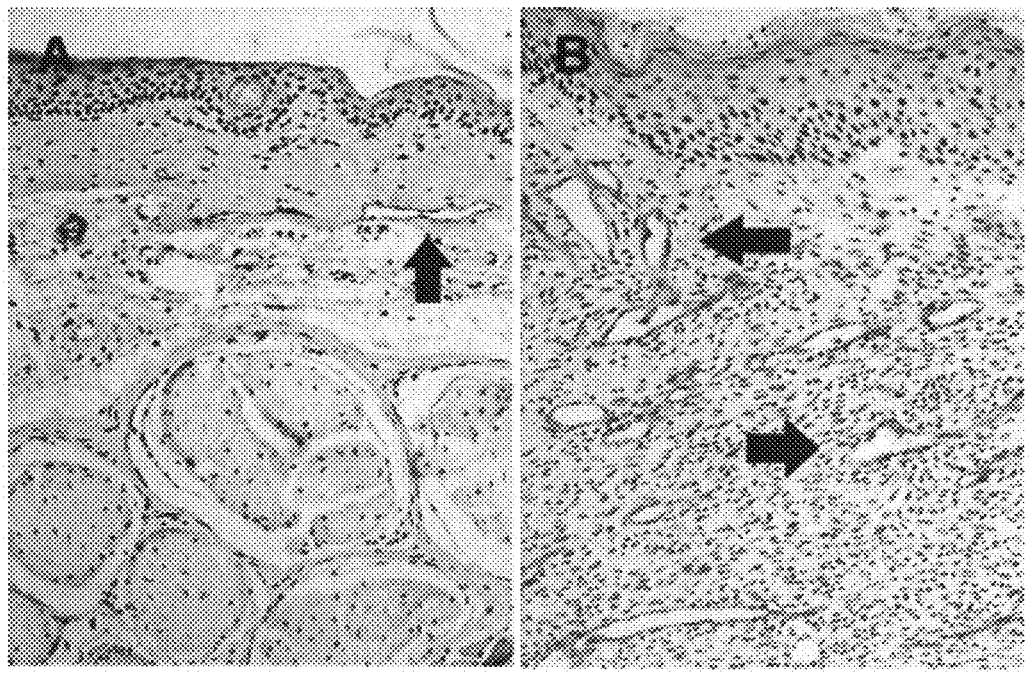
FIG. 3. LYVE-1 Immunohistochemical Staining. Immunohistochemical staining for LYVE-1 is depicted in surgical sham controls (A) and in lymphedema (B) [block arrows]. The lymphedema response is characterized by the presence of numerous dilated microlymphatic structures in the dermis and subdermis. Lymphedema produces a statistically significant increase in average cross-sectional vessel area.

The nature of the lymphatic vascular response distal to the anatomic surgical ablation was assessed with quantitative assessment of lymphatic vessel number and size by immunohistochemical staining for LYVE-1 (FIG. 3). As observed in the H&E sections, lymphedema was characterized by the presence of numerous dilated microlymphatic structures in the dermis and subdermis. Mean lymphatic vessel number was determined by averaging the number of total lymphatic vessels in all the fields of each slide at 10× magnification. Single brown-stained endothelial cells with a lumen were counted as individual lymphatic vessels. Quantitation was performed normals (n=3), surgical shams (n=3), and lymphedema tails (n=3), respectively. Lymphedema was characterized by an increase in LYVE-1-positive vessel number/field that was not observed in shams: lymphedema, 7.0±4.8; sham, 0.6±0.5; and normal, 1.2±0.8.

Vessel area was quantitated according to the formula $\pi \cdot r_1 \cdot r_2$. The average lymphatic luminal area/field was 503±158 µm² in normals, 436±345 µm² in shams, and 51344±18688 µm² in lymphedema. Normals and shams did not differ statistically, but the lymphedema group displayed a statistically significant increase in average vessel area when compared either to normals or to sham surgical animals (p=0.009 for each comparison). Thus, in summary, the experimental lymphedema is accompanied by an increase in vessel number but, even more notably, by an increase in lymphatic vascular cross-sectional area.

Lymphoscintigraphy of Experimental Lymphedema

Whole body lymphoscintigraphy was performed in normal (n=4) and lymphedema (n=4) mice. All non-operated mice showed lymphatic drainage from the tip of the tail through two lumbar lymph nodes, asymmetric para-aortic nodes and mediastinal nodes, with final visualization of the liver. The lymphatic flow speed in basal conditions was estimated to be 0.9±0.66 mm/s. In the lymphedema animals, significant dermal backflow was present, but no flow was observed beyond the base of the tail. These lymphoscintigraphic findings closely simulate the qualitative changes to be observed in the analogous imaging of acquired human lymphedema.

Functional In Vivo Imaging of Immune Traffic

Figure 4A:
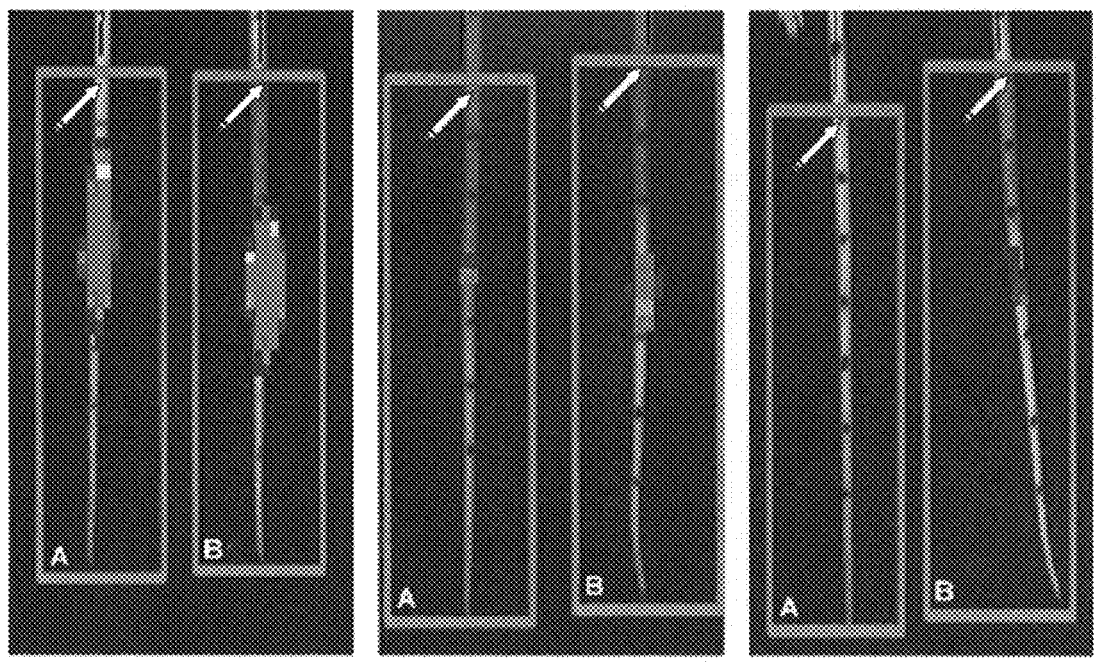
FIG. 4. In vivo bioluminescence imaging of immune traffic. (A) Bioluminescence imaging was performed at defined timepoints following the introduction of luc+ cells. This contains a representative series of imaging experiments for paired lymphedema and normal control mice. In general, clearance of bioluminescent immunocytes from the lymphedematous tails was delayed, but remained unimpaired in the surgical sham controls. In each panel, the normal tail (a) is seen to the left of the lymphedematous tail (b). Photon densities range from red (high) to blue (low). The left panel shows a perceptible increase in photon densities in lymphedema on Day 3 post-injection (postoperative Day 10). Within several days, the disparity in cellular clearance is even more evident (middle panel); as late as Day 17 post-injection, there is still visible bioluminescence in the lymphedematous tail, while all activity has cleared from the normal tail (right panel). The original surgical site is depicted by the white arrows. The black marks on the tail denote 8 mm vertical distances; splenocyte injection was performed 24 mm below the surgical site. (B) Quantitative assessment of in vivo bioluminescence imaging of immune traffic. Relative photon density, expressed as a of the observed value on Day 1, was significantly greater in lymphedema than in normal controls, both at Day 3 and at Day 7 post-injection (*, $P<0.05$; §, $P<0.02$).
Figure 4B:
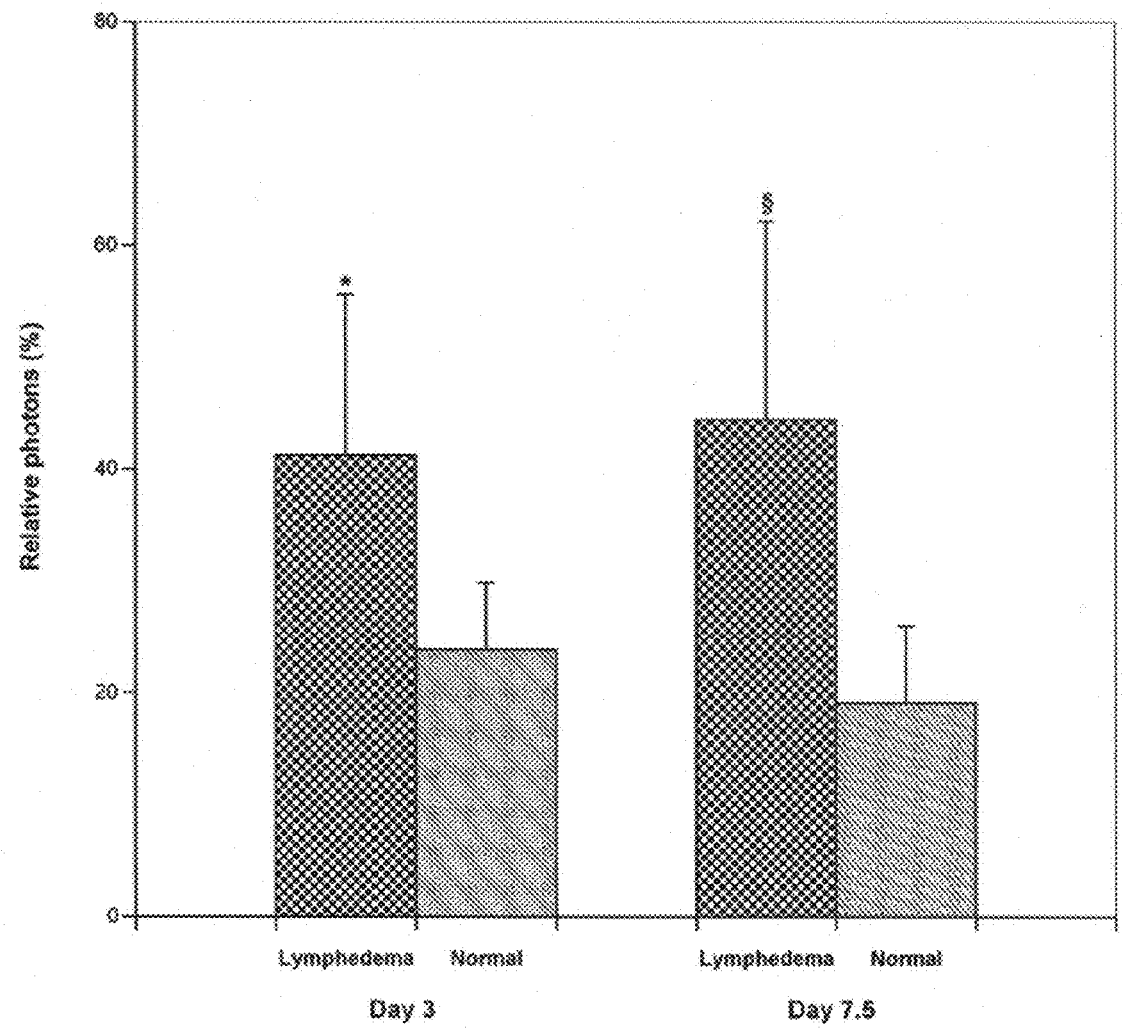

The lymphatic vasculature participates in the immune response through the continuous transportation of white blood cells and antigen-presenting cells. The constellation of histological observations in this model, otherwise unexplained by impaired interstitial fluid mobilization, suggests that derangements in lymphatic immune traffic might contribute, either actively and passively, or both, to the biology of lymph stagnation. Accordingly, we chose to corroborate histopathology with observed, quantifiable changes in immune traffic. Bioluminescence imaging (BLI) was performed on days 3, 5 and 7.5 following the introduction of luciferase (luc+) cells into the distal tail (corresponding to postoperative days 10, 12, and 17.5, respectively). In general, when compared to normals, the clearance of bioluminescent immunocytes was delayed in lymphedema, but remained unimpaired in the surgical sham controls. FIG. 4 depicts a series of imaging experiments for a representative pair of lymphedema and normal control mice. Relative photon density, expressed as a % of the observed value on day 1, was significantly greater in lymphedema than in the normals, both at day 3 and at day 7 post-injection (FIG. 4).

Figure 5:
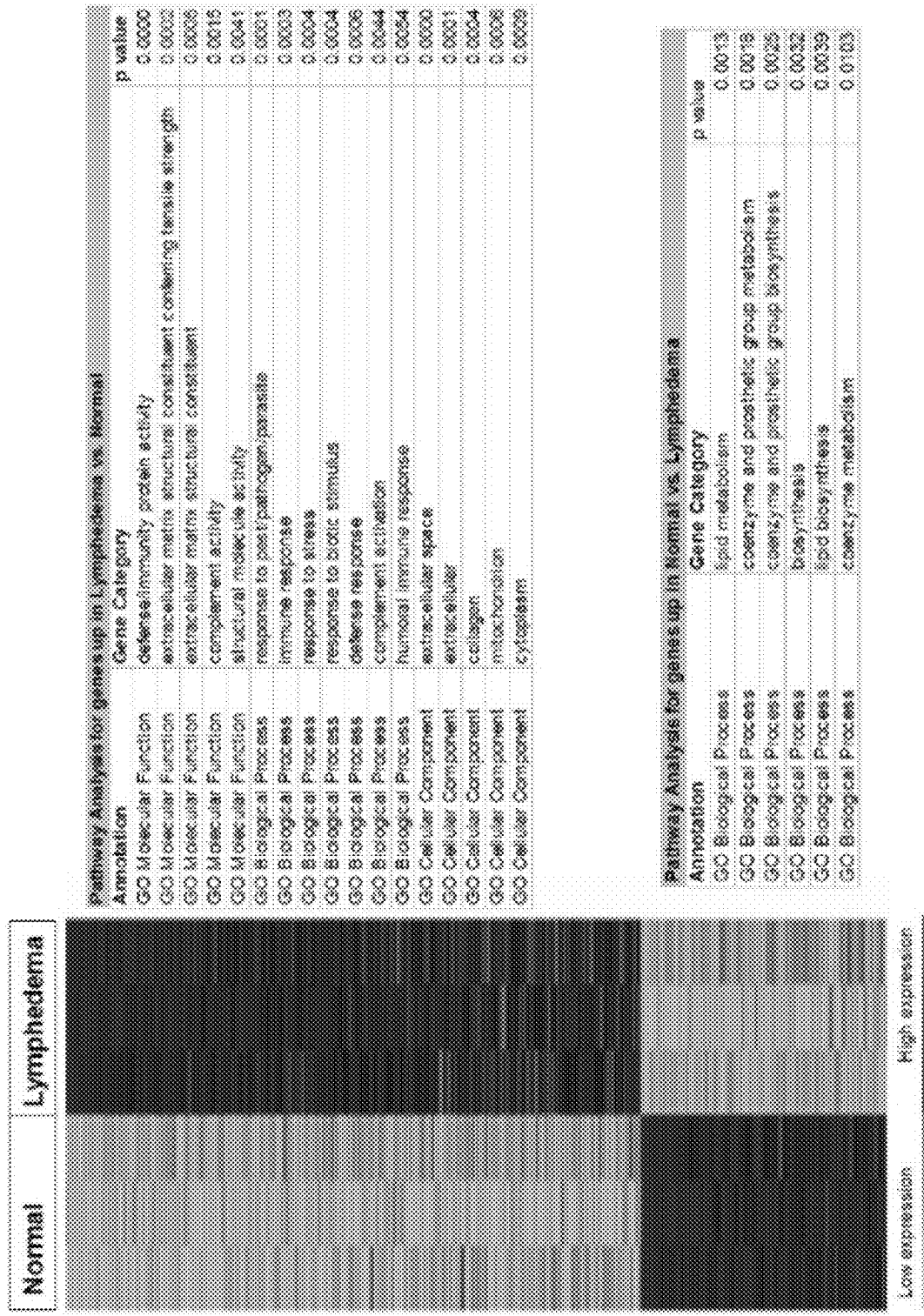
FIG. 5. SAM analysis of microarray data. At a false detection rate of 5%, SAM analysis identified 429 up-regulated genes in the lymphedema state versus 183 down-regulated genes in mice. There were no statistically significant differences between normal mice and surgical control animals (SAM, FDR<25%). Enrichment analysis with the Fisher's Exact Test (EASE software) demonstrated several statistically significant ontologies.

Large-Scale Analysis of Cutaneous Gene Expression in Response to Lymphatic Vascular Insufficiency (Lymph Stasis)

cDNA microarrays containing a large portion of the mouse transcriptome were used to study the repertoire of genes expressed in the murine skin structures. Triplicate microarray experiments were performed using pooled RNA from the tail skin of female SKH-1 hairless mice representing 3 biological states: normal, lymphedematous, and surgical sham. Our analyses demonstrated significantly different patterns of gene expression in normal skin and the skin derived from lymphedematous mice. Significance analysis of microarrays (SAM), at a false detection rate of 5%, identified 429 upregulated genes in the lymphedema state versus 183 down-regulated genes (FIG. 5). There were no statistically significant differences between normal mice and surgical control animals (SAM, false detection rate (FDR)<25%). A complete list of differentially regulated genes is provided in Table 2. To identify important biological themes represented by genes differentially expressed in the atherosclerotic lesions, we functionally annotated the genes using Gene Ontology (GO) terms. Enrichment analysis with the Fisher's Exact Test (EASE software) demonstrated several statistically significant ontologies (FIG. 5, Tables 3 and 4), including several pathways associated with inflammation. The inflammatory processes such as defense response, immune response, the response to stress, response to pest/pathogen/parasite, and complement activation represent both humoral immune response and innate immunity. Further scrutiny of the list of genes whose expression is significantly altered in lymphedematous skin suggests that the disease process can be characterized by alterations within a relatively small set of functional attributes, as summarized in Table 5. These processes include acute inflammatory response, wound healing and fibrosis, angiogenesis, cytoskeletal organization, Wnt pathway activation, and adipogenesis.

Figure 6:
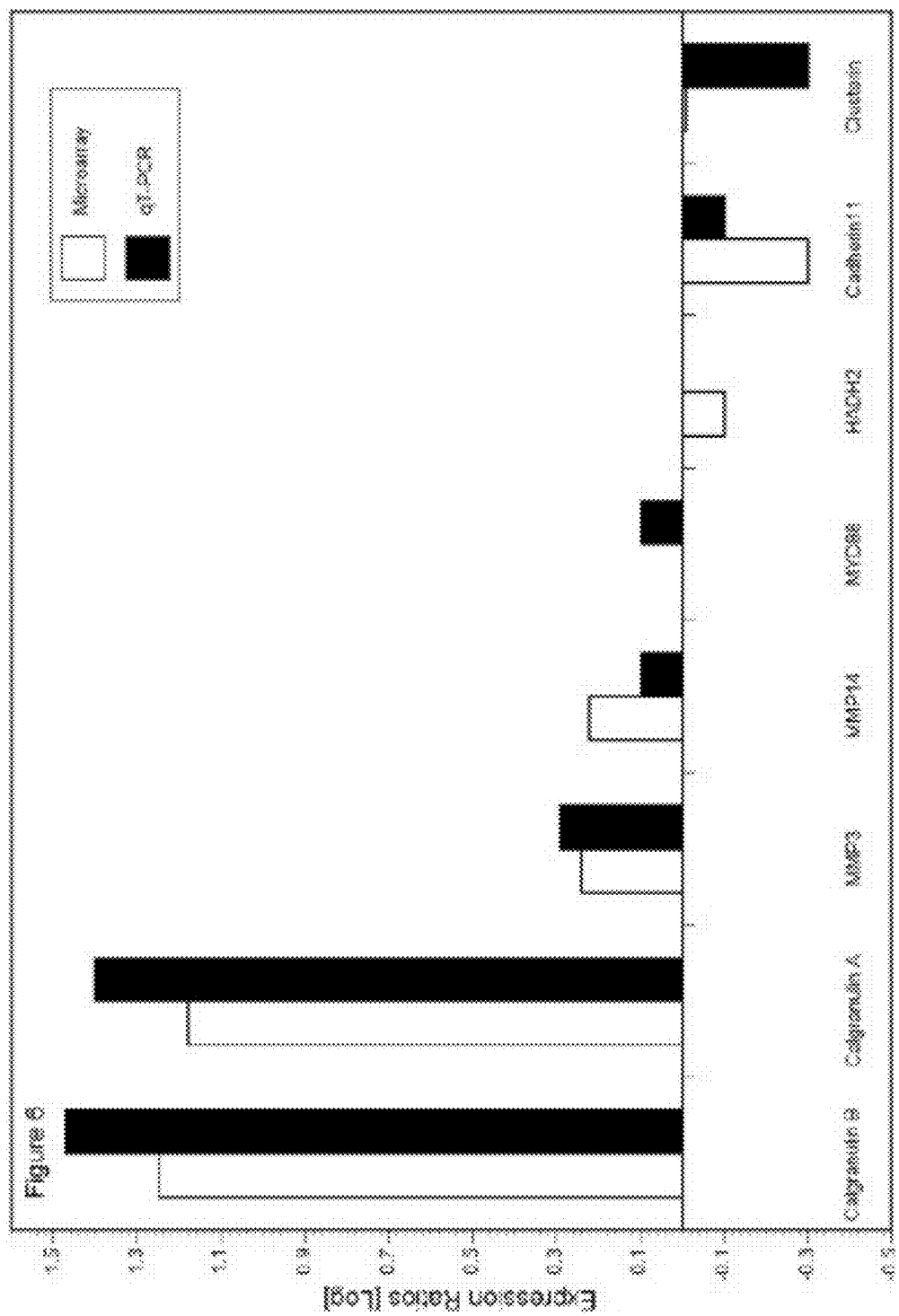
FIG. 6. Quantitative real-time RT-PCR confirmation of the results of microarray hybridization of mouse tissue. The graph represents fold-changes of expression in lymphedema in mice, relative to normal controls, for each of 8 representative genes, by microarray hybridization and qRT-PCR, respectively. For MYD88 by microarray, and HADH2 by qRT-PCR, respectively, the log [gene expression]=0. Abbreviations: MMP, matrix metalloproteinase; MYD88, myeloid differentiation primary response gene 88; HADH2, hydroxysteroid (17-beta) dehydrogenase 2.

Quantitative Real-Time RT-PCR Confirms the Accuracy of Microarray Hybridization Results Differential expression of 8 representative genes from various pathways was confirmed by quantitative real-time PCR (qRT-PCR). The genes were selected to represent the spectrum of magnitude and direction of change of lymphematous gene expression relative to normal. The genes assayed included calgranulins A and B, matrix metalloproteinases 3 and 14 (MMP3 and MMP14), myeloid differentiation primary response gene 88 (MYD88), hydroxysteroid (17-beta) dehydrogenase 2 (HADH2), cadherin 11, and clusterin. Overall, the results of the two methods correlated well (FIG. 6).

Discussion

In this study, we have characterized a mouse model of lymphedema using in vivo functional imaging modality and histopathological correlation. This model of acute, acquired lymph stagnation closely simulates the volume response, histopathology, and lymphoscintigraphic characteristics of human acquired lymphedema. LYVE-1 immunohistochemistry demonstrates that this acute impairment of lymph transport is accompanied by an increase in the number and size of microlymphatic structures in the lymphedematous cutaneous tissues.

We have also undertaken molecular characterization of the disease process through comprehensive transcriptional profiling of the murine lymphedematous tail skin. We have identified a set of genes and molecular pathways that play a role in the unique biology of this cutaneous response to lymph stasis (lymphedema). Recognition of this molecular response pattern is likely to enhance our comprehension of the pathogenesis and biology of lymphedema. The model has been elaborated to simulate the regional, acquired lymph stagnation that can arise after trauma, surgery and cancer therapeutics. Despite apparent rapid healing of the external cutaneous wound, the model features a stable, persistent, edematous increase in the volume of the tail, accompanied by a profound inflammatory response; neither edema nor inflammation is seen in surgical controls.

The cutaneous inflammatory response observed in this model replicates clinical descriptions of human acquired lymphedema, where there is frequently evidence of concomitant chronic inflammation, and regional immune responses are distorted. Architectural changes in the skin and subcutaneous tissues are often profound. Chronic lymph stasis typically stimulates an increase in the number of fibroblasts, adipocytes, and keratinocytes in the skin. Mononuclear cells (chiefly macrophages) often demarcate the chronic inflammatory response. In affected tissues, there is an increase in collagen deposition, accompanied by adipose and connective tissue overgrowth in the edematous regions.

In the current study, the molecular expression profile of lymphedema, observed in parallel with the histopathology and the dynamic immune traffic imaging, suggests that the deranged immune traffic plays a role in the pathogenesis of the disorder. In normal immune traffic, mononuclear phagocytes and lymphocytes from the tissues enter the afferent lymph vessels and the lymph nodes to elicit primary immune responses before reentering the vasculature. In chronic lymphedema, the impairment of lymphocyte and Langerhans cell trafficking from skin to regional lymph nodes leads to inefficient clearance of foreign antigens, and provides the substrate for chronic inflammatory changes.

Transcriptional profiling has been utilized to identify genes activated in disease states and to refine targets for molecular therapy. This approach is particularly attractive for the problem of acquired lymphedema, where the heterogeneous cellular composition of the tissues exposed to lymph stagnation presupposes a very complex, interdependent pattern of gene expression. While the characteristic expression profiles of isolated lymphatic endothelia have previously been studied, the current investigation represents the first in-depth molecular examination of the end-organ response to lymph stagnation. Despite the heterogeneous nature of the cellular material under investigation, the approach of high-throughput transcriptional profiling and statistical gene ontology analysis has disclosed discernable patterns of gene expression that are representative of the disorder under scrutiny.

Transcriptional profiling can provide not only a gene-by-gene view of physiological alterations in a diseased state, but also a statistically rigorous identification of the biological processes that are induced or repressed in disease. This provides a much broader and more comprehensive view of the disease process as a whole than does a simple gene list, making generation of hypotheses about mechanisms more informed. Based on Gene Ontology functional annotations for each gene on the array, we used Fisher's exact test statistical analysis to identify functional processes which are significantly induced and repressed in this disease model (Table 5). The results of this analysis illustrate that whole panels of genes involved in the immune response, stress response, and complement activation are induced in lymphedema when compared to controls.

Among the most interesting of the upregulated genes involved in these processes include many reflecting the inflammatory process. Calgranulin B, highly upregulated in this experimental model, belongs to a family of small calcium-binding proteins that are highly expressed in neutrophil and monocyte cytosol. These molecules are found at high levels in the extracellular milieu during inflammatory conditions 33. Calgranulins are potent stimulators of neutrophils and likely are involved in neutrophil migration to inflammatory sites. The levels of several of these proteins are markedly elevated in psoriasis, among other conditions. Tenascin C is strongly induced by various pro- and anti-inflammatory cytokines, and its de novo expression is a reliable molecular marker for acute inflammation. Peptidylprolyl isomerase B, also known as cyclophilin B, induces chemotaxis and integrin-mediated adhesion of T cells to the extracellular matrix (ECM) in vitro. Basigin is also involved in inflammatory processes and is proposed to be a receptor of cyclophilin A. Stromal cell-derived factor 1, also known as CXC12, is a highly efficacious lymphocyte chemoattractant. Platelet factor 4, also known as CXCL4, is a strong chemoattractant for neutrophils and fibroblasts. In addition to its putative role in inflammation, it has been implicated in the pathogenesis of atopic dermatitis. Upregulation of arachidonate 5-lipoxygenase activating protein suggests a role for leukotrienes in this acute inflammatory response; Glutathione peroxidase may play an ancillary role. CD63 antigen can be interpreted as a marker of basophil activation and of degranulated neutrophils and monocytes. Legumain, an asparaginyl endopeptidase central to Class II MHC presentation of microbial antigens, is a potential molecular marker of macrophage differentiation and function. Follistatin is an activin antagonist implicated in wound repair; activin is an important participant in inflammation, repair and cytoprotection in various organs, but its induction is restricted to certain types of inflammation and its release is dependent upon the inflammatory setting. Nuclear factor-kappa-B is a transcription factor critical to the expression of a variety of chronic inflammatory disease states. The down-regulation of gelsolin in this model is notable, inasmuch as hemostatic, inflammatory, and fibroblast responses are blunted in mice lacking gelsolin. Expression of nascent polypeptide-associated complex regulates formation of Fas-associated death domain protein (FADD) oligomers and modulates FADD-mediated signaling; FADD protein is a critical mediator of signal transduction pathways activated by several members of the tumor necrosis factor (TNF)-receptor gene superfamily. Cathepsins are distinct intracellular acidic proteases that actively participate in the mechanism of antigen processing; conversely, the stefins are inhibitors of these cathepsins.

The immune response process is also statistically significantly induced in the lymphedema group versus controls. Genes such as cytotoxic T lymphocyte-associated proteins are associated with the function of activated T cell function and enhance TGF-□release by T cells. The leukocyte (or lymphocyte) specific protein 1 (LSP1) is a multi functional protein involved in the regulation of neutrophil motility, chemotaxis, adhesion and membrane immunoglobulin M (mIgM) mediated apoptosis of B-lymphocytes. Beta 2 microglobulin is a major histocompatibility complex protein that presents peptide antigens on cell surfaces for recognition by T-cell receptors. Lipocalin has recently been shown to participate in the response to bacterial growth. Galactose binding lectin is a participant in the acute phase response. Granulin is a high molecular weight secreted mitogen that is abundantly expressed in rapidly cycling epithelial cells and in the immune system. The high affinity Fc receptor for IgE is a key molecule in triggering the allergic reaction; it might be considered to be a mast cell-specific gene. Interferon gamma has an important role in activating macrophages in host defenses.

The cellular response to stress is another process that undergoes statistically significant induction during lymph stagnation. Among the stresses that can trigger this response are the elaboration of pathophysiological signals such as cytokines and eicosanoids. The expression of a variety of heat shock proteins (HSPs), is upregulated in our model. Additional evidence for the oxidative in lymphatic dysfunction consists of the upregulation of heme oxygenase 1 (HO-1). It is a downstream effector of the potent anti-inflammatory interleukin, IL-10.

Up-regulation of gene expression related to wound repair, and importantly, to fibrosis is also prominently seen. During wound repair granulin promotes granulation and neovascularization, and regulates inflammation. The expression of fibulins is induced in the setting of injury, in response to various stimuli. Biglycan (BGN) has been implicated in the regulation of matrix assembly, cellular adhesion, migration, and TGFbeta activity. Endoglin (CD 105) is a type III TGF-β1 receptor. It modulates the function of TGF-β1 by binding to and modulating signal transduction by the major type I and II TGF-β1 receptors. Lysyl oxidase (LO) plays a critical role in the biogenesis of connective tissue matrices. Alpha 2 actin has been identified as a marker of myofibroblast differentiation; all fibrocontractive diseases characterized by fibrosis entail the presence of myofibroblasts.

In addition to inflammatory/immune and stress responses, we have observed a gene expression profile that reflects alterations in the angiogenic response. Specifically, hypoxia inducible factor 1α has a key role in the cellular response to hypoxia, including the regulation of genes involved in energy metabolism, angiogenesis, and apoptosis. Alterations in the complement and Wnt pathways may also contribute significantly to the pathogenesis of the skin response to lymph stasis. The observed differences between the lymphedematous animals and the surgical controls are noteworthy. In the absence of any observed delay in wound healing, overt infection, or inflammation, the gene expression profile is characterized by a remarkable induction of whole biological processes by coordinate upregulation of their component genes. These observations underscore the interpretation that lymphedema is a pathological process that is much more complex than a simple disorder of fluid homeostasis. Indeed, these gene expression profiles superficially resemble those of other recently elucidated inflammatory conditions, such as multiple sclerosis, psoriasis, and even atherosclerosis.

In summary, we have used an animal model of lymphedema which shares many clinical and histopathological features with human lymphedema to identify the biological processes and genes which underlie them that are involved in the cutaneous response to lymphedema. The fact that inflammatory and immune processes are significantly induced suggests that these observations will provide a useful avenue for the investigation of novel pharmacologic strategies for lymphatic dysfunction. This approach is particularly attractive in light of the observed parallels with other systemic inflammatory disease states for which effective therapies already exist. Ultimately, such therapies must successfully diminish the impact of the soft tissue fibrosis and adipose deposition that characterize the late disease; in this regard, it is interesting to contemplate that expression of several such genes is detectably altered in this model, long before architectural evidence of the tissue abnormality is present. This identification of such genes provides an avenue for future investigation and, specifically, creates early insights into the elaboration of molecular therapeutics for this disease.

The tables below are also published in Tabibiazar R, Cheung L, Han J, Swanson J, Beilhack A, et al. (2006) Inflammatory Manifestations of Experimental Lymphatic Insufficiency. PLoS Med 3(7): e254 herein specifically incorporated by reference for the teachings including these tables.

TABLE 1

Primers and probes for qRT-PCR.

Names of Genes and Primer/Probe Sequences for the Taqman-Based Real-Time RT-PCR

| Gene Name | Foward Primers | SEQ ID NO. | Reverse Primers | SEQ ID NO. | Taqman Probes | SEQ ID NO. |
|---|---|---|---|---|---|---|
| calgranulin A | GACTTCAAGA AAATGGTCAC TACTGAGT | 1 | TGTCCAATTCT CTGAACAAGTT TTCGA | 2 | FAM-TCAGTTTGTG CAGAATAT-NFQ | 3 |
| calgranulin B | AGACAAATGG TGGAAGCACA GTT | 4 | CCAGGTCCTCC ATGATGTCATTT AT | 5 | FAM-TTCTCTTTCTT CATAAAGGTT GCC-NFQ | 6 |
| clusterin | AGGGCGAAG ACAAGTACTA CCTT | 7 | CACCACCACCT CAGTGACA | 8 | FAM-CCACCGTGAC CACCC-NFQ | 9 |
| MMP3 | TCCCGTTTCC ATCTCTCTCA AGA | 10 | GGGTACCACGA GGACATCAG | 11 | FAM-TCCCTCTATG GAACTCC-NFQ | 12 |
| MMP14 | CCCAAGGCA GCAACTTCAG | 13 | CCTGGAGGTAG GTAGCCATACTG | 14 | FAM-CCCGAAGCCT GGCTGC-NFQ | 15 |

Names of Taqman-Based Real Time RT-PCR probes

| Symbol | Name | Applied Biosystems |
|---|---|---|
| Cdh11 | cadherin 11 | Mm00515462_m1 |
| Hadh2 | Hydroxyacyl-Coenzyme A dehygrogenase type II | Mm00840109_m1 |
| myd88 | Myeloid diffexentianon primary response gene 88 | Mm00440338_m1 |

TABLE 2

| Gene ID | Gene Name | Score (d)a | Fold Change | q-Value (%) |
|---|---|---|---|---|
| Upregulated and downregulated genes in lymphedema vs. normal control (SAM FDR < 0.05) | | | | |
| AV020023 | S100 calcium binding protein A9 (calgranulin B) | 17.47 | 21.5 | 0.91 |
| AV171621 | stefin A3 | 14.55 | 4.3 | 0.91 |
| AV038429 | *Mus musculus*, similar to RIKEN cDNA 0610007L05 gene, clone MGC: 18838 IMAGE: 4212222, mRNA, complete cds | 11.98 | 2.9 | 0.91 |
| BG072297 | Fc receptor, IgE, high affinity I, gamma polypeptide | 11.02 | 4.2 | 0.91 |
| AA139015 | beta-2 microglobulin 1 | 0.86 | 3.9 | 0.91 |
| AV034788 | cytotoxic T lymphocyte-associated protein 2 alpha | 10.81 | 4.5 | 0.91 |
| 432238 EST | | 10.42 | 3.3 | 0.91 |
| AV171866 | ESTs, highly similar to CTY3 mouse stefin 3 (*Mus musculus*) | 10.04 | 4.6 | 0.91 |

TABLE 2-continued

| Gene ID | Gene Name | Score (d)a | Fold Change | q-Value (%) |
|---|---|---|---|---|
| AV068500 | Lgals2 107753 lysozyme | 10.02 | 4.6 | 0.91 |
| AA003942 | tenascin C | 9.21 | 7.8 | 0.91 |
| AV109517 | cytochrome b-245, alpha polypeptide | 8.91 | 2.6 | 0.91 |
| W48195 | RIKEN cDNA 1500040F11 gene | 8.80 | 1.8 | 0.91 |
| 43822 | EST | 8.68 | 2.1 | 0.91 |
| AW547306 | complement component 1, q subcomponent, c polypeptide | 8.38 | 2.6 | 0.91 |
| AV083964 | heme oxygenase (decyling) 1 | 8.12 | 1.6 | 0.91 |
| BG073325 | EST | 8.02 | 1.3 | 0.91 |
| AV094691 | ubiquitin-conjugating enzyme E2 variant 1 | 8.01 | 1.5 | 0.91 |
| AV114351 | retinol binding protein 1, cellular | 7.66 | 2.5 | 0.91 |
| BG063011 | cytotoxic T lymphocyte-associated protein 2 alpha | 7.54 | 4.0 | 0.91 |
| AV069980 | beta-2 microglobulin | 7.47 | 3.2 | 0.91 |
| AV133727 | signal sequence receptor, delta | 7.04 | 1.4 | 0.91 |
| 431201 | EST | 6.84 | 2.7 | 0.91 |
| 411130 | EST | 6.83 | 2.0 | 0.91 |
| AV09442 | EST, weakly similar to RL 15 rat 60S ribosomal protein L15 (*Rattus norvegicus*) | 6.72 | 1.7 | 0.91 |
| AV068190 | *M. musculus*, similar to hypothetical protein MGC3178, clone MGC: 28887 IMAGE: 4911455, mRNA, complete cds | 6.58 | 2.4 | 0.91 |
| AI118893 | S100a8 20201 EST | 6.57 | 16.0 | 0.91 |
| AW550933 | EST, weakly similar to PRP3 mouse proline-rich protein MP-3 (*M. musculus*) | 6.57 | 1.3 | 0.91 |
| AV094499 | RIKEN cDNA 1300017C10 gene | 6.49 | 1.6 | 0.91 |
| AV060165 | EST | 6.37 | 3.9 | 0.91 |
| AV066072 | RIKEN cDNA 1110004C05 gene | 6.35 | 2.1 | 0.91 |
| 432539 | EST | 6.22 | 3.8 | 0.91 |
| AV037118 | beta-2 microglobulin | 6.14 | 3.0 | 0.91 |
| AV028863 | ferritin heavy chain | 6.06 | 2.0 | 0.91 |
| AV035363 | proteoglycan, secretory granule | 5.98 | 3.7 | 0.91 |
| AV013352 | RIKEN cDNA 1810009M01 gene | 5.94 | 2.3 | 0.91 |
| AV054688 | EST | 5.93 | 1.7 | 0.91 |
| 412016 | EST | 5.86 | 3.6 | 0.91 |
| 411315 | EST | 5.84 | 1.8 | 0.91 |
| 412595 | EST | 5.82 | 1.4 | 0.91 |
| AV061443 | interferon gamma receptor | 5.81 | 2.0 | 0.91 |
| BG072156 | RIKEN cDNA 1110004C05 gene | 5.78 | 3.7 | 0.91 |
| 413077 | EST | 5.73 | 1.7 | 0.91 |
| AV035765 | EST | 5.72 | 4.5 | 0.91 |
| AA177689 | myeloid ecotropic viral integration site-related gene 2 | 5.71 | 1.6 | 0.91 |
| AA162879 | stromal cell-derived factor 1 | 5.70 | 2.4 | 0.91 |
| AV052140 | stromal cell-derived factor 1 | 5.63 | 2.0 | 0.91 |
| AA087526 | retinol binding protein 1, cellular | 5.59 | 2.9 | 0.91 |
| AV109528 | myosin light chain, alkali, nonmuscle | 5.57 | 1.7 | 0.91 |
| AV108847 | *M. musculus*, similar to nucleolar GTPase, clone MGC: 7863 IMAGE: 3501393, mRNA complete cds | 5.54 | 2.3 | 0.91 |
| BG070106 | lipocalin 2 | 5.47 | 6.1 | 0.91 |
| 431107 | EST | 5.41 | 2.6 | 1.08 |
| BG073227 | fibulin 2 | 5.41 | 2.0 | 1.08 |
| AA072722 | Fc receptor, IgE, high affinity I, gamma polypeptide | 5.35 | 3.0 | 1.08 |
| 412394 | EST | 5.31 | 1.7 | 1.08 |
| BG063844 | plastin 2, L | 5.29 | 3.3 | 1.08 |
| AV087823 | carbonyl reductase 2 | 5.29 | 1.8 | 1.08 |
| 413592 | EST | 5.28 | 2.4 | 1.08 |
| AV036203 | lymphocyte specific 1 | 5.22 | 1.7 | 1.08 |
| AV141619 | RIKEN cDNA 1810037I17 gene | 5.22 | 1.4 | 1.08 |
| BG074642 | RIKEN cDNA 0610007L05 gene | 5.21 | 2.5 | 1.08 |
| AV070323 | RIKEN cDNA 2610003B19 gene | 5.21 | 1.7 | 1.08 |
| AV104403 | cathepsin Z | 5.17 | 2.2 | 1.08 |
| BG068219 | legumain | 5.16 | 2.4 | 1.08 |
| AV085954 | complement component 1, q subcomponent, beta polypeptide | 5.15 | 3.2 | 1.08 |
| AV058060 | calmodulin 1 | 5.15 | 1.8 | 1.08 |
| AV087404 | RIKEN cDNA 2310056P07 gene | 5.09 | 1.6 | 1.08 |
| AV094766 | *M. musculus*, similar to aspartyl-tRNA synthetase, clone MGC: 6719 IMAGE: 3586278, mRNA, complete cds | 5.08 | 2.3 | 1.08 |
| AV024220 | follistatin-like | 5.03 | 3.2 | 1.08 |
| 411275 | EST | 5.03 | 2.0 | 1.08 |
| AV088911 | S100 calcium binding protein A11 (calizzarin) | 4.97 | 1.6 | 1.08 |
| AV109524 | platelet factor 4 | 4.96 | 1.8 | 1.08 |

TABLE 2-continued

| Gene ID | Gene Name | Score (d)a | Fold Change | q-Value (%) |
|---|---|---|---|---|
| AV094436 | ubiquinol-cytochrome c reductase core protein 1 | 4.96 | 2.2 | 1.08 |
| AI875081 | glutathione peroxidase 1 | 4.95 | 1.9 | 1.08 |
| AV104473 | cathepsin Z | 4.92 | 2.0 | 1.08 |
| AV093499 | thymosin, beta 4, X chromosome | 4.91 | 1.7 | 1.08 |
| AV001464 | granulin | 4.90 | 1.7 | 1.08 |
| AV087961 | endomucin | 4.88 | 1.7 | 1.08 |
| BG074570 | myosin light chain, alkali, nonmuscle | 4.83 | 1.5 | 1.08 |
| AV113890 | fatty acid binding protein 5, epidermal | 4.81 | 1.9 | 1.08 |
| AV133965 | esterase 10 | 4.81 | 1.9 | 1.08 |
| AV084804 | *M. musculus*, similar to transgelin 2, MGC: 6300 IMAGE: 2654381, mRNA, complete cds | 4.80 | 1.6 | 1.08 |
| BG071322 | carbonyl reductase 2 | 4.78 | 1.6 | 1.08 |
| AI847496 | sorting nexin 5 | 4.78 | 2.0 | 1.08 |
| AV093793 | ribosomal protein L24 | 4.76 | 1.4 | 1.08 |
| AW556849 | EST | 4.73 | 1.5 | 1.08 |
| AI841291 | spermidine/spermine N1-acetyl transferase | 4.72 | 1.5 | 1.08 |
| 411545 | EST | 4.70 | 2.7 | 1.08 |
| BG073274 | guanine nucleotide binding protein, alpha inhibiting 2 | 4.65 | 1.5 | 1.08 |
| AV014173 | ESTs, highly similar to T00361 hypothet protein KIAA0678 (*Homo sapiens*) | 4.59 | 1.8 | 1.36 |
| AV009300 | procollagen, type IV, alpha 1 | 4.54 | 2.0 | 1.36 |
| AV010312 | procollagen, type IV, alpha 2 | 4.50 | 2.0 | 1.36 |
| BG074937 | histocompatiblility 2, D region locus 1 | 4.49 | 2.1 | 1.36 |
| W14193 | S100 calcium binding protein A9 (calgranulin B) | 4.47 | 14.9 | 1.36 |
| AV023779 | Sjogren's syndrome/scleroderma autoantigen 1 homolog (*H. sapiens*) | 4.47 | 3.7 | 1.36 |
| AV086173 | peptidylprolyl isomerase B | 4.41 | 1.4 | 1.59 |
| 431892 | EST | 4.40 | 2.8 | 1.59 |
| 432647 | EST | 4.39 | 3.4 | 1.59 |
| 431995 | EST | 4.39 | 1.5 | 1.59 |
| AV095167 | glutathione peroxidase 1 | 4.38 | 1.7 | 1.59 |
| AI596034 | receptor tyrosine kinase-like orphan receptor 2 | 4.35 | 1.7 | 1.59 |
| 411582 | EST | 4.34 | 1.3 | 1.59 |
| BG067559 | cathepsin C | 4.33 | 2.3 | 1.59 |
| AV086001 | highly similar to CYT3 mouse stefin 3 (*M. musculus*) | 4.33 | 2.3 | 1.59 |
| AV171061 | coactosin-like protein | 4.32 | 1.3 | 1.59 |
| BG065250 | cathepsin H | 4.32 | 1.5 | 1.59 |
| AV017041 | N-acetylneuraminate pyruvate lyase | 4.30 | 4.1 | 1.59 |
| AV096227 | thymosin, beta 10 | 4.29 | 2.5 | 1.59 |
| 411500 | EST | 4.28 | 2.7 | 1.59 |
| AV106608 | glutathione peroxidase 1 | 4.27 | 1.8 | 1.59 |
| AV104166 | arachidonate 5-lipoxygenase activating protein | 4.25 | 2.9 | 1.59 |
| AI325865 | actin related protein 2/3 complex, subunit 4 (20 kDa) | 4.24 | 1.5 | 1.73 |
| BG074171 | ESTs, highly similar to CYT3 mouse stefin 3 (*M. musculus*) | 4.24 | 6.3 | 1.73 |
| BG075608 | Tpi1 21991 triosephosphate isomerase | 4.24 | 1.9 | 1.73 |
| AV105953 | calreticulin | 4.23 | 2.0 | 1.73 |
| AV094913 | RIKEN cDNA 1110020C13 gene | 4.22 | 1.3 | 1.73 |
| 412705 | EST | 4.22 | 4.0 | 1.73 |
| 410890 | EST | 4.21 | 1.7 | 1.73 |
| 412501 | EST | 4.21 | 1.4 | 1.73 |
| AI526714 | glutathione peroxidase 1 | 4.18 | 1.8 | 1.73 |
| AV014751 | lysyl oxidase | 4.17 | 2.7 | 1.73 |
| BI076685 | EST | 4.17 | 1.4 | 1.73 |
| AV001134 | Rho, GDP dissociation inhibitor (GDI) beta | 4.15 | 1.8 | 1.73 |
| BG072620 | ribosomal protein S6 | 4.14 | 1.3 | 1.73 |
| BG065930 | RIKEN cDNA 3110023F10 gene | 4.13 | 1.6 | 1.73 |
| BG076357 | erythroid differentiation regulator | 4.11 | 2.7 | 1.73 |
| AV094406 | *M. musculus*, clone IMAGE: 3499608, mRNA, partial cds | 4.11 | 1.5 | 1.73 |
| AW554113 | EST | 4.11 | 1.5 | 1.73 |
| 411855 | EST | 4.10 | 1.5 | 1.73 |
| AV031220 | SET translocation | 4.09 | 1.5 | 1.96 |
| BG072550 | RIKEN cDNA 120011K09 gene | 4.08 | 1.8 | 1.96 |
| AV038462 | cytotoxic T lymphocyte-associated protein 2 alpha | 4.07 | 4.0 | 1.96 |
| AV120085 | ribosomal protein S18 | 4.06 | 1.2 | 1.96 |
| AV009166 | capping protein beta 1 | 4.05 | 1.7 | 1.96 |
| 412280 | EST | 4.04 | 2.9 | 1.96 |
| AV111409 | ubiquitin-like 5 | 4.02 | 1.3 | 1.96 |

TABLE 2-continued

| Gene ID | Gene Name | Score (d)a | Fold Change | q-Value (%) |
|---|---|---|---|---|
| AV039992 | zuotin related factor 2 | 4.02 | 1.3 | 1.96 |
| AW543803 | hypoxia inducible factor 1, alpha subunit | 4.01 | 1.9 | 1.96 |
| AW551760 | interferon induced transmembrane protein 3-like | 4.00 | 1.7 | 1.96 |
| BG071182 | RIKEN cDNA 0610011I04 gene | 4.00 | 2.7 | 1.96 |
| BG065327 | traube | 4.00 | 1.2 | 1.96 |
| AW553642 | M. musculus, similar to caldesmon 1, clone MGC: 30319 IMAGE: 5148205, mRNA, complete cds | 4.00 | 2.1 | 1.96 |
| 430643 | EST | 4.00 | 3.4 | 1.96 |
| 432671 | EST | 3.98 | 1.8 | 1.96 |
| 431125 | EST | 3.97 | 2.7 | 1.96 |
| AV009103 | Expressed sequence AA408606 | 3.96 | 1.5 | 1.96 |
| AW554082 | EST | 3.95 | 1.8 | 1.96 |
| AV094414 | M. musculus, clone MGC: 31031 IMAGE: 5137689, mRNA, complete cds | 3.91 | 2.3 | 1.96 |
| AV017679 | small EDRK-rich factor 2 | 3.90 | 1.7 | 1.96 |
| 411766 | EST | 3.89 | 1.3 | 1.96 |
| AV094647 | M. musculus, clone MGC: 37950 IMAGE: 5132866, mRNA, complete cds | 3.89 | 1.3 | 2.28 |
| AV105113 | RIKEN cDNA 1110004C05 gene | 3.89 | 1.6 | 2.28 |
| AF065441 | fibroblast growth factor binding protein 1 | 3.87 | 1.5 | 2.28 |
| AV065392 | ESTs | 3.87 | 1.4 | 2.28 |
| BG063611 | lectin, galactose binding, soluble 1 | 3.86 | 2.9 | 2.28 |
| 430977 | EST | 3.86 | 2.7 | 2.28 |
| BG072866 | IMAGE: 4218551, mRNA, complete cds | 3.85 | 1.3 | 2.28 |
| 411576 | EST | 3.84 | 2.5 | 2.28 |
| AV094612 | Expressed sequence C87860 | 3.83 | 1.4 | 2.28 |
| BG075953 | Vhlh-interacting deubiquitinating enzyme 1 | 3.83 | 1.9 | 2.28 |
| AW548371 | EST | 3.81 | 1.7 | 2.28 |
| 432957 | EST | 3.81 | 2.1 | 2.28 |
| AV109529 | ferritin heavy chain | 3.81 | 2.2 | 2.28 |
| AV109316 | thymosin, beta 4, X chromosome | 3.81 | 1.7 | 2.28 |
| 433177 | EST | 3.80 | 1.6 | 2.28 |
| 413039 | EST | 3.80 | 1.8 | 2.28 |
| AV070066 | EST | 3.78 | 1.5 | 2.28 |
| AV294875 | phosphoglycerate kinase 1 | 3.78 | 1.7 | 2.28 |
| BG072801 | S100 calcium binding protein A9 (calgranulin B) | 3.78 | 19.2 | 2.28 |
| AV014493 | zinc finger protein 100 | 3.78 | 1.6 | 2.28 |
| 413454 | EST | 3.77 | 4.5 | 2.28 |
| BG075853 | selenoprotein P, plasma 1 | 3.77 | 2.8 | 2.28 |
| AV087234 | Expressed sequence C86191 | 3.76 | 1.7 | 2.28 |
| AV028503 | spermidine/spermine N1-acetyl transferase | 3.76 | 1.6 | 2.73 |
| AV133930 | hexosaminidase A | 3.74 | 2.0 | 2.73 |
| 410654 | EST | 3.74 | 2.7 | 2.73 |
| AV025941 | aquaporin 1 | 3.74 | 2.0 | 2.73 |
| AV050073 | S100 calcium binding protein A9 (calgranulin B) | 3.74 | 22.5 | 2.73 |
| AV093600 | ATP synthase, Hp transporting, mitochondrial F0 complex, subunit f, isoform 2 | 3.73 | 1.6 | 2.73 |
| AA408841 | cystein rich protein | 3.73 | 1.7 | 2.73 |
| AW553287 | osteoblast specific factor 2 (fasciclin I-like) | 3.72 | 2.1 | 2.73 |
| AV043279 | cholinergic receptor, nicotinic, epsilon polypeptide | 3.71 | 1.6 | 2.73 |
| AV134223 | fatty acid binding protein 5, epidermal | 3.70 | 2.2 | 2.73 |
| BG063873 | ferritin light chain 1 | 3.70 | 2.4 | 2.73 |
| AV134053 | RNA polymerase 1-3 (16-kDa subunit) | 3.70 | 1.2 | 2.73 |
| AW547223 | ribosomal protein L29 | 3.68 | 2.5 | 2.73 |
| BG064350 | actinin, alpha 1 | 3.66 | 1.8 | 2.73 |
| AV113595 | embryonic ectoderm development | 3.65 | 1.9 | 2.73 |
| AV094967 | RIKEN cDNA 2010000G05 gene | 3.65 | 1.4 | 2.73 |
| AV072373 | RIKEN cDNA 2510010F10 gene | 3.63 | 2.3 | 2.73 |
| AV094998 | lysyl oxidase-like | 3.63 | 1.8 | 2.73 |
| AV012373 | transgelin | 3.62 | 1.5 | 2.73 |
| AA162273 | procollagen, type IV, alpha 1 | 3.62 | 3.0 | 2.73 |
| BG065103 | lymphocyte antigen 6 complex, locus E | 3.61 | 1.5 | 2.73 |
| BG071626 | ESTs, Moderately similar to glyceraldehyde 3-phosphate dehydrogenase (M. musculus) | 3.60 | 1.5 | 3.17 |
| BG074224 | ESTs | 3.60 | 1.4 | 3.17 |
| AV000846 | superoxide dismutase 2, mitochondrial | 3.58 | 1.5 | 3.17 |
| AV030230 | ESTs | 3.57 | 2.2 | 3.17 |
| AA980714 | platelet/endothelial cell adhesion molecule | 3.56 | 2.0 | 3.17 |
| AV162332 | RIKEN cDNA 3110001M13 gene | 3.55 | 2.3 | 3.17 |
| 412441 | EST | 3.55 | 1.8 | 3.17 |
| AV031080 | ubiquitin-like 3 | 3.55 | 1.9 | 3.17 |
| AV030853 | RIKEN cDNA 1100001J13 gene | 3.54 | 1.5 | 3.17 |

TABLE 2-continued

| Gene ID | Gene Name | Score (d)a | Fold Change | q-Value (%) |
|---|---|---|---|---|
| AV094526 | M. musculus, hypothetical protein MGC11287 similar to ribosomal protein S6 kinase, clone MGC: 28043 IMAGE: 3672127, mRNA, complete cds | 3.54 | 1.2 | 3.17 |
| AV133784 | M. musculus, similar to caldesmon 1, clone MGC: 30319 IMAGE: 5148205, mRNA, complete cds | 3.53 | 1.9 | 3.17 |
| C79946 | Expressed sequence C79946 | 3.52 | 1.7 | 3.17 |
| AA086550 | myeloid ecotropic viral integration site-related gene 2 | 3.52 | 1.6 | 3.17 |
| AW550650 | t-complex testis expressed 1 | 3.51 | 1.8 | 3.17 |
| AV070981 | hypoxia inducible factor 1, alpha subunit | 3.50 | 1.5 | 3.17 |
| BG073809 | biglycan | 3.49 | 2.6 | 3.17 |
| BG071407 | malate dehydrogenase, mitochondrial | 3.49 | 1.5 | 3.17 |
| AV028607 | serine (or cysteine) proteinase inhibitor, clade I (neuroserpin), member 1 | 3.48 | 1.9 | 3.17 |
| AV006041 | RIKEN cDNA 2900073G15 gene | 3.48 | 1.6 | 3.17 |
| 412701 | EST | 3.48 | 1.4 | 3.17 |
| AV103730 | actin related protein 2/3 complex, subunit 3 (21 kDa) | 3.48 | 1.7 | 3.17 |
| AV109544 | microtubule-associated protein 1 light chain 3 | 3.48 | 1.3 | 3.17 |
| AV030400 | myosin light chain, alkali, nonmuscle | 3.45 | 1.7 | 3.17 |
| 432209 | EST | 3.45 | 2.0 | 3.17 |
| AV114184 | histocompatibility 2, complement component factor B | 3.43 | 3.1 | 3.24 |
| BG067257 | clathrin, light polypeptide (Lca) | 3.41 | 1.4 | 3.24 |
| BG070050 | microtubule-associated protein 1 light chain 3 | 3.41 | 1.3 | 3.24 |
| AV017254 | membrane protein, palmitoylated (55 kDa) | 3.40 | 1.9 | 3.24 |
| AV093759 | ribosomal protein S12 | 3.40 | 1.5 | 3.24 |
| AI841252 | transmembrane protein 4 | 3.39 | 1.4 | 3.24 |
| AV006536 | EST | 3.38 | 1.3 | 3.24 |
| AV094757 | EST | 3.37 | 2.0 | 3.24 |
| AV055121 | selenoprotein R | 3.36 | 1.6 | 3.24 |
| BG073062 | ATP synthase, Hp transporting, mitochondrial F0 complex, subunit f, isoform 2 | 3.36 | 1.5 | 3.24 |
| AU043587 | membrane-associated protein 17 | 3.35 | 1.5 | 3.24 |
| AV087816 | keratin complex 1, acidic, gene 14 | 3.34 | 1.4 | 3.24 |
| AV074746 | thymosin, beta 4, X chromosome | 3.34 | 1.7 | 3.24 |
| AV087388 | M. musculus, similar to hypothetical protein DKFZp566A1524, clone MGC: 18989 IMAGE: 4012217, mRNA, complete cds | 3.33 | 2.1 | 3.24 |
| BG065030 | glutathione peroxidase 1 | 3.33 | 1.5 | 3.24 |
| BG071424 | integral membrane protein 3 | 3.33 | 1.3 | 3.24 |
| AV133758 | phosphoglycerate kinase 1 | 3.33 | 2.3 | 3.24 |
| BG075599 | membrane protein, palmitoylated (55 kDa) | 3.31 | 1.4 | 3.24 |
| AV094520 | HpaII tiny fragments locus 9c | 3.31 | 1.5 | 3.24 |
| BG064704 | lectin, galactose binding, soluble 1 | 3.31 | 2.0 | 3.53 |
| 411696 | EST | 3.29 | 1.4 | 3.53 |
| AV019210 | elastin | 3.29 | 1.8 | 3.53 |
| AV084625 | BTB (POZ) domain containing 1 | 3.29 | 1.6 | 3.53 |
| AV037171 | ESTs, Weakly similar to NUML mouse NADH-ubiquinone oxidoreductase MLRQ subunit (M. musculus) | 3.28 | 1.3 | 3.53 |
| BG063257 | RIKEN cDNA 2510027N19 gene | 3.28 | 1.6 | 3.53 |
| AV033994 | proteoglycan, secretory granule | 3.27 | 3.7 | 3.53 |
| AV081086 | EST | 3.27 | 1.7 | 3.53 |
| 412241 | EST | 3.25 | 1.4 | 3.53 |
| AV006019 | phosphatidylinositol glycan, class Q | 3.24 | 1.7 | 3.53 |
| AV013830 | S100 calcium binding protein A13 | 3.24 | 1.3 | 3.53 |
| AV015250 | DnaJ (Hsp40) homolog, subfamily B, member 5 | 3.24 | 2.6 | 3.53 |
| 204387 | EST | 3.24 | 1.6 | 3.53 |
| AW323058 | CD63 antigen | 3.23 | 1.5 | 3.53 |
| AI574416 | transforming growth factor, beta 2 | 3.23 | 1.8 | 3.53 |
| BG063870 | actin, beta, cytoplasmic | 3.22 | 1.3 | 3.53 |
| 410751 | EST | 3.22 | 1.4 | 3.53 |
| 431101 | EST | 3.22 | 1.7 | 3.53 |
| 410791 | EST | 3.21 | 1.5 | 3.53 |
| BE307724 | prosaposin | 3.20 | 1.4 | 3.53 |
| AV073780 | RIKEN cDNA 2600010N21 gene | 3.19 | 1.9 | 3.53 |
| AV308712 | GLI-Kruppel family member GLI | 3.19 | 1.4 | 3.53 |
| BG072588 | RIKEN cDNA 2410030A14 gene | 3.19 | 1.4 | 3.53 |
| AV074050 | retinol binding protein 1, cellular | 3.18 | 1.8 | 3.53 |
| AV035206 | RIKEN cDNA 1300002P22 gene | 3.17 | 2.1 | 3.53 |
| AV094410 | differential display and activated by p53 | 3.17 | 1.3 | 3.53 |
| AV171092 | actin, alpha, cardiac | 3.17 | 1.2 | 3.53 |

TABLE 2-continued

| Gene ID | Gene Name | Score (d)a | Fold Change | q-Value (%) |
|---|---|---|---|---|
| 411087 | EST | 3.16 | 1.5 | 3.53 |
| BG064536 | RIKEN cDNA 1110007A14 gene | 3.16 | 1.6 | 3.53 |
| AA776162 | calcium channel, voltage-dependent, L type, alpha 1B subunit | 3.15 | 1.6 | 3.73 |
| AV162471 | EST | 3.15 | 2.1 | 3.73 |
| AV041829 | thymosin, beta 10 | 3.15 | 2.3 | 3.73 |
| 412704 | EST | 3.15 | 1.3 | 3.73 |
| AV089281 | procollagen, type V, alpha 2 | 3.14 | 2.4 | 3.73 |
| AV109643 | Niemann Pick type C2 | 3.14 | 2.0 | 3.73 |
| AI325874 | heat shock 10-kDa protein 1 (chaperonin 10) | 3.13 | 1.5 | 3.73 |
| 432933 | EST | 3.13 | 1.3 | 3.73 |
| BG065380 | pyruvate kinase 3 | 3.13 | 1.3 | 3.73 |
| BG063305 | ATPase, Nap/Kp transporting, beta 1 polypeptide | 3.12 | 1.3 | 3.73 |
| BG069782 | CD63 antigen | 3.10 | 1.5 | 3.73 |
| BG064917 | RIKEN cDNA 1110021D01 gene | 3.10 | 1.3 | 3.73 |
| BG072879 | cytochrome P450, steroid inducible 3a11 | 3.10 | 1.3 | 3.73 |
| AV093637 | platelet-activating factor acetylhydrolase, isoform 1b, alpha 1 subunit | 3.09 | 1.4 | 3.73 |
| AV052389 | serine protease inhibitor, Kazal type 4 | 3.09 | 2.6 | 3.73 |
| RW:284 | EST | 3.08 | 3.7 | 3.73 |
| AV094857 | RIKEN cDNA 2410003B16 gene | 3.08 | 1.4 | 3.73 |
| 411234 | EST | 3.08 | 1.9 | 3.73 |
| AV156366 | glyceraldehyde 3-phosphate dehydrogenase | 3.08 | 1.6 | 3.73 |
| 41261 | EST | 3.08 | 1.8 | 3.73 |
| BG066823 | creatine kinase, mitochondrial 1, ubiquitous | 3.07 | 1.5 | 3.73 |
| AV028632 | RIKEN cDNA 5530601H04 gene | 3.07 | 1.9 | 3.73 |
| AV094958 | SEC22 vesicle trafficking protein-like 1 (*S. cerevisiae*) | 3.07 | 1.4 | 3.73 |
| X77585 | thioredoxin 1 | 3.07 | 1.6 | 3.73 |
| AV049504 | EST, weakly similar to RL37 human 60S ribosomal protein L37 (*R. norvegicus*) | 3.07 | 1.2 | 3.73 |
| 412915 | EST | 3.06 | 1.6 | 3.73 |
| BG071240 | phosphatidylinositol transfer protein | 3.06 | 1.3 | 3.73 |
| AV088363 | ribosomal protein, large P2 | 3.06 | 1.4 | 3.73 |
| AW989643 | EST | 3.05 | 1.9 | 3.73 |
| AV149918 | carbonic anhydrase 2 | 3.05 | 2.1 | 3.74 |
| AV084873 | lysosomal-associated protein transmembrane 5 | 3.05 | 1.7 | 3.74 |
| BG072998 | Expressed sequence AU018638 | 3.04 | 1.8 | 3.74 |
| 413190 | EST | 3.03 | 1.3 | 3.74 |
| AA000350 | fibrilin 1 | 3.02 | 1.6 | 3.74 |
| BG075073 | thymosin, beta 4, X chromosome | 3.02 | 1.7 | 3.74 |
| AA693053 | protein tyrosine phosphatase, non-receptor type 2 | 3.02 | 1.5 | 3.74 |
| AV035959 | RIKEN cDNA 2410030A14 gene | 3.02 | 1.3 | 3.74 |
| BG069532 | Niemann Pick type C2 | 3.01 | 1.4 | 3.74 |
| AV083728 | Niemann Pick type C2 | 3.01 | 1.4 | 3.74 |
| AA410137 | EST | 3.00 | 1.3 | 3.74 |
| AV082005 | RIKEN cDNA 0610040D20 gene | 3.00 | 1.5 | 3.74 |
| AV103733 | epithelial membrane protein 3 | 3.00 | 1.4 | 3.74 |
| BG063700 | RIKEN cDNA 2210417O06 gene | 2.99 | 1.5 | 3.74 |
| AA608500 | S100 calcium binding protein A6 (calcyclin) | 2.99 | 1.6 | 3.74 |
| AI836995 | nascent polypeptide-associated complex alpha polypeptide | 2.99 | 1.3 | 3.74 |
| 431042 | EST | 2.99 | 1.6 | 3.74 |
| AV094984 | aldolase 1, A isoform | 2.99 | 1.6 | 3.74 |
| AV057697 | Expressed sequence AV001623 | 2.98 | 1.3 | 3.74 |
| AV110745 | uncoupling protein 2, mitochondrial | 2.98 | 1.5 | 3.74 |
| AV025885 | *M. musculus*, similar to caldesmon 1, clone MGC: 30319 IMAGE: 5148205, mRNA, complete cds | 2.98 | 3.1 | 3.74 |
| BG070959 | Ral-interacting protein 1 | 2.98 | 1.4 | 3.74 |
| AV166088 | zyxin | 2.96 | 1.6 | 3.74 |
| AV061097 | heat shock 30-kDa protein | 2.96 | 1.3 | 3.74 |
| AV031183 | cytochrome c oxidase, subunit Vb | 2.96 | 1.4 | 3.74 |
| AI325844 | proteoglycan, secretory granule | 2.96 | 2.6 | 3.74 |
| BG076355 | signal transducer and activator of transcription 3 | 2.95 | 1.3 | 3.74 |
| AV140511 | cytochrome c oxidase subunit VIIa polypeptide 2-like | 2.95 | 1.2 | 3.74 |
| AV078179 | selenoprotein W, muscle 1 | 2.95 | 1.7 | 3.74 |
| AV086834 | BCL2/adenovirus E1B 19-kDa interacting protein 1, NIP3 | 2.94 | 1.7 | 3.74 |
| AW550270 | tenascin C | 2.93 | 5.2 | 3.74 |

TABLE 2-continued

| Gene ID | Gene Name | Score (d)a | Fold Change | q-Value (%) |
|---|---|---|---|---|
| AV109501 | *M. musculus*, similar to spondin 1a, clone MGC: 18859 IMAGE: 4221758, mRNA, complete cds | 2.93 | 1.7 | 3.74 |
| AV103910 | RAB11a, member RAS oncogene family | 2.93 | 1.4 | 3.74 |
| 411848 | EST | 2.93 | 1.6 | 3.74 |
| AV094787 | mitochondrial ribosomal protein L1 | 2.92 | 1.6 | 4.03 |
| 410746 | EST | 2.92 | 1.8 | 4.03 |
| BG072740 | actin related protein 2/3 complex, subunit 3 (21 kDa) | 2.92 | 1.6 | 4.03 |
| AA261240 | SRY-box containing gene 18 | 2.92 | 1.8 | 4.03 |
| 410959 | EST | 2.91 | 1.5 | 4.03 |
| BG064603 | ribosomal protein L41 | 2.91 | 1.4 | 4.03 |
| 431066 | EST | 2.90 | 1.2 | 4.03 |
| 432500 | EST | 2.90 | 1.4 | 4.03 |
| AV109648 | retinoblastoma binding protein 4 | 2.90 | 2.0 | 4.03 |
| BG073560 | cofilin 1, non-muscle | 2.89 | 1.7 | 4.03 |
| AV133972 | heterogeneous nuclear ribonucleoprotein A1 | 2.89 | 1.8 | 4.03 |
| 411828 | EST | 2.88 | 1.2 | 4.03 |
| AV086965 | calmodulin 1 | 2.88 | 1.5 | 4.03 |
| AV095050 | heat shock 70-kDa protein 8 | 2.87 | 1.5 | 4.03 |
| AV094992 | procollagen, type IX, alpha 3 | 2.87 | 1.6 | 4.03 |
| BG066918 | translocase of inner mitochondrial membrane 8 homolog b (*Saccharomyces cerevisiae*) | 2.87 | 1.5 | 4.03 |
| AV108774 | RIKEN cDNA 2510048K03 gene | 2.86 | 2.4 | 4.03 |
| BG074443 | lectin, galactose binding, soluble 7 | 2.86 | 1.3 | 4.03 |
| AV104097 | basigin | 2.86 | 1.7 | 4.03 |
| BG063004 | lectin, galactose binding, soluble 1 | 2.85 | 2.5 | 4.03 |
| AV105178 | ESTs | 2.85 | 1.6 | 4.03 |
| AV142972 | EST | 2.85 | 1.6 | 4.03 |
| AV029181 | synaptotagmin 4 | 2.84 | 2.8 | 4.03 |
| BG072227 | LPS-induced TNF-alpha factor | 2.84 | 1.3 | 4.03 |
| BG075934 | transaldolase 1 | 2.83 | 1.3 | 4.28 |
| 431681 | EST | 2.83 | 1.7 | 4.28 |
| AV081042 | serine protease inhibitor 8 | 2.83 | 1.3 | 4.28 |
| BG063024 | RIKEN cDNA 2600015J22 gene | 2.83 | 1.4 | 4.28 |
| AV068926 | hypoxia inducible factor 1, alpha subunit | 2.83 | 1.4 | 4.28 |
| BG064187 | ribosomal protein S18 | 2.82 | 1.2 | 4.28 |
| AV133978 | Similar to TAF6-like RNA polymerase II, p300/CBP-associated factor (PCAF)-associated factor, 65 kD | 2.82 | 1.8 | 4.28 |
| AV089437 | keratin complex 1, acidic, gene 13 | 2.81 | 2.2 | 4.28 |
| 410900 | EST | 2.81 | 2.9 | 4.28 |
| AV073989 | RIKEN cDNA 2310046G15 gene | 2.81 | 1.7 | 4.28 |
| BF720949 | nuclear factor of kappa light chain gene enhancer in B cells 1, p105 | 2.80 | 1.5 | 4.28 |
| AV051965 | sialyltransferase 7 | 2.79 | 1.8 | 4.28 |
| AV094533 | cathepsin L | 2.79 | 1.3 | 4.28 |
| AV130661 | heterogeneous nuclear ribonucleoprotein A1 | 2.79 | 1.7 | 4.28 |
| AA080001 | calmodulin 1 | 2.79 | 1.5 | 4.28 |
| AV109477 | cathepsin L | 2.79 | 1.5 | 4.28 |
| AA066030 | heat shock 70-kDa protein 2 | 2.78 | 1.4 | 4.28 |
| BG065539 | RIKEN cDNA 3110023E09 gene | 2.78 | 1.5 | 4.28 |
| AV095469 | ribosomal protein L19 | 2.78 | 1.3 | 4.28 |
| BG071748 | RIKEN cDNA 6720465F12 gene | 2.78 | 1.8 | 4.28 |
| 411794 | EST | 2.78 | 1.5 | 4.28 |
| BG070325 | nuclease sensitive element binding protein 1 | 2.78 | 1.3 | 4.28 |
| AV070988 | mitochondrial carrier homolog 2 | 2.77 | 1.2 | 4.28 |
| BG064794 | ferritin light chain 1 | 2.77 | 2.3 | 4.28 |
| AI596209 | receptor tyrosine kinase-like orphan receptor 2 | 2.77 | 1.4 | 4.28 |
| AA815993 | actin, alpha 2, smooth muscle, aorta | 2.77 | 1.7 | 4.28 |
| AV039554 | proline-rich protein 13 | 2.76 | 1.5 | 4.28 |
| AV094728 | eukaryotic translation initiation factor 4E | 2.76 | 1.3 | 4.28 |
| BG064454 | RIKEN cDNA 1300011C24 gene | 2.76 | 1.4 | 4.28 |
| AV006514 | interferon (alpha and beta) receptor 2 | 2.76 | 1.5 | 4.28 |
| AV086929 | RIKEN cDNA 9430096L06 gene | 2.75 | 1.8 | 4.28 |
| BG063866 | Finkel-Biskis-Reilly murine sarcoma virus (FBR-MuSV) ubiquitously expressed (fox-derived) | 2.75 | 1.3 | 4.28 |
| BG072299 | receptor (calcitonin) activity modifying protein 2 | 2.75 | 1.4 | 4.28 |
| 412038 | EST | 2.75 | 1.4 | 4.28 |
| BG067962 | RIKEN cDNA 1110020C13 gene | 2.75 | 1.4 | 4.28 |
| 412958 | EST | 2.75 | 1.4 | 4.28 |
| AI226124 | integrin beta 1 (fibronectin receptor beta) | 2.74 | 1.6 | 4.90 |
| BG066897 | ubiquitin-like 5 | 2.74 | 1.2 | 4.90 |

TABLE 2-continued

| Gene ID | Gene Name | Score (d)a | Fold Change | q-Value (%) |
|---|---|---|---|---|
| AV067886 | RIKEN cDNA 1810027O10 gene | 2.74 | 1.5 | 4.90 |
| AV086649 | geminin | 2.73 | 1.7 | 4.90 |
| AV023199 | selenoprotein W, muscle 1 | 2.73 | 2.2 | 4.90 |
| AV095185 | RIKEN cDNA 2410030A14 gene | 2.73 | 1.2 | 4.90 |
| AV033362 | RIKEN cDNA 1500040F11 gene | 2.73 | 1.3 | 4.90 |
| AW557788 | filamin-like protein | 2.72 | 1.5 | 4.90 |
| BG070952 | RIKEN cDNA 2310024K08 gene | 2.72 | 1.3 | 4.90 |
| AV084361 | RIKEN cDNA 1810036J22 gene | 2.72 | 1.6 | 4.90 |
| BG063730 | ESTs | 2.71 | 1.3 | 4.90 |
| AV086045 | phosphatidylinositol transfer protein | 2.71 | 1.5 | 4.90 |
| BG063539 | ribosomal protein S20 | 2.71 | 1.2 | 4.90 |
| BG072985 | ribosomal protein L7 | 2.71 | 1.3 | 4.90 |
| AV093845 | RIKEN cDNA 2410043G19 gene | 2.71 | 1.6 | 4.90 |
| BG068855 | ribosomal protein L13a | 2.70 | 1.3 | 4.90 |
| BG072570 | ribosomal protein, large P2 | 2.69 | 1.3 | 4.90 |
| AV123125 | lectin, galactose binding, soluble 1 | 2.69 | 2.9 | 4.90 |
| BG072625 | ribosomal protein L19 | 2.68 | 1.4 | 4.90 |
| AV058085 | EST | 2.68 | 1.2 | 4.90 |
| AV008001 | ESTs | 2.68 | 1.5 | 4.90 |
| AA796822 | sialyltransferase 4A (beta-galactosidase alpha-2,3-sialytransferase) | 2.68 | 1.8 | 4.90 |
| W71612 | RAB11b, member RAS oncogene family | 2.68 | 1.5 | 4.90 |
| BG063081 | thymosin, beta 10 | 2.67 | 2.2 | 4.90 |
| AV015233 | ESTs | 2.67 | 2.8 | 4.90 |
| AV061059 | Yamaguchi sarcoma viral (v-yes-1) oncogene homolog | 2.67 | 2.1 | 4.90 |
| AV094452 | dynein, cytoplasmic, light chain 1 | 2.66 | 1.5 | 4.90 |
| AV171729 | EST | 2.66 | 1.3 | 4.90 |
| AV094762 | prenylated SNARE protein | 2.66 | 1.2 | 4.90 |
| AV111434 | transient receptor protein 2 | 2.65 | 1.5 | 4.90 |
| AV020423 | RIKEN cDNA 2900073G15 gene | 2.65 | 1.4 | 4.90 |
| BG064580 | ESTs | 2.65 | 1.3 | 4.90 |
| AV033259 | heterogeneous nuclear ribonucleoprotein methyltransferase-like 2 (*S. cerevisiae*) | 2.65 | 1.5 | 4.90 |
| AV171094 | transcription factor 4 | 2.65 | 1.4 | 4.90 |
| 412427 | EST | 2.64 | 1.7 | 4.90 |
| AV149856 | profilin 1 | 2.64 | 1.5 | 4.90 |
| AV149997 | RIKEN cDNA 5730405M13 gene | 2.63 | 1.4 | 4.90 |
| AV013452 | Expressed sequence AW743884 | 2.63 | 2.4 | 4.90 |
| AV071157 | ESTs | 2.63 | 1.3 | 4.90 |
| AV065302 | membrane-associated protein 17 | 2.63 | 1.3 | 4.90 |
| Downregulated genes in lymphedema vs. normal control (SAM FDR < 0.05). | | | | |
| BG067123 | cadherin 1 | −14.33 | 2.27 | 0.91 |
| BG074458 | RIKEN cDNA 2310076D10 gene | −11.37 | 2.17 | 0.91 |
| AV008967 | ferrochelatase | −10.96 | 1.62 | 0.91 |
| AV068725 | RIKEN cDNA 1200015P04 gene | −9.82 | 1.44 | 0.91 |
| AV030680 | RIKEN cDNA 150031M19 gene | −9.42 | 1.53 | 0.91 |
| AI841373 | latexin | −8.82 | 1.97 | 0.91 |
| BG066932 | *M. musculus*, clone MGC: 11670 IMAGE: 3709076, mRNA, complete cds | −7.61 | 1.60 | 0.91 |
| 411579 | EST | −7.55 | 1.89 | 0.91 |
| AV087499 | EST, moderately similar to A57474 extracellular matrix protein 1 precursor (*M. musculus*) | −7.48 | 1.41 | 0.91 |
| AA607208 | cadherin 1 | −7.45 | 1.59 | 0.91 |
| AV133742 | EST | −7.26 | 1.58 | 0.91 |
| 410895 | EST | −7.20 | 1.75 | 0.91 |
| AV024056 | histindine ammonia lyase | −7.20 | 1.39 | 0.91 |
| 410562 | EST | −6.90 | 1.77 | 0.91 |
| BG069499 | RIKEN cDNA 6330408J20 gene | −6.75 | 1.31 | 0.91 |
| AV017203 | ESTs, highly similar to afadin (*R. norvegicus*) | −6.64 | 1.66 | 0.91 |
| BG066839 | Expressed sequence C80587 | −6.49 | 1.93 | 0.91 |
| 413288 | EST | −6.35 | 2.02 | 0.91 |
| AV080417 | glutathione S-transferase, alpha 4 | −6.20 | 1.73 | 0.91 |
| AV015934 | cyclin D1 | −6.15 | 1.51 | 0.91 |
| AV135760 | RIKEN cDNA 2600017P15 gene | −6.08 | 1.37 | 0.91 |
| AU040403 | Expressed sequence AU040403 | −6.07 | 1.43 | 0.91 |
| BG069581 | ras homolog gene family, member U (*M. musculus*) | −6.07 | 1.49 | 0.91 |
| BG073053 | protein tyrosine phosphatase, receptor type, f polypeptide | −5.77 | 1.42 | 1.08 |
| AI841275 | RIKEN cDNA 2810030L11 gene | −5.67 | 1.78 | 1.08 |
| 412117 | EST | −5.67 | 1.37 | 1.08 |
| AV088691 | *M. musculus*, similar to N-arginine dibasic convertase 1 | −5.63 | 1.43 | 1.08 |
| BG076206 | G protein gamma 3 linked gene | −5.61 | 1.29 | 1.08 |

TABLE 2-continued

| Gene ID | Gene Name | Score (d)a | Fold Change | q-Value (%) |
|---|---|---|---|---|
| AV074612 | CD164 antigen | −5.53 | 1.46 | 1.08 |
| BG072568 | dual specificity phosphatase 14 | −5.52 | 1.43 | 1.08 |
| AV081291 | RIKEN cDNA 1110006I15 gene | −5.46 | 1.59 | 1.08 |
| BG075873 | RIKEN cDNA 2810442O16 gene | −5.44 | 1.86 | 1.08 |
| AA111722 | cyclin D1 | −5.42 | 1.54 | 1.08 |
| AW552727 | fatty acid synthase | −5.36 | 1.71 | 1.08 |
| BG072524 | diacylglycerol O-acyltransferase 2 | −5.35 | 1.87 | 1.08 |
| 412975 | EST | −5.25 | 1.42 | 1.36 |
| AV081155 | Expressed sequence AV228068 | −5.23 | 1.74 | 1.36 |
| BG071790 | protein phosphatase 1, catalytic subunit, gamma isoform | −5.21 | 1.87 | 1.36 |
| AA725946 | keratin complex 1, acidic, gene 5 | −5.15 | 1.87 | 1.36 |
| AV087069 | ras homolog gene family, member U | −5.09 | 1.75 | 1.36 |
| AV085989 | Expressed sequence AU043390 | −5.06 | 1.69 | 1.36 |
| BG071047 | RIKEN cDNA 3110006P09 gene | −5.03 | 1.29 | 1.36 |
| AV006223 | gelsolin | −5.03 | 1.81 | 1.36 |
| AV106079 | Expressed sequence AI173355 | −5.03 | 1.65 | 1.36 |
| AV094491 | RIKEN cDNA 4933411H20 gene | −4.92 | 1.46 | 1.36 |
| AV057616 | ATPase, Hp transporting, lysosomal 34 kDa, V1 subunit D | −4.92 | 1.46 | 1.36 |
| AV084670 | villin 2 | −4.91 | 1.65 | 1.36 |
| BG071281 | leucine aminopeptidase 3 | −4.89 | 1.36 | 1.36 |
| AV022852 | RIKEN cDNA 1110001M24 gene | −4.88 | 1.70 | 1.36 |
| AV005044 | glycolipid transfer protein | −4.88 | 1.47 | 1.36 |
| AW554387 | sphingosine phosphate lyase 1 | −4.88 | 2.03 | 1.36 |
| BG069739 | pre-B cell leukemia transcription factor 1 | −4.87 | 1.53 | 1.36 |
| BG064974 | hydroxysteroid (17-beta) dehydrogenase 12 | −4.85 | 1.50 | 1.36 |
| AV086231 | small proline rich-like 9 | −4.83 | 1.75 | 1.59 |
| 411558 | EST | −4.80 | 1.22 | 1.59 |
| AV032378 | *M. musculus*, similar to hypothetical protein FLJ14466 | −4.75 | 1.52 | 1.59 |
| AV012833 | Expressed sequence AA407887 | −4.74 | 1.14 | 1.59 |
| AV029122 | G protein-coupled receptor 56 | −4.73 | 1.51 | 1.59 |
| BG071157 | phosphate cytidylyltransferase 1, choline, alpha isoform | −4.68 | 1.43 | 1.73 |
| AV088664 | cadherin 1 | −4.65 | 1.77 | 1.73 |
| BG074432 | ESTs, weakly similar to LMA1 laminin alpha-1 chain precursor (*M. musculus*) | −4.65 | 1.64 | 1.73 |
| AV074709 | sterol regulatory element binding factor 1 | −4.63 | 1.86 | 1.73 |
| AV043450 | Erbb2 interacting protein | −4.62 | 1.64 | 1.73 |
| AV036580 | gelsolin | −4.57 | 1.72 | 1.73 |
| BG066848 | Expressed sequence AI429612 | −4.54 | 1.57 | 1.73 |
| AV068741 | Expressed sequence AW538652 | −4.49 | 1.57 | 1.96 |
| BG070160 | Expressed sequence AI447644 | −4.48 | 1.35 | 1.96 |
| 413523 | EST | −4.46 | 1.62 | 1.96 |
| BG072270 | Expressed sequence AU042072 | −4.44 | 1.61 | 1.96 |
| BG075104 | extracellular matrix protein 1 | −4.43 | 1.53 | 1.96 |
| BG076113 | RIKEN cDNA 3110040D16 gene | −4.39 | 1.32 | 1.96 |
| AV087190 | gelsolin | −4.38 | 1.52 | 1.96 |
| AV134202 | molybdenum cofactor synthesis 2 | −4.35 | 1.56 | 2.28 |
| BG076410 | ESTs | −4.34 | 1.51 | 2.28 |
| 411478 | EST | −4.32 | 1.44 | 2.28 |
| 412058 | EST | −4.31 | 1.34 | 2.28 |
| AV143646 | retinoblastoma binding protein 6 | −4.28 | 1.61 | |
| BG069784 | RIKEN cDNA 2310075M16 gene | −4.26 | 1.41 | 2.73 |
| BG062974 | RIKEN cDNA 1110002B05 gene | −4.25 | 1.75 | 2.73 |
| BG075415 | Expressed sequence AW228747 | −4.25 | 1.44 | 2.73 |
| BG064062 | Kruppel-like factor 4 (gut) | −4.23 | 1.83 | 2.73 |
| BG075520 | Expressed sequence AW547365 | −4.18 | 1.26 | 2.73 |
| AV020091 | *M. musculus*, similar to hypothetical protein FLJ20552 | −4.17 | 1.56 | 2.73 |
| BG075034 | histone deacetylase 3 | −4.15 | 1.39 | 2.73 |
| AV057405 | methylenetetrahydrofolate dehydrogenase (NADp dependent), methenyltetrahydrofolate cyclohydrolase | −4.15 | 1.62 | 2.73 |
| BG071256 | RIKEN cDNA 5730469M10 gene | −4.12 | 1.39 | 2.73 |
| AV053048 | Expressed sequence AW493766 | −4.10 | 1.49 | 2.73 |
| BG063086 | RIKEN cDNA 1110002B05 gene | −4.10 | 1.53 | 2.73 |
| AV086552 | ubiquitin-conjugating enzyme E2G 2 | −4.04 | 1.52 | 3.17 |
| AV140482 | *M. musculus*, similar to hypothetical protein, clone MGC: 6903 IMAGE: 2655774 | −4.03 | 1.32 | 3.17 |
| AV085956 | RIKEN cDNA 2310016E22 gene | −4.00 | 1.46 | 3.17 |
| BG063211 | Expressed sequence AA408215 | −3.99 | 1.46 | 3.17 |
| AV059238 | ESTs | −3.98 | 1.50 | 3.17 |
| AV089020 | RIKEN cDNA 2410001H17 gene | −3.95 | 1.42 | 3.17 |
| AW551596 | ESTs, moderately similar to KIAA0874 protein (*H. sapiens*) | −3.95 | 1.44 | 3.17 |

TABLE 2-continued

| Gene ID | Gene Name | Score (d)a | Fold Change | q-Value (%) |
|---|---|---|---|---|
| BG063986 | RIKEN cDNA 4931417M11 gene | −3.94 | 1.36 | 3.17 |
| AU016967 | RIKEN cDNA 4930445G01 gene | −3.94 | 1.43 | 3.17 |
| AV057445 | histone gene complex 2 | −3.94 | 1.92 | 3.17 |
| BG064592 | RIKEN cDNA 9130020C19 gene | −3.93 | 1.64 | 3.17 |
| AV086468 | RIKEN cDNA 2810442O16 gene | −3.90 | 1.65 | 3.24 |
| AV012729 | sterol regulatory element binding factor 1 | −3.90 | 1.60 | 3.24 |
| AV021055 | septin 8 | −3.89 | 1.48 | 3.24 |
| BG074257 | Expressed sequence AU022349 | −3.89 | 1.28 | 3.24 |
| BG063838 | fatty acid synthase | −3.88 | 1.79 | 3.24 |
| AV012338 | RIKEN cDNA 1110058A15 gene | −3.85 | 1.80 | 3.24 |
| AV033310 | synovial sarcoma translocation, Chromosome 18 | −3.82 | 1.34 | 3.24 |
| AV012385 | small proline rich-like 10 | −3.80 | 1.82 | 3.24 |
| AV005017 | sulfotransferase family 4A, member 1 | −3.80 | 1.42 | 3.24 |
| AV084927 | M. musculus SH3GLB2 mRNA, complete cds | −3.79 | 1.45 | 3.24 |
| AV133665 | DnaJ (Hsp40) homolog, subfamily B, member 1 | −3.79 | 1.63 | 3.24 |
| BG063266 | glutamate-cysteine ligase, catalytic subunit | −3.78 | 1.27 | 3.24 |
| BG075637 | neurofibromatosis 2 | −3.78 | 1.25 | 3.24 |
| BG063956 | M. musculus, eukaryotic translation termination factor 1, clone MGC: 18745 IMAGE: 3992883 | −3.78 | 1.31 | 3.24 |
| BG072153 | malic enzyme, supernatant | −3.77 | 1.72 | 3.24 |
| AV084064 | ATPase, class II, type 9A | −3.76 | 1.64 | 3.53 |
| BG065176 | M. musculus, clone IMAGE: 4038329, mRNA, partial cds | −3.73 | 1.59 | 3.53 |
| BG074922 | ring finger protein 167 | −3.71 | 1.29 | 3.53 |
| BG075099 | retinoblastoma binding protein 6 | −3.68 | 1.55 | 3.53 |
| BG075709 | RIKEN cDNA 2610206B05 gene | −3.67 | 1.49 | 3.53 |
| BG072411 | erythrocyte protein band 4 1-like 4b | −3.66 | 1.51 | 3.53 |
| AV085951 | calmodulin 4 | −3.65 | 1.30 | 3.53 |
| AV041686 | RPB5-mediating protein | −3.64 | 1.79 | 3.53 |
| BG063540 | pantophysin | −3.63 | 1.32 | 3.73 |
| BG063290 | nuclear factor, erythroid-derived 2-like 1 | −3.62 | 1.38 | 3.73 |
| AF249870 | p53 apoptosis effector related to Pmp22 | −3.62 | 1.30 | 3.73 |
| AV013952 | RIKEN cDNA 1300007F04 gene | −3.62 | 1.53 | 3.73 |
| AV065655 | RIKEN cDNA 1200015P04 gene | −3.60 | 1.61 | 3.73 |
| BG074645 | ESTs, moderately similar to T42707 hypothet. protein DKFZp586EO41.1 (H. sapiens) | −3.59 | 1.44 | 3.73 |
| BG063778 | dystroglycan 1 | −3.58 | 1.30 | 3.73 |
| AV015196 | Expressed sequence AI195353 | −3.58 | 1.81 | 3.73 |
| BG068048 | Hypothetical protein, clone MTA.D02.090 | −3.57 | 1.38 | 3.73 |
| AV034519 | 3-hydroxy-3-methylglutaryl-coenzyme A reductase | −3.54 | 1.48 | 3.73 |
| AU020667 | ubiquitin carboxyl-terminal esterase L3 (ubiquitin thiolesterase) | −3.54 | 1.31 | 3.73 |
| AV094982 | regulator of G-protein signaling 19 interacting protein 1 | −3.54 | 1.50 | 3.73 |
| AA106674 | RIKEN cDNA 2310046A13 gene | −3.53 | 1.50 | 3.73 |
| BG070746 | RIKEN cDNA 1110067D22 gene | −3.51 | 1.48 | 3.74 |
| BG064041 | RIKEN cDNA 0610011N22 gene | −3.49 | 1.34 | 3.74 |
| AV049386 | RIKEN cDNA 0610039C21 gene | −3.49 | 1.44 | 3.74 |
| AI840878 | RIKEN cDNA 1200015P04 gene | −3.49 | 1.54 | 3.74 |
| AV105934 | sphingosine kinase 1 | −3.47 | 1.68 | 3.74 |
| AV085893 | Expressed sequence AU043990 | −3.47 | 1.62 | 3.74 |
| AA118482 | endothelial differentiation, lysophosphatidic acid G-protein-coupled receptor 4 | −3.45 | 1.25 | 3.74 |
| BG063967 | M. musculus, clone MGC: 7094 IMAGE: 3157493, mRNA, complete cds | −3.44 | 1.48 | 3.74 |
| AV031353 | M. musculus, similar to phosphatidylserine decarboxylase, clone MGC: 7133 IMAGE: 3158145 | −3.44 | 1.70 | 3.74 |
| AV162240 | interferon regulatory factor 3 | −3.43 | 1.24 | 4.03 |
| AV162274 | RIKEN cDNA 3110001I20 gene | −3.42 | 1.92 | 4.03 |
| BG072974 | ESTs | −3.40 | 1.53 | 4.03 |
| AV005287 | secretory carrier membrane protein 2 | −3.37 | 1.19 | 4.03 |
| AV089034 | Expressed sequence AI316859 | −3.37 | 1.41 | 4.03 |
| BG069319 | Expressed sequence AA415431 | −3.37 | 1.61 | 4.03 |
| AV087585 | neighbor of Cox4 | −3.36 | 1.35 | 4.03 |
| AA863549 | Notch gene homolog 1 (Drosophila) | −3.36 | 2.07 | 4.03 |
| BG075813 | homeodomain interacting protein kinase 1 | −3.36 | 1.38 | 4.03 |
| BG075318 | RIKEN cDNA 4933429H19 gene | −3.35 | 1.29 | 4.03 |
| AV024434 | RIKEN cDNA 1200003E16 gene | −3.35 | 1.66 | 4.03 |
| BG074608 | RIKEN cDNA 1300009F09 gene | −3.34 | 1.41 | 4.03 |
| AV084667 | tuftelin 1 | −3.33 | 1.56 | 4.03 |
| AV087829 | chloride intracellular channel 3 | −3.33 | 1.72 | 4.03 |
| BG063343 | 7-dehydrocholesterol reductase | −3.33 | 1.65 | 4.03 |

TABLE 2-continued

| Gene ID | Gene Name | Score (d)a | Fold Change | q-Value (%) |
|---|---|---|---|---|
| AV052668 | RIKEN cDNA 1810018L05 gene | −3.32 | 1.51 | 4.03 |
| AI194827 | oxysterol binding protein-like 1A | −3.31 | 1.80 | 4.03 |
| 410847 | EST | −3.31 | 1.41 | 4.28 |
| AV093444 | hypothetical protein, MNCb-1213 | −3.29 | 1.25 | 4.28 |
| BG076201 | villin 2 | −3.29 | 1.29 | 4.28 |
| AV021431 | ESTs | −3.29 | 1.39 | 4.28 |
| BG072487 | RIKEN cDNA 3110118K12 gene | −3.27 | 1.37 | 4.28 |
| AV084649 | LIM domain binding 1 | −3.27 | 1.36 | 4.28 |
| AV081983 | RIKEN cDNA 1200015P04 gene | −3.27 | 1.51 | 4.28 |
| AV055811 | UDP-galactose translocator 2 | −3.26 | 1.22 | 4.28 |
| BG075832 | cyclin D2 | −3.26 | 1.50 | 4.28 |
| 413170 | EST | −3.24 | 1.38 | 4.28 |
| BG070048 | homeodomain interacting protein kinase 1 | −3.24 | 1.30 | 4.28 |
| AV040013 | Expressed sequence C85469 | −3.23 | 1.36 | 4.28 |
| AV084288 | small proline rich-like 2 | −3.22 | 1.60 | 4.90 |
| AV093474 | RIKEN cDNA 1300009F09 gene | −3.19 | 1.35 | 4.90 |
| AV149993 | ring finger protein 167 | −3.19 | 1.49 | 4.90 |
| 411517 | EST | −3.18 | 1.36 | 4.90 |
| BG075876 | ATPase, class II, type 9A | −3.18 | 1.31 | 4.90 |
| BG075368 | *M. musculus*, similar to CGI-67 protein, clone MGC: 11699 IMAGE: 3964094, mRNA, complete cds | −3.17 | 1.48 | 4.90 |
| 410554 | EST | −3.17 | 1.43 | 4.90 |
| BG071335 | RIKEN cDNA 5730469M10 gene | −3.16 | 1.54 | 4.90 |
| BG074934 | RIKEN cDNA 2810037C14 gene | −3.16 | 1.42 | 4.90 |
| BG063413 | CD2 antigen (cytoplasmic tail) binding protein 2 | −3.14 | 1.32 | 4.90 |

TABLE 3

Pathway analysis for up-regulated genes in Lymphedema vs. normal control (SAM FDR < 0.05).

| System | Gene Category | List Hits | List Total | Population Hits | Population Total | p-Value | Unigene Clusters |
|---|---|---|---|---|---|---|---|
| GO Biological Process | Response to pest/pathogen/parasite | 11 | 101 | 252 | 10,778 | 0.0001 | MM.163; MM.2128; MM.22673; MM.23905; MM.249934; MM.2570; MM.3453; MM.45436; MM.465; MM.653; MM.8655 |
| | Immune response | 14 | 101 | 451 | 10,778 | 0.0003 | MM.141021; MM.163; MM.1776; MM.2128; MM.22673; MM.23905; MM.249934; MM.2570; MM.3453; MM.45436; MM.465; MM.549; MM.653; MM.8655 |
| | Response to stress | 15 | 101 | 538 | 10,778 | 0.0004 | MM.1090; MM.12145; MM.163; MM.203; MM.2128; MM.22673; MM.23905; MM.249934; MM.2570; MM.29057; MM.3453; MM.45436; MM.465; MM.653; MM.8655 |
| | Response to biotic stimulus | 16 | 101 | 606 | 10,778 | 0.0004 | MM.1090; MM.141021; MM.163; MM.1776; MM.2128; MM.22673; MM.23905; MM.249934; MM.2570; MM.29865; MM.3453; MM.45436; MM.465; MM.549; MM.653; MM.8655 |
| | Defense response | 15 | 101 | 553 | 10,778 | 0.0006 | MM.141021; MM.163; MM.1776; MM.2128; MM.22673; MM.23905; MM.249934; MM.2570; MM.29865; MM.3453; MM.45436; MM.465; MM.549; MM.653; MM.8655 |
| | Complement activation | 4 | 101 | 36 | 10,778 | 0.0044 | MM.2570; MM.3453; MM.653; MM.8655 |
| | Humoral immune response | 5 | 101 | 76 | 10,778 | 0.0054 | MM.2570; MM.3453; MM.45436; MM.653; MM.8655 |
| | Humoral defense mechanism (sensu Vertebrata) | 4 | 101 | 42 | 10,778 | 0.0068 | MM.2570; MM.3453; MM.653; MM.8655 |
| | Nicotinamide metabolism | 3 | 101 | 14 | 10,778 | 0.0072 | MM.21454; MM.29182; MM.4222 |
| | Pyridine nucleotide metabolism | 3 | 101 | 15 | 10,778 | 0.0083 | MM.21454; MM.29182; MM.4222 |
| | Oxidoreduction coenzyme metabolism | 3 | 101 | 17 | 10,778 | 0.0106 | MM.21454; MM.29182; MM.4222 |
| | Carbohydrate metabolism | 8 | 101 | 304 | 10,778 | 0.0228 | MM.14825; MM.180337; MM.21743; MM.2284; MM.29182; MM.29357; MM.4222; MM.45436 |
| | Water-soluble vitamin metabolism | 3 | 101 | 30 | 10,778 | 0.0313 | MM.21454; MM.29182; MM.4222 |
| | Response to external stimulus | 17 | 101 | 1,070 | 10,778 | 0.0370 | MM.1090; MM.141021; MM.163; MM.1776; MM.196464; MM.2128; MM.22673; MM.23905; MM.249934; MM.2570; MM.29865; MM.3453; MM.45436; MM.465; MM.549; MM.653; MM.8655 |

TABLE 3-continued

Pathway analysis for up-regulated genes in Lymphedema vs. normal control (SAM FDR < 0.05).

| System | Gene Category | List Hits | List Total | Population Hits | Population Total | p-Value | Unigene Clusters |
|---|---|---|---|---|---|---|---|
| | Main pathways of carbohydrate metabolism | 4 | 101 | 80 | 10,778 | 0.0381 | MM.14825; MM.21743; MM.29182; MM.4222 |
| GO Cellular Component | Extracellular space | 42 | 112 | 2,198 | 10,767 | 0.0000 | MM.10299; MM.10406; MM.141312; MM.163; MM.17185; MM.172; MM.181021; MM.182434; MM.18625; MM.19844; MM.2128; MM.21767; MM.22194; MM.22673; MM.22699; MM.2277; MM.23905; MM.2412; MM.2570; MM.2608; MM.27343; MM.28231; MM.28484; MM.29599; MM.29778; MM.3014; MM.3453; MM.36661; MM.41560; MM.43831; MM.45436; MM.46053; MM.465; MM.549; MM.653; MM.7091; MM.7281; MM.738; MM.8655; MM.86922; MM.9537; MM.980 |
| | Collagen | 5 | 112 | 34 | 10,767 | 0.0004 | MM.10299; MM.141312; MM.181021; MM.7281; MM.738 |
| | Mitochondrion | 17 | 112 | 618 | 10,767 | 0.0006 | MM.10406; MM.1090; MM.14825; MM.18625; MM.20801; MM.21454; MM.215667; MM.2159; MM.21743; MM.24108; MM.251621; MM.29057; MM.29599; MM.30072; MM.3014; MM.400; MM.8688 |
| | Cytoplasm | 55 | 112 | 3,659 | 10,767 | 0.0009 | MM.10406; MM.1090; MM.121878; MM.141741; MM.142095; MM.142729; MM.14825; MM.153911; MM.17185; MM.181880; MM.18625; MM.196484; MM.20801; MM.21454; MM.215667; MM.2159; MM.21743; MM.2241; MM.2277; MM.2284; MM.24108; MM.2412; MM.24608; MM.249934; MM.251621; MM.2551; MM.260084; MM.2734; MM.28100; MM.28622; MM.28693; MM.29057; MM.29182; MM.29357; MM.29599; MM.29997; MM.30072; MM.3014; MM.34246; MM.3532; MM.3746; MM.38055; MM.400; MM.4024; MM.41560; MM.4222; MM.42790; MM.6523; MM.686; MM.7091; MM.741; MM.757; MM.831; MM.83909; MM.8688 |
| | Mitochondrial matrix | 4 | 112 | 64 | 10,767 | 0.0282 | MM.14825; MM.21743; MM.24108; MM.29599 |
| | Collagen type V | 2 | 112 | 3 | 10,767 | 0.0306 | MM.10299; MM.7281 |
| | Mitochondrial membrane | 6 | 112 | 174 | 10,767 | 0.0339 | MM.10406; MM.18625; MM.251621; MM.29057; MM.3014; MM.400 |
| | Mitochondrial electron transport chain | 3 | 112 | 32 | 10,767 | 0.0427 | MM.251621; MM.3014; MM.400 |
| GO Molecular Function | Defense/immunity protein activity | 9 | 109 | 129 | 11,303 | 0.0000 | MM.141741; MM.1776; MM.2570; MM.28231; MM.3453; MM.45436; MM.465; MM.653; MM.8655 |
| | Extracellular matrix structural | 6 | 109 | 68 | 11,303 | 0.0005 | MM.10299; MM.141312; MM.181021; MM.29865; MM.7281; MM.738 |
| | Complement activity | 4 | 109 | 24 | 11,303 | 0.0015 | MM.2570; MM.3453; MM.653; MM.8655 |
| | Structural molecule activity | 14 | 109 | 591 | 11,303 | 0.0041 | MM.10299; MM.107869; MM.121878; MM.141312; MM.181021; MM.24108; MM.29057; MM.29599; MM.29865; MM.29982; MM.42790; MM.686; MM.7281; MM.738 |
| | Actin binding | 7 | 109 | 179 | 11,303 | 0.0073 | MM.121878; MM.141741; MM.142729; MM.153911; MM.30059; MM.3532; MM.4024 |
| | Heparin binding | 4 | 109 | 47 | 11,303 | 0.0101 | MM.182434; MM.23905; MM.46053; MM.7281 |
| | Isomerase activity | 5 | 109 | 100 | 11,303 | 0.0153 | MM.2412; MM.28100; MM.28622; MM.29357; MM.4222 |
| | Antimicrobial peptide activity | 3 | 109 | 22 | 11,303 | 0.0184 | MM.141741; MM.28231; MM.45436 |
| | Glycosaminoglycan binding | 4 | 109 | 59 | 11,303 | 0.0187 | MM.182434; MM.23905; MM.46053; MM.7281 |
| | Structural constituent of muscle | 3 | 109 | 28 | 11,303 | 0.0291 | MM.121878; MM.29057; MM.686 |
| | Electron transporter activity | 6 | 109 | 181 | 11,303 | 0.0296 | MM.10406; MM.21062; MM.28622; MM.30072; MM.38746; MM.8688 |
| | Cytoskeletal protein binding | 7 | 109 | 248 | 11,303 | 0.0315 | MM.121878; MM.141741; MM.142729; MM.153911; MM.30059; MM.3532; MM.4024 |
| | Hydrolase activity, acting on glycosyl bonds | 4 | 109 | 82 | 11,303 | 0.0436 | MM.180337; MM.203; MM.2284; MM.45436 |
| | Oxidoreductase activity, acting on the CH—OH group of donors, NAD, or NADP as acceptor | 4 | 109 | 86 | 11,303 | 0.0491 | MM.14825; MM.21454; MM.21743; MM.28100 |

TABLE 4

Pathway analysis for down-regulated genes in Lymphedema vs. normal control (SAM FDR < 0.05).

| System | Gene Category | List Hits | List Total | Population Hits | Population Total | p-Value | Unigene Clusters |
|---|---|---|---|---|---|---|---|
| GO Biological Process | Lipid metabolism | 8 | 47 | 394 | 10,778 | 0.001 | MM.180189; MM.200373; MM.209300; MM.22505; MM.259976; MM.3195; MM.4141; MM.61526 |
| | Coenzyme and prosthetic group metabolism | 5 | 47 | 123 | 10,078 | 0.002 | MM.19027; MM.27082; MM.30206; MM.61526; MM.6743 |
| | Biosynthesis | 11 | 47 | 874 | 10,078 | 0.003 | MM.180189; MM.19027; MM.209300; MM.22505; MM.23951; MM.27082; MM.30206; MM.3845; MM.4141; MM.61526; MM.6743 |
| | Lipid biosynthesis | 5 | 47 | 152 | 10,778 | 0.004 | MM.180189; MM.209300; MM.22505; MM.4141; MM.61526 |
| | Coenzyme metabolism | 4 | 47 | 106 | 10,778 | 0.010 | MM.19027; MM.27082; MM.30206; MM.61526 |
| | Steroid biosynthesis | 3 | 47 | 58 | 10,778 | 0.025 | MM.22505; MM.4141; MM.61526 |
| | Metabolism | 31 | 47 | 5,384 | 10,778 | 0.026 | MM.10288; MM.158107; MM.180189; MM.181852; MM.19027; MM.200373; MM.202360; MM.20521; MM.20827; MM.209300; MM.220922; MM.22505; MM.23784, MM.23951; MM.2478; MM.259976; MM.26973; MM.27082; MM.27227; MM.29352; MM.30206; MM.3195; MM.34173; MM.35605; MM.3845; MM.4141; MM.42249; MM.5831; MM.61526; MM.6743; MM.9745 |
| | Physiological process | 42 | 47 | 8,273 | 10,778 | 0.028 | MM.10288; MM.158107; MM.180189; MM.181852; MM.19027; MM.200373; MM.202360; MM.20521; MM.20827; MM.209300; MM.21109; MM.218875; MM.220922; MM.221298; MM.22505; MM.23784; MM.23951; MM.2478; MM.259976; MM.2632; MM.26973; MM.27082; MM.27227; MM.29352; MM.29802; MM.30195; MM.30206; MM.3195; MM.34173; MM.3433; MM.35605; MM.3845; MM.38868; MM.4141; MM.42249; MM.4480; MM.46716; MM.5181; MM.5831; MM.61526; MM.6743; MM.9745 |
| | Macromolecule biosynthesis | 8 | 47 | 731 | 10,778 | 0.034 | MM.180189; MM.209300; MM.22505; MM.27082; MM.30206; MM.3845; MM.4141; MM.61526 |
| GO Molecular Function | Catalytic activity | 25 | 47 | 4,007 | 11,303 | 0.015 | MM.10288; MM.158107; MM.180189; MM.200373; MM.200924; MM.202360; MM.20521; MM.20827; MM.209300; MM.22505; MM.23784; MM.23951; MM.2478; MM.2632; MM.27082; MM.27227; MM.29352; MM.29802; MM.29998; MM.30206; MM.3195; MM.42249; MM.5831; MM.61526; MM.9745 |

TABLE 5

Functional gene expression analysis in experimental lymphedema.

Acute Inflammation

| UPREGULATED | Fold | Q (%) | DOWNREGULATED | Fold | Q (%) |
|---|---|---|---|---|---|
| calgranulin B | 22.5:1 | 2.729 | sphingosine kinase 1 | 0.6:1 | 3.743 |
| S100 calcium binding protein A11 | 1.6:1 | 1.084 | gelsolin | 0.6:1 | 1.360 |
| tenascin C | 7.8:1 | 0.913 | | | |
| lipocalin | 6.1:1 | 0.913 | | | |
| stefin A3 | 4.3:1 | 0.913 | | | |
| proteoglycan, secretory granule | 3.7:1 | 3.532 | | | |
| L-plastin 2 | 3.3:1 | 1.084 | | | |
| follistatin | 3.2:1 | 1.084 | | | |
| procollagen type IV | 3.0:1 | 2.729 | | | |
| arachidonate 5-lipoxygenase activating protein | 2.9:1 | 1.587 | | | |
| stromal cell-derived factor 1 | 2.5:1 | 0.913 | | | |
| thymosin beta 10 | 2.5:1 | 1.587 | | | |
| ferritin light chain 1 | 2.4:1 | 2.729 | | | |
| legumain | 2.4:1 | 1.084 | | | |
| cathepsin C | 2.3:1 | 1.587 | | | |
| cathepsin Z | 2.2:1 | 1.084 | | | |
| cathepsin H | 1.4:1 | 1.587 | | | |
| cathepsin L | 1.5:1 | 4.279 | | | |
| glutathione peroxidase 1 | 1.9:1 | 1.084 | | | |
| platelet factor 4 | 1.9:1 | 1.084 | | | |
| lymphocyte specific 1 | 1.8:1 | 1.084 | | | |
| basigin | 1.7:1 | 4.029 | | | |
| thymosin beta 4 | 1.7:1 | 3.238 | | | |
| CD63 antigen | 1.5:1 | 3.730 | | | |

TABLE 5-continued

Functional gene expression analysis in experimental lymphedema.

Acute Inflammation

| UPREGULATED | Fold | Q (%) | DOWNREGULATED | Fold | Q (%) |
|---|---|---|---|---|---|
| nuclear factor of kappa light chain gene enhancer in B-cells 1, p105 | 1.5:1 | 4.279 | | | |
| peptidylprolyl isomerase B | 1.4:1 | 1.587 | | | |
| prosaposin | 1.4:1 | 3.532 | | | |
| LPS-induced TNF-α factor | 1.3:1 | 4.029 | | | |
| nascent polypeptide associated complex alpha polypeptide | 1.3:1 | 3.743 | | | |

Immune

| UPREGULATED | Fold | Q (%) | DOWNREGULATED | Fold | Q (%) |
|---|---|---|---|---|---|
| lipocalin | 6.1:1 | 0.913 | oxysterol binding protein-like 1A | 0.6:1 | 4.029 |
| cytotoxic T lymphocyte associated protein 2α | 4.5:1 | 0.913 | villin 2 | 0.6:1 | 1.360 |
| Fc receptor, IgE, high affinity I, γ polypeptide | 4.2:1 | 0.913 | dual specificity phosphatase 14 (MAPK6) | 0.7:1 | 1.084 |
| Beta 2 microglobulin | 3.9:1 | 0.913 | nuclear factor 2 | 0.7:1 | 3.730 |
| lectin, galactose binding, soluble 1 | 2.9:1 | 2.276 | CD2 Antigen-binding protein 2 | 0.8:1 | 4.903 |
| legumain | 2.4:1 | 1.084 | interferon regulatory factor 3 | 0.8:1 | 4.029 |
| cathepsin C | 2.3:1 | 1.587 | | | |
| cathepsin Z | 2.2:1 | 1.084 | | | |
| cathepsin H | 1.4:1 | 1.587 | | | |
| cathepsin L | 1.5:1 | 4.279 | | | |
| interferon gamma receptor | 2.0:1 | 0.913 | | | |
| lymphocyte specific 1 | 1.8:1 | 1.084 | | | |
| granulin | 1.7:1 | 1.084 | | | |
| interferon induced transmembrane protein 3-like | 1.7:1 | 1.961 | | | |
| zinc finger protein 100 | 1.6:1 | 2.276 | | | |
| lymphocyte antigen 6 complex, locus E | 1.6:1 | 2.729 | | | |
| interferon (alpha and beta) receptor 2 | 1.5:1 | 4.279 | | | |

Complement Cascade

| UPREGULATED | Fold | Q (%) | | | |
|---|---|---|---|---|---|
| histocompatibility 2, complement component factor B | 3.1:1 | 3.238 | | | |
| complement component 1, q subcomponent, c polypeptide | 2.6:1 | 0.913 | | | |
| calreticulin | 2.0:1 | 1.727 | | | |
| serine (or cysteine) proteinase inhibitor, clade I (neuroserpin), member 1 | 2.0:1 | 3.165 | | | |

Wound healing and fibrosis

| UPREGULATED | Fold | Q (%) | | | |
|---|---|---|---|---|---|
| tenascin C | 7.8:1 | 0.913 | | | |
| lipocalin | 6.1:1 | 0.913 | | | |
| lysyl oxidase | 2.7:1 | 1.727 | | | |
| biglycan | 2.6:1 | 3.165 | | | |
| thymosin beta 10 | 2.5:1 | 1.587 | | | |
| procollagen, type V, alpha 2 | 2.4:1 | 3.730 | | | |
| fibulin 2 | 2.0:1 | 1.084 | | | |
| sorting nexin 5 | 2.0:1 | 1.084 | | | |
| platelet factor 4 | 1.9:1 | 1.084 | | | |
| actin, alpha 2, smooth muscle, aorta | 1.7:1 | 4.279 | | | |
| granulin | 1.7:1 | 1.084 | | | |
| S100 calcium binding protein A11 | 1.6:1 | 1.084 | | | |

Stress response

| UPREGULATED | Fold | Q (%) | DOWNREGULATED | Fold | Q (%) |
|---|---|---|---|---|---|
| selenoprotein P | 2.8:1 | 2.276 | sterol regulatory element binding factor 1 | 0.5:1 | 1.727 |
| selenoprotein K | 1.3:1 | 3.743 | 7-dehydrocholesterol reductase | 0.6:1 | 4.029 |

TABLE 5-continued

Functional gene expression analysis in experimental lymphedema.

Acute Inflammation

| UPREGULATED | Fold | Q (%) | DOWNREGULATED | Fold | Q (%) |
|---|---|---|---|---|---|
| selenoprotein W, muscle 1 | 2.2:1 | 4.903 | DnaJ (Hsp40) homolog, subfamily B, member 1 | 0.6:1 | 3.238 |
| DnaJ (Hsp40) homolog, subfamily B, member 5 | 2.7:1 | 3.532 | malic enzyme, supernatant | 0.6:1 | 3.238 |
| ferritin light chain 1 | 2.4:1 | 2.729 | methylenetetrahydrofolate dehydrogenase (NAD+ dependent), methenyltetrahydrofolate cyclohydrolase | 0.6:1 | 2.729 |
| fibulin 2 | 2.0:1 | 1.084 | glutathione S transferase, alpha 4 | 0.6:1 | 0.913 |
| glutathione peroxidase 1 | 1.9:1 | 1.084 | Hydroxysteroid (17-beta) dehydrogenase 12 | 0.7:1 | 1.360 |
| platelet factor 4 | 1.9:1 | 1.084 | | | |
| carbonyl reductase 2 | 1.8:1 | 1.084 | | | |
| glyceraldehyde 3-phosphate dehydrogenase | 1:6:1 | 3.730 | | | |
| heme oxygenase (decycling) 1 | 1.6:1 | 0.913 | | | |
| thioredoxin 1 | 1.6:1 | 3.730 | | | |
| chaperonin 10 (heat shock protein 1) | 1.5:1 | 3.730 | | | |
| heat shock 70 kD protein 8 | 1.5:1 | 4.029 | | | |
| superoxide dismutase 2 | 1.5:1 | 3.165 | | | |
| heat shock protein, 70 kDa 2 | 1.4:1 | 4.279 | | | |
| heat shock protein, 30 kDa | 1.3:1 | 3.743 | | | |
| transaldolase 1 | 1.3:1 | 4.279 | | | |

Angiogenesis

| | | | | | |
|---|---|---|---|---|---|
| thymosin beta 10 | 2.5:1 | 1.587 | | | |
| hypoxia inducible factor 1, alpha subunit | 1.9:1 | 1.961 | | | |
| triosephosphate isomerase | 1.9:1 | 1.727 | | | |
| SRY-box containing gene 18 (SOX18) | 1.8:1 | 4.029 | | | |
| endomucin | 1.7:1 | 1.084 | | | |
| fibroblast growth factor binding protein | 1.5:1 | 2.276 | | | |

Cytoskeletal

| | | | | | |
|---|---|---|---|---|---|
| caldesmon 1 | 3.1:1 | 3.743 | | | |
| thymosin beta 10 | 2.5:1 | 1.587 | | | |
| actinin, alpha 1 | 1.8:1 | 2.729 | | | |
| calcium regulated heat stable protein 1 | 1.8:1 | 1.961 | | | |
| t-complex testis expressed 1 | 1.8:1 | 3.165 | | | |
| actin, alpha 2, smooth muscle, aorta | 1.7:1 | 4.279 | | | |
| actin, beta, cytoplasmic | 1.4:1 | 3.532 | | | |
| basigin | 1.7:1 | 4.029 | | | |
| capping protein beta 1 | 1.7:1 | 1.961 | | | |
| cofilin 1 | 1.7:1 | 4.029 | | | |
| zyxin | 1.6:1 | 3.743 | | | |
| actin related protein 2/3 complex, subunit 4 | 1.5:1 | 1.727 | | | |
| filamin-like | 1.5:1 | 4.903 | | | |
| profilin 1 | 1.5:1 | 4.903 | | | |
| transgelin | 1.5:1 | 2.729 | | | |
| ribosomal protein S18 | 1.2:1 | 1.961 | | | |

Wnt Pathway

| | | | | | |
|---|---|---|---|---|---|
| tenascin C | 7.8:1 | 0.913 | Cadherin 1 | 0.4:1 | 0.913 |
| receptor tyrosine kinase-like orphan receptor 2 | 1.7:1 | 1.587 | Notch gene homolog 1, (Drosophila) | 0.5:1 | 4.029 |

Adipogenesis

| | | | | | |
|---|---|---|---|---|---|
| fatty acid binding protein 5, epidermal | 2.2:1 | 2.729 | diacylglycerol acyltransferase 2 | 0.5.1 | 1.084 |
| sorting nexin 5 | 2.0:1 | 1.084 | 7-dehydrocholesterol reductase | 0.6:1 | 4.029 |

TABLE 5-continued

Functional gene expression analysis in experimental lymphedema.

Acute Inflammation

| UPREGULATED | Fold | Q (%) | DOWNREGULATED | Fold | Q (%) |
|---|---|---|---|---|---|
| esterase 10 | 1.9:1 | 1.084 | fatty acid synthase | 0.6:1 | 3.238 |
| SRY-box containing gene 18 (SOX 18) | 1.8:1 | 4.029 | 3-hydroxy-3-methylglutaryl Coenzyme A reductase | 0.7:1 | 3.730 |
| coactosin | 1.3:1 | 1.587 | | | |

Example 2

Molecular Profiling of Human Lymphedema

Paired whole genome transcriptional profiling was performed using the Agilent human array (n=30). Expression profiles of untreated and post-treated lymphedemous tissue were compared to the normal cutaneous RNA from the same subject.

Figure 7:
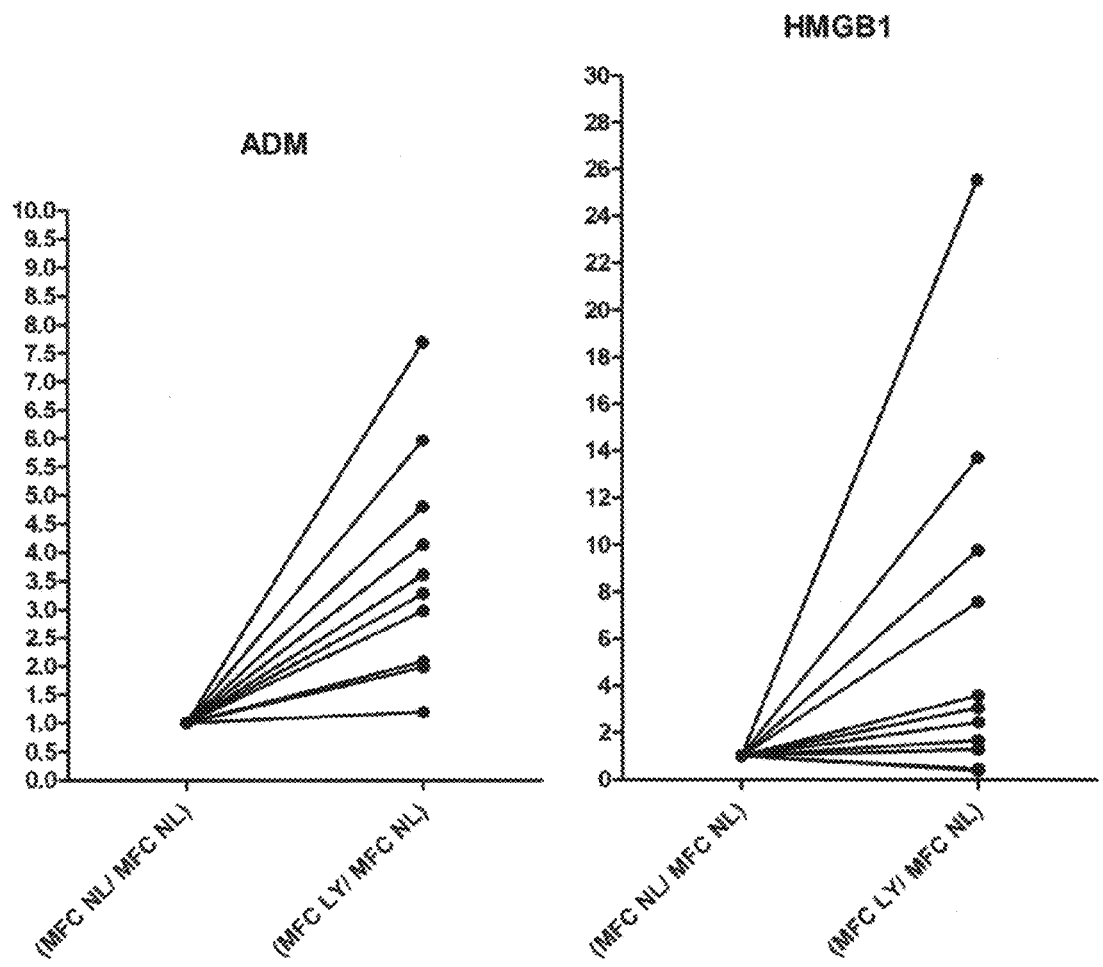
FIG. 7. Quantitative real-time RT-PCR confirmation of the results of microarray hybridization of human tissue. Representative examples of qRT-PCR results for genes identified in Example 2 below are provided. ADM: adrenomedullin. HMGB1: high mobility group box 1. "MFC NL/MFC NL": expression in unaffected tissue normalized to expression in unaffected tissue. "MFC LY/MFC NL": expression in lymphedemous tissue normalized to expression in unaffected tissue.

The expression of 8431 of the genes assayed was altered in lymphedema versus normal tissue (p≤0.02; 1309 of these genes significant at p≤0.001; 313 genes significant at p≤$10^{-5}$). 6050 of the 8431 genes (72%) displayed directional normalization after ketoprofen treatment. Table 6 (below) provides a list of genes that were identified in the screen that encode secreted or cell surface proteins that are statistically significantly upregulated in lymphedemous tissue and thus may be used to diagnose lymphedema in an individual. Quantitative RT-PCR was used to validate microarray results; representative examples of results are provided in FIG. 7.

TABLE 6

Genes of particular interest identified by molecular profiling of human lymphedema.

| Gene of Interest | Abbreviated Gene Name | Cellular location | Refseq No. |
|---|---|---|---|
| VGL high density lipoprotein binding protein | HDLBP | cytoplasm | NM_005336 |
| Pentraxin 3 (pentraxin-related gene) | PTX3 | secreted | NM_002852 |
| Tumor Necrosis Factor Receptor superfamily, member 9 | TNFRSF9 | integral membrane protein | NM_001561 |
| Phospholipase A2, group sPLA2S IID | PLA2G2D | secreted | NM_012400 |
| Kallikrein-related peptidase 3(Prostrate-specific antigen) | KLK3; Aps; PSA | secreted | NM_001030047 |
| Chromogranin A, parathyroid secretory protein 1 | CGA | secreted | NM_000735 |
| Adrenomedullin | Adm | secreted | NM_001124 |
| Angiopoietin 1 | ANGPT1, agpT | secreted | NM_001146 |
| Angiopoietin 2 | ANGPT2 | secreted | NM_001147 |
| Angiopoietin 2B | | secreted | NM_001118887 |
| Angiopoietin-like 7 | ANGPTL7 | secreted | NM_021146 |
| Lipoprotein, Lp(a) | APOA | secreted | NM_005577 |
| Apolipoprotein A-I | APOA1 | secreted | NM_000039 |
| Apolipoprotein A-IV | APOA4 | secreted | NM_000482 |
| APOBEC1 Complementation Factor | A1CF; APOBEC1 CF | no | NM_001198818 |
| ADAM Metallopeptidase with Thrombospondin type 1motif, 13 | MGC118900 | matrix | NM_139025 |
| Cardiotrophin 1 | ct1 | secreted | NM_001142544 |
| carcinoembryonic antigen-related cell adhesion molecule 1 (biliary glycoprotein) | BGPa | integral membrane protein | NM_001024912 |
| interleukin 13 | IL-13; Bhr1 | secreted | NM_002188 |
| cytokine-like 1 | CYTL1; C17 | secreted | NM_018659 |
| complement component 8, alpha polypeptide | C8A | integral membrane protein | NM_000562 |
| chromogranin A (parathyroid secretory protein 1) | CHGA | secreted | NM_001275 |
| chymotrypsinogen B2 | CTRB2 | secreted | NM_001025200 |
| chemokine (C—X—C motif) ligand 17 | CXCL17 | secreted | NM_198477 |

TABLE 6-continued

Genes of particular interest identified by molecular profiling of human lymphedema.

| Gene of Interest | Abbreviated Gene Name | Cellular location | Refseq No. |
|---|---|---|---|
| alpha-2-HS-glycoprotein | AHSG; fetua | matrix | NM_001622 |
| fibroblast growth factor 10 | FGF10 | matrix co-localization | NM_004465 |
| leptin | LEP; FLJ94114 | secreted | NM_000230 |
| complement component 1, q subcomponent-like 1 | crf | "extracellular" and "collagen" | NM_006688 |
| bactericidal/permeability-increasing protein | BPI | integral membrane protein | NM_001725 |
| bone morphogenetic protein 10 | BMP10 | z disk | NM_014482 |
| immunoglobulin kappa variable 4-1 | B3 | secreted | CAA77318 |
| interleukin 24 | FISP | secreted | NM_001185156 |
| chemokine (C-C motif) ligand 25 | CCL25 | secreted | NM_001201359 |
| apolipoprotein D | APOD | secreted, intracellular | NM_001647 |
| apolipoprotein F | Apof | secreted | NM_001638 |
| apolipoprotein L | APOL1 | integral membrane protein | NM_001136540 |
| growth arrest-specific 1 | GAS1 | anchored to plasma membrane | NM_002048 |
| interferon, alpha 21 | IFNA21 | secreted | NM_002175 |
| interferon, alpha 2 | IFNA2 | secreted | NM_000605 |
| interferon, alpha 5 | IFNA5 | secreted | NM_002169 |
| interferon, alpha 8 | Ifna8 | secreted | NM_002187 |
| interleukin 12B (natural killer cell stimulatory factor 2, cytotoxic lymphocyte maturation factor 2, p40) | IL-12b | secreted | NM_002187 |
| interleukin 4 | IL4 | secreted | NM_000589 |
| interleukin 26 | IL26 | secreted | NM_018402 |
| interleukin 1, alpha | IL1 | Secreted | NM_000575 |
| interleukin 12 receptor, beta 1 | IL12RB1 | integral membrane protein | NM_005535 |
| interleukin 17A | IL-17A | secreted | NM_002190 |
| interleukin 17D | IL17D | secreted | NM_138284 |
| interleukin 17 receptor A | IL-17RA | integral membrane protein | NM_014339 |
| interleukin 18 binding protein | IL18BP | secreted | NM_001039659 |
| interleukin 1 family, member 9 | IL36G; IL1H1 | n/a | NM_019618 |
| interleukin 1 receptor, type II | IL1R2 | integral membrane protein | NM_004633 |
| interleukin 1 family, member 7 (zeta) | IL1RP1 | not listed | NM_014439 |
| interleukin 1 receptor-like 2 | IL1RL2; IL1R-rp2 | integral membrane protein | NM_003854 |
| interleukin 22 receptor, alpha 2 | IL22RA2; IL-22BP | secreted | NM_052962 |
| interleukin 22 receptor, alpha 1 | IL22RA1; IL22R | integral membrane protein | NM_021258 |
| interleukin 25 | IL25 | secreted | NM_022789 |
| Epstein-Barr virus induced 3 | EBI3; IL27B | | NM_005755 |
| interleukin 28A (interferon, lambda 2) | IL-28A | secreted | NM_172138 |
| interleukin 2 receptor, beta | IL2RB | integral membrane protein | NM_000878 |
| interleukin 3 receptor, alpha (low affinity) | IL3RY | integral membrane protein | NM_002183 |
| interleukin 7 | IL7 | secreted | NM_000880 |
| interleukin 6 (interferon, beta 2) | LOC541472 | secreted | NM_000600 |
| interleukin 19 | IL19; MDA1 | secreted | NM_013371 |
| interferon, gamma | IFNG; ifg | secreted | NM_000619 |
| renin | REN; HNFJ2 | secreted | NM_000537 |
| alpha-1-B glycoprotein | A1BG; gab | secreted | NM_130786 |
| complement factor H | CFH; AHUS1 | secreted | NM_000186 |
| cathepsin B | CTSB | secreted | NM_001908 |
| interleukin 10 | MGC126451 | secreted | NM_000572 |
| vascular endothelial growth factor A | MGC70609; VEGF | secreted | NM_003376 |

TABLE 6-continued

Genes of particular interest identified by molecular profiling of human lymphedema.

| Gene of Interest | Abbreviated Gene Name | Cellular location | Refseq No. |
|---|---|---|---|
| serpin peptidase inhibitor, clade E (nexin, plasminogen activator inhibitor type 1), member 1 | SERPINE1; PAI1 | platelet alpha granule lumen | NM_000602 |
| fms-related tyrosine kinase 4 | Pcl (AKA VEGFR3) | integral membrane protein | NM_182925 |
| peroxisome proliferator-activated receptor gamma | pparg1 | integral membrane protein | NM_005037 |
| hepatocyte growth factor (hepapoietin A; scatter factor) | HGF; SF | platelet alpha granule lumen | NM_000601 |
| inter-alpha (globulin) inhibitor H5-like | ITIH5L; UNQ6369 | secreted | NM_198510 |
| tumor necrosis factor (ligand) superfamily, member 15 | TNFSF15; TL1A | integral membrane protein | NM_001204344 |
| pregnancy specific beta-1-glycoprotein 9 | PSG9 | secreted | NM_002784 |
| pancreatic lipase-related protein 2 | pnliprp2 | secreted | NM_005396 |
| plasminogen | PLG; PLGL | secreted | NM_000301 |
| chorionic somatomammotropin hormone 1 (placental lactogen) | CSH; PL | secreted | NM_001317 |
| interleukin 17F | IL17F; ML1 | secreted | NM_052872 |
| thrombopoietin | TPO; MGDF | secreted | NM_000460 |
| interleukin 20 | IL-20; MGC96907 | secreted | NM_018724 |
| interferon, alpha 4 | IFNA4; MGC142200 | secreted | NM_021068 |

Example 3

Natural History of Lymphedema

Evaluation of the efficacy of molecular treatment strategies for lymphatic vascular insufficiency requires a suitable preclinical animal model. Ideally, the model should closely replicate the untreated human disease in its pathogenesis, biology, and natural history. Acute post-surgical lymphedema was experimentally created in the mouse tail and contrasted with the effects of exogenously administered human recombinant VEGF-C.

Quantitative assessment of immune traffic function was performed through sequential in vivo bioluminescent imaging. In untreated lymphedema, tail edema was sustained until day 21. Exogenous administration of human recombinant VEGF-C produced a significant decrease in volume. Untreated lymphedema in the mouse tail was characterized by the presence of dilated cutaneous lymphatics, marked acute inflammatory changes, and hypercellularity; VEGF-C produced a substantial reversion to the normal pattern, with notable regression in the size and number of cutaneous LYVE-1-positive lymphatic vessels. In vivo imaging confirmed the presence of an impairment of immune traffic in lymphedema that was ameliorated after VEGF-C administration.

Therapeutic lymphangiogenesis has been documented to be feasible and effective when exogenous recombinant human VEGF-C protein has been administered in experimentally-induced lymphedema in the rabbit ear (Szuba et al., 2002) and through adenoviral VEGF-C gene transfer to both the lymphedematous rabbit ear and mouse tail (Yoon et al., 2003). Molecular and cellular responses can readily be assessed in the mouse but the small size of the edematous tail poses difficulty for the measurement of dynamic changes in edema volume and in the functional assessment of lymphatic function. Thus, functional correlates of successful therapeutic lymphangiogenesis have not been adequately described, and the temporal aspects of lymphangiogenesis in this model remain poorly understood.

Nevertheless, the mouse model exhibits several features that make it conducive to further study of lymphatic impairment and the response to therapeutic intervention. The annulus of skin in the murine tail contains a well-defined hexagonally arrayed network of superficial lymphatics; when interrupted, marked edema of the tail develops. The natural history of the acquired edema in this model of lymphatic vascular insufficiency has not been completely characterized. Because the growth of new lymphatic vessels (lymphangiogenesis) in healthy animals is rapid, a definition of the time course of spontaneous lymphatic repair is necessary to be able to distinguish the impact of therapeutic lymphangiogenesis upon the rate or the completeness of endogenous repair responses. Accordingly, we have undertaken a study of the natural history of acquired lymphedema in the murine tail: serial assessment of tail volume was correlated with an in vivo assessment of the functional impairment in immune traffic and with post-mortem histological and histochemical attributes of the lymphedematous tissues. We contrasted the observations in untreated lymphedema with those obtained after exogenous therapeutic administration of human recombinant VEGF-C in the same model.

Methods

Creation of Experimental Lymphatic Vascular Insufficiency.

Post-surgical lymphedema was experimentally created in the tails of female hairless, immunocompetent SKH-1 mice (Charles River Laboratories, Boston Mass.) as described in example 1, above. Therapeutic VEGF-C lymphangiogenesis in experimental lymphedema. On post-surgical day 3, the treated animal subjects received parenteral recombinant human VEGF-C (R&D Systems Inc., Minneapolis, Minn.). Each animal received a single subcutaneous dose of 200 ng of the growth factor (2 mg/mL), equally divided between the proximal and distal wound edges. Untreated lymphedema subjects received subcutaneous saline analogously administered.

Tail Volume Quantitation.

Tail volume was serially quantitated in 19 mice divided into four treatment categories: normal, untreated lymphedema, VEGF-C-treated lymphedema, and surgical sham controls. For animals who had surgical intervention, this was defined to have occurred on day 0. All of the mice had quantitation of baseline tail volume; thereafter, volume was quantitated at defined time points: days 2, 4, 7, 9, 11, 14, 16, 18, 21, 23 28, 35, 42, 50, 57, 63, 65, 67 and 71. For each recording of tail volume, the mice were sedated with the medication regimen previously described. A single digital image of each tail was recorded with an OLYMPUS D520 Zoom digital camera at 1600×1200SHQ resolution. The camera was placed at a fixed distance (37 cm) from the tail with the optical axis perpendicular to the tail (angle 0°). Images were processed with Adobe Photoshop 7.0. The diameter of the tail was digitally, serially quantitated at distances of 8 mm beginning at the proximal end of the tail. Tail volume was derived from the measurements of tail volume using the truncated cone formula.

Histology.

For histological evaluation, 11 mice were sacrificed on Day 11 of observation. Immediately following sacrifice, 0.5 gm sections of the tail were harvested. Sections extended from a point 4 mm proximal to the surgical incision to 8 mm beyond it. The specimens were fixed overnight in 4% paraformaldehyde. After paraffin embedding, 5 µm sections were stained with hematoxylin and eosin (H&E, Richard-Allan Scientific). After deparaffinization in xylene, sections were rehydrated though a series of graded alcohol steps starting with 100% EtOH and ending in 50% EtOH. Slides remained in toluidine blue for 2 minutes and were then dehydrated through graded alcohol washes and covered with Cytoseal (Richard Allan Scientific).

LYVE-1 Immunohistochemical Staining.

5 µm-thick paraffin sections were prepared and stained for LYVE-1 as described in example 1, above.

Functional Imaging of Immune Traffic in the Lymphedema Model.

Experimental lymphedema was created surgically in the tails of 20 FVB/N female wild type mice (Jackson Laboratories, n=3), using the technique described above, and functionally compared with normal mice (n=8). The lymphedematous mice were treated with human recombinant VEGF-C or with saline, as described above, on post-surgical day 3. For in vivo bioluminescence imaging, spleens from transgenic luc+ heterozygous animals, expressing firefly luciferase under the control of a chicken beta-actin promoter, as previously described (Beilhack et al., 2005; Cao et al., 2004), were placed into single cell suspension. These single cell suspensions consisted of different hematopoietic lineages: ~40% were CD19+ B cells, ~20% CD4+ T cells, ~10-15% were CD8+ T cells, 3% NK1.1+ NK cells and the rest were GR.1+ granulocytes, Mac-1+ macrophages, CD11c+ dendritic cells and rarer cell populations. $4 \times 10^6$ splenocytes (>97% CD45+) in PBS were injected in a volume of 20 ml into the tail interstitium/emission]×100%. 1 cm caudal to the site of surgery, in lymphedema mice and normal controls, respectively. Normal mice were injected at the corresponding level of the tail. Injections were performed on post-surgical day 7. Thereafter, luc+ cells were imaged, in vivo on post-injection day 7 (corresponding to post-operative day 14). The mice were anesthetized by intraperitoneal co-injection of a mixture of ketamine (1 mg/mouse), xylazine (100 µg/mouse) in PBS and the substrate luciferin (150 mg/kg). Ten minutes thereafter, dorsal images were obtained with an IVIS100 CCD-imaging system. The efficiency of cellular lymphatic drainage was determined by direct imaging of light emission, with quantitation of the relative change in light emission from that measured at 20 hours after cell injection, as follows:

relative photon emission=[emission$_{day\ 7}$/emission$_{20\ hours}$]×100%.

Statistical Analysis.

Data analysis was performed with standard analysis of variance and paired t-test comparisons.

Results

Natural History of a Murine Model of Acute Experimental Lymphatic Vascular Insufficiency.

Figure 8:
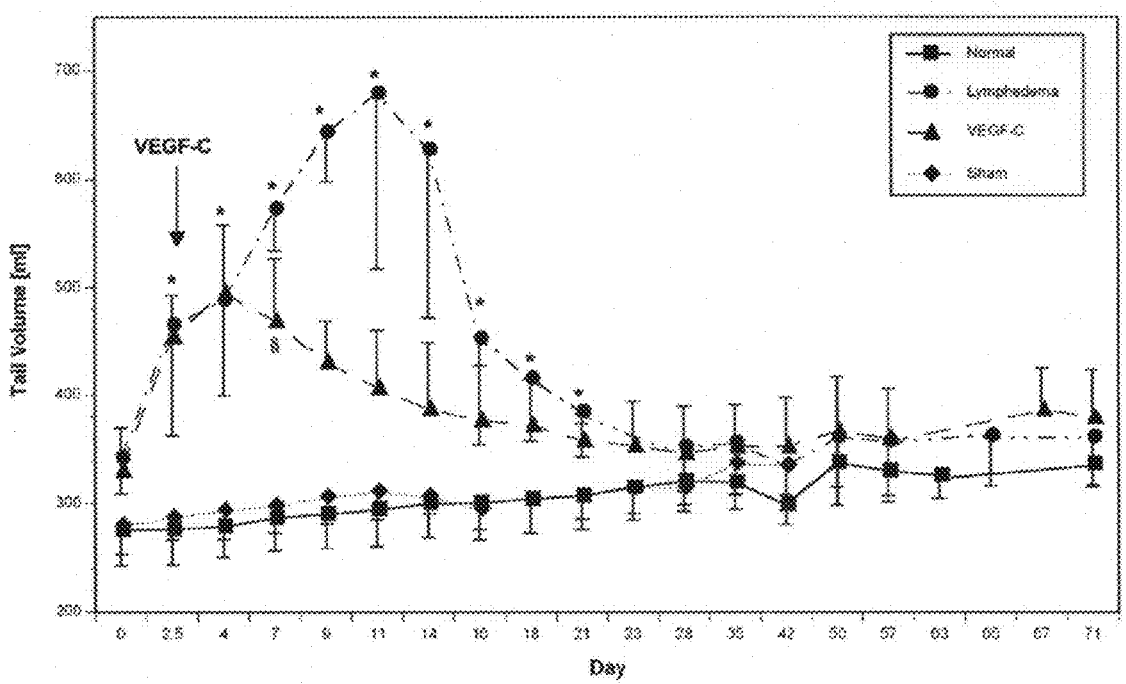
FIG. 8. Natural history of acute lymphatic vascular insufficiency. Tail volumes of lymphedematous and normal mice were statistically significant (*) by day 2 and achieved maximal significance on day 9 ($P<10^{-4}$). Surgical shams were indistinguishable from normals. After VEGF-C, volume reduction, compared with untreated lymphedema, was evident by day 7 (§).

Six (6) SKH-1 hairless mice were subjected to surgical lymphatic ablation, and 4 mice served as surgical sham controls. The responses of these mice were contrasted with 3 normal controls. Of note is the fact that cutaneous healing of the wound, both in the lymphedematous and surgical sham subjects, was complete by Day 14. The results of serial quantitation of tail volume are displayed graphically in FIG. 8.

In untreated lymphedema, tail volume increased incrementally over the first 10-12 days following surgical lymphatic ablation. Differences in the mean tail volumes of lymphedematous and normal mice attained statistical significance on day 2 (P<0.02); the increase in tail volume achieved its maximal significance on day 9 (P<$10^{-4}$) and was sustained as a statistically significant difference until day 21. In contrast, the mean tail volume of the surgical sham controls was indistinguishable from normals throughout the phase of observation.

The Effect of VEGF-C-Induced Lymphangiogenesis in Acute, Experimental Lymphedema.

An additional 6 SKH-1 mice with lymphedema received parenteral recombinant human VEGF-C by subcutaneous injection into the surgical wound on post-operative day 3. A diminution in the mean tail volume, when compared with untreated lymphedema, was evident by day 7 (4 days post-VEGF-C treatment, P=0.008). The difference between untreated and treated lymphedema was most significant by day 9 (P=0.0003) and persisted until at least day 14 (P=0.007).

Histological Responses to Lymphatic Vascular Interruption.

Figure 9:
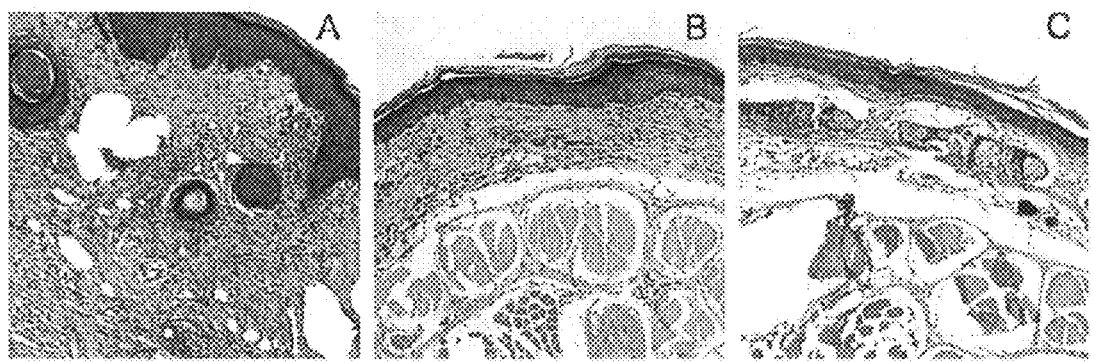
FIG. 9. Histology of experimental lymphedema (10×). (A) With untreated lymphedema, there acute inflammatory changes, marked hypercellularity, hyperkeratosis, spongiosis and edema of the epidermis. Numerous dilated skin lymphatics were seen. (B) After VEGF-C, there was substantial reversion to the normal pattern. (C) Normal tail sections were devoid of dilated lymphatics.

The tissue response to acute lymphatic disruption was assessed on day 11 in untreated lymphedema (n=4), VEGF-C treated lymphedema (n=3), and normals (n=4). Representative histological sections are displayed in FIG. 2. Tissue specimens derived from the lymphedematous tails were characterized by the presence of distinct acute inflammatory changes (FIG. 9A). Marked hypercellularity was noted, with an increased number of observed fibroblasts and histiocytes. A large infiltration of neutrophils is seen, with granulation tissue observed closer to the center of the section. Hyperkeratosis, spongiosis and edema of the epidermis was seen, with irregularity of the epidermal/dermal junction, elongation of the dermal papillae, and a two- to three-fold expansion of tissue between the bone and the epidermis. Numerous dilated lymphatics were seen in the dermis and subdermis. In contrast, normal tail sections were devoid of these dilated structures. The normal tissues were characterized by the presence of a thin dermis and epidermis, with a normal epidermal/dermal junction. The VEGF-C recipients (FIG. 9B) demonstrated a substantial reversion to the normal pattern (FIG. 9C), where the edema, hypercellularity, inflammatory changes, and microlymphatic dilation were absent.

LYVE-1 Immunohistochemical Staining.

Figure 10:
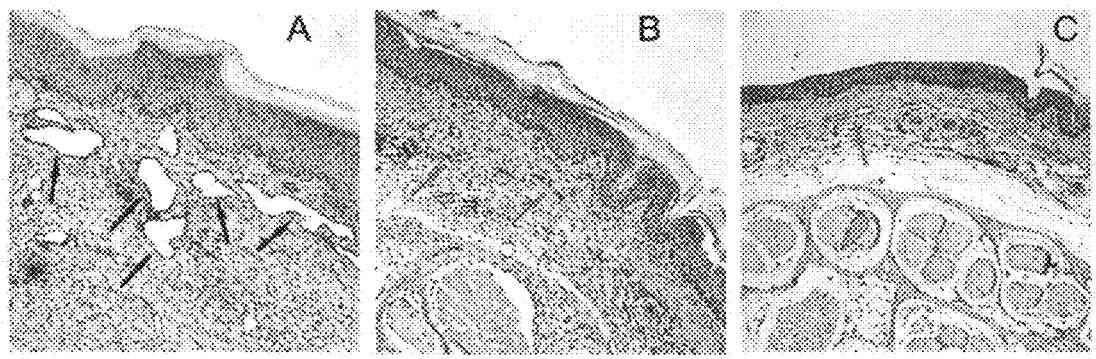
FIG. 10. LYVE-1 immunohistochemical staining (10×). (A) Acute lymphedema has numerous dilated LYVE-1-positive vascular structures (black arrows) in the dermis and subdermis. (B) After VEGF-C, there is reduction in the number and size of LYVE-1-positive vessels. (C). Lymphatics in normal skin. In normals and following VEGF-C, lymphatics are small and collapsed (red arrows).

The nature of the lymphatic vascular response distal to the anatomic surgical ablation was assessed with quantitative assessment of lymphatic vessel number and size by immunohistochemical staining for LYVE-1 (Banerji et al., 1999; Jackson, 2004). In comparison to normal sections, the lymphedematous tissue was characterized by the presence of numerous dilated LYVE-1-positive vascular structures in the dermis and subdermis (FIG. 10A). VEGF-C treatment yielded a reduction in the observed size and number of these skin lymphatics.

Mean lymphatic vessel number was determined by averaging the number of total lymphatic vessels in all of the fields of each slide at 10× magnification. The observer was blinded to the treatment status of the animal in each case. Lymphedema was characterized by an increase in LYVE-1-positive vessel number/field that was not observed in normals or after VEGF-C-treatment: lymphedema, 7.3±4.0 (P=0.02 compared to normal); VEGF-C, 1.3±0.9 (N.S.); and normal, 1.0±0.8.

Figure 11:
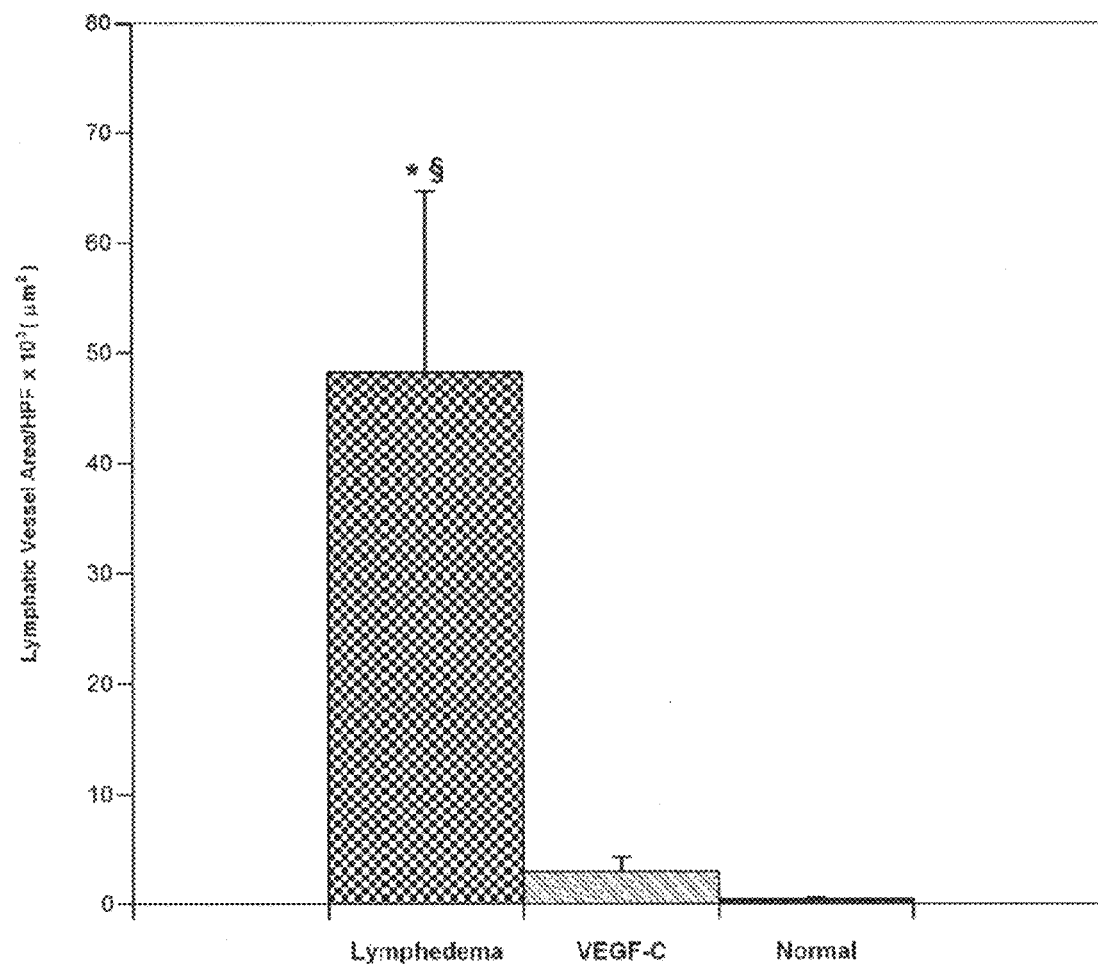
FIG. 11. Mean lymphatic vessel area. Lymphatic vessel area was quantitated according to the formula $\pi \cdot r_1 \cdot r_2$ (*$p=0.01$ when compared to normals; §=0.01 when compared to VEGF-C-treated lymphedema).

Lymphatic vessel area was quantitated according to the formula $\pi \cdot r_1 \cdot r_2$. As shown in FIG. 11, the average lymphatic area/field was 482,123±16,495 $\mu m^2$ in lymphedema (n=4) and 486±134 $\mu m^2$ in normals (n=4; P=0.01); in the VEGF=C treated lymphedema animals (n=3), there was a substantial reduction in the LYVE-1-positive vessel area (2992±1311 $\mu m^2$; P=0.01 compared with lymphedema and not significantly different than normals). Thus, in summary, acute experimental lymphedema was characterized in this model by an increase in vessel number but, even more notably, by an increase in lymphatic vascular cross-sectional area. Both vessel number and size returned substantially to normal following exogenous administration of recombinant VEGF-C.

Functional In Vivo Imaging of Immune Traffic.

The lymphatic vasculature participates in the immune response through the continuous transportation of white blood cells and antigen-presenting cells. In order to quantitatively assess a functional correlate of the observed edema volume and histological alterations in our model, we undertook functional in vivo imaging of changes in immune traffic in relationship to acute lymphedema and its response to VEGF-C.

Figure 12:
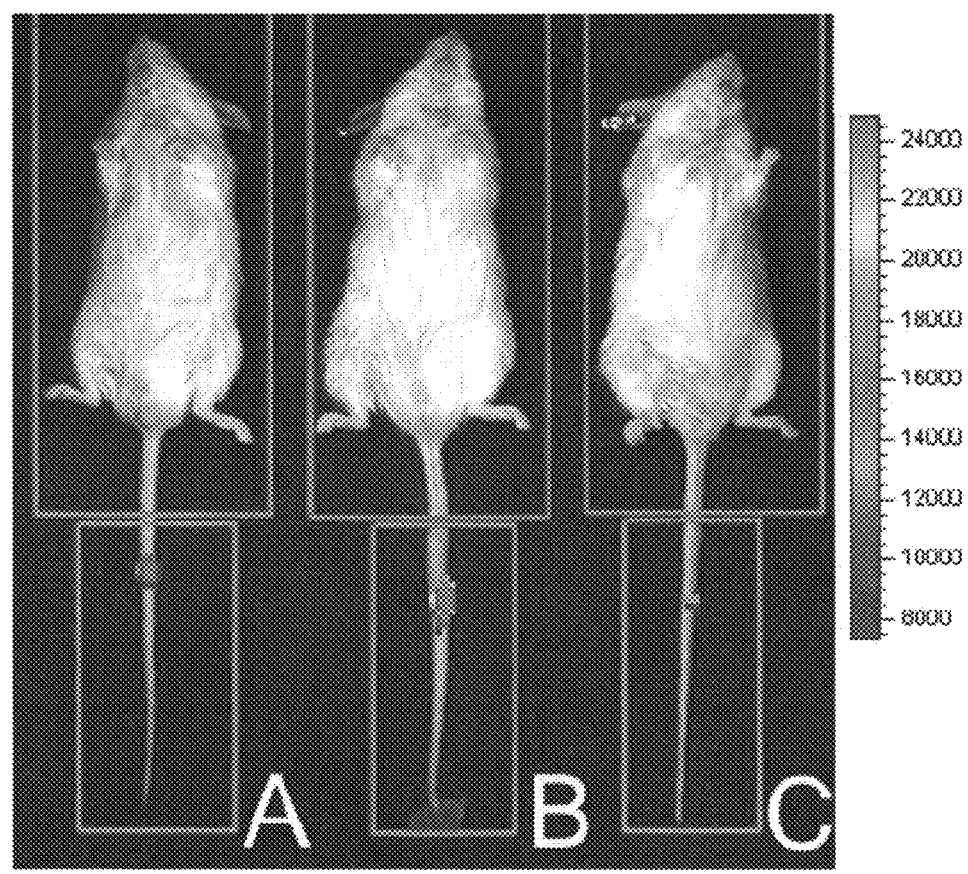
FIG. 12. Bioluminescence imaging of immune traffic in lymphedema. The figure depicts a series of in vivo imaging experiments for a representative set of lymphedema, VEGF-C recipient, and normal control mice. The scale of relative photon density is depicted to the right of the figure.

Bioluminescence imaging was performed on day 7 following the introduction of luciferase expressing (luc+) cells into the distal tail (corresponding to post-operative day 14). In general, when compared to normals, the clearance of bioluminescent immunocytes was delayed in lymphedema, but was ameliorated in the VEGF-C recipients. FIG. 12 depicts a series of imaging experiments for a representative set of lymphedema, VEGF-C recipient, and normal control mice.

The relative photon density, expressed as a % of the observed value 20 hours post-injection, was quantitavely assessed. Analysis of variance of the observed values in lymphedema (n=8), VEGF-C treatment (n=12) and normals (n=6) disclosed significant differences (P=0.008). The relative photon density, an expression of the retained splenocytes at the site of subcutaneous injection, was significantly greater in lymphedema (43±24%) than in normals (14±6%, P<0.01); VEGF-C recipients experienced a substantial decline in the measured relative photon density (24±9%, P=0.06 when compared to lymphedema).

Evaluation of the utility of therapeutic lymphangiogenesis, or any other molecular strategy for the alleviation of human lymphatic vascular insufficiency, will necessitate the ability to document and study the treatment response in a suitable preclinical animal model of lymphatic insufficiency. Ideally, the model should closely replicate the untreated human disease in its pathogenesis, biology, and natural history.

We have therefore undertaken a study of the short-term natural history of acquired, experimental lymphedema in the mouse tail. This straight-forward model possesses the desirable features of low cost, reproducibility, absence of disease latency, and negligible attrition from either morbidity or mortality. While this murine model exemplifies the well-recognized rodent capacity for spontaneous resolution of lymphatic vascular dysfunction, presumably through robust endogenous lymphangiogenic responses, it is nevertheless evident from this study that a suitable window exists in which the end-organ effects of lymphatic vascular insufficiency are present and readily quantifiable. We have demonstrated that in this model, for a period of 14-21 days following lymphatic ablation, there is a prompt, progressive, and ultimately, sustained edema response that is accompanied by a quantifiable impairment in regional immune traffic. Thus, the cardinal functional deficits of human lymphedema (impaired tissue fluid balance and immune function) are replicated in this model. Furthermore, the model is characterized histologically by the presence of profound architectural changes in the lymphedematous tissues, including remarkable hypercellularity, hyperkeratosis, spongiosis, and prominent inflammation. Qualitatively, these histological alterations strongly resemble those described in skin biopsy specimens of human acquired lymphedema.

In order to validate the utility of this model to evaluate the impact of molecular therapeutic interventions, we investigated the effects of exogenous administration of human recombinant VEGF-C protein. It is now well-established that VEGF-C participates in the lymphatic endothelial cell proliferation required for lymphangiogenesis, although additional factors are likely to be necessary for the successful induction of new vessel growth. Nevertheless, several investigators have described the capacity of VEGF-C augmentation to increase lymphatic vessel density and to reduce the edema volume of both primary and secondary forms of experimental lymphedema in animals. In the current investigation, we have demonstrated the ability of this lymphedema model to yield quantifiable, statistically significant reductions in edema volume that become evident within several days of growth factor administration and that create a sustained window in which to contrast the biology of the treated and untreated conditions. Changes in volume correlate with an amelioration of immune traffic that is observed through in vivo bioluminescent imaging.

Perhaps the most notable change that is detected after VEGF-C administration is the near-normalization of tissue architecture and resolution of the inflammatory responses that characterize the untreated disease response. In contrast to prior observations that emphasize a lymphangiogenic response characterized by an increase in lymphatic vessel density, our observations suggest that untreated, acute lymphedema is typified by a remarkable increase in cutaneous lymphatic vessel number and size that normalizes after the administration of VEGF-C. This observation bears further investigation, but the implication of this phenomenon, when interpreted in conjunction with the amelioration in the other functional attributes, is that growth factor-induced lymphangiogenesis leads to the creation of new channels for lymph egress that, in turn, alleviate the structural vascular consequences of distal lymph stagnation.

The model of the invention has utility. It is inexpensive, efficient, and reproducible. The current study confirms that it will allow the discrimination of even relatively subtle therapeutic responses. This model possesses all of the attributes necessary for a platform in which to rapidly screen therapeutic candidates. Furthermore, the rapidly established, profound histological and immunohistochemical changes permit focused study of the cellular and molecular responses of the vasculature and the tissues to acute lymphatic disruption. Further studies of this type provide an avenue to enhance our current limited comprehension of the vascular and tissue biology of lymphatic health and disease.

Example 4

Treatment of Lymphedema with Nonsteroidal Anti-Inflammatory Agent

As indicated by the above experimental data, interruption of inflammation may ameliorate the tissue response to lymphatic disruption. Studies were therefore performed to test the response to the administration of a systemic non-steroidal anti-inflammatory (ketoprofen) in the mouse model system. Ketoprofen was administered subcutaneously into the skin over the abdominal wall. Control animals received subcutaneous injections of vehicle only. The surgical lymphedema animals treated with ketoprofen had a significant reduction in the edematous response (P<0.02). As observed previously, the lymphedema H&E specimens showed dilated dermal lymphatic vessels, marked acute inflammatory changes, and an overall increase in cellularity. Surgical sham controls were indistinguishable from normals.

The ketoprofen-treated lymphedema specimens demonstrated substantial normalization from the untreated histology, with disappearance of dilated lymphatics and substantial reduction in the dermal thickening, hypercellularity, hyperkeratosis, and inflammatory substrate. Quantitative real-time reverse transcriptase-PCR (RT-PCR) for VEGF-C and -D revealed significant upregulation of the mRNA for both growth factors in the lymphedema subjects that received ketoprofen, compared to vehicle-treatment of lymphedema. The VEGF-C and -D signals in lymphedema/vehicle were indistinguishable statistically from both normals and surgical shams. Furthermore, VEGFR-3 expression was significantly upregulated by ketoprofen.

Methods

Creation of Experimental Lymphedema.

Tail lymphedema was induced in female hairless, immunocompetent SKH-1 mice (Charles River Laboratories, Boston, Mass.) as described [5]. The mice were anesthetized with a solution of ketamine, xylazine, and saline (0.07 ml i.p.). The skin of the tail was circumferentially incised 16 mm distal to its base. The major lymphatic trunks were identified by subcutaneous injection of methylene blue distal to the incision and ablated by limited cautery. The mice were carefully monitored for any visceral signs of distress. Sham surgery controls were treated identically, but without lymphatic cautery. Normal controls did not undergo any surgical manipulation. All mice were sacrificed in accordance with American Veterinary Medical Association guidelines for rodent euthanasia after day 11 days of observation. After sacrifice, 500 mg sections of the tail were harvested for paraffin embedding and RNA extraction. For all in vivo experiments, housing, husbandry and experimentation were in strict accordance with the Animal Welfare Act and the Guide for the Care and Use of Laboratory Animals.

Treatment Protocols.

Beginning on day 3 after the surgical manipulation, mice with lymphedema received subcutaneous injections of NSAID (ketoprofen, 5 mg/kg; Sigma, St. Louis, Mo.) (n=12), sTNF-R1 (pegsunercept, 3 mg/kg; Amgen, Thousand Oaks, Calif.) (n=17), or phosphate-buffered saline (PBS) (n=16) every other day until the day of sacrifice. Sham surgery and normal controls were treated identically with the NSAID (n=8 per group), sTNF-R1 (n=11 per group), or PBS (n=11 normal controls, n=8 sham surgery controls).

Tail Volume Quantitation.

Tail volume was measured serially in each mouse, using a digital photographic application of the truncated cone approximation [42] as described [43].

Histology.

Immediately after sacrifice, 0.5-g sections of tail were harvested for histological analysis and RNA extraction. Sections extended from a point 4 mm proximal to the surgical incision to 8 mm beyond it. The specimens were fixed overnight in 4% paraformaldehyde, embedded in paraffin, cut into 5-μm sections, stained with hematoxylin and eosin (Richard-Allan Scientific, Kalamazoo, Mich.), and examined by light microscopy.

Histomorphometric Quantitation.

Epidermal thickness was measured serially using digital images of histology slides stained with hematoxylin and eosin. Processing and analysis were performed using Adobe Photoshop CS4 and ImageJ (http://rsbweb.nih.gov/ij) as previously described with modifications (Sanders J E, et al. Comput Methods Programs Biomed. 1999; 59:167-180). Quantitative measurements were imported to Prism 5 software (GraphPad Software Inc., La Jolla, Calif.) for statistical analysis and graphing.

Quantitative Real-Time RT-PCR.

Quantitative real-time polymerase chain reaction (qRT-PCR) was performed as previously described (Chen M M, et al. Circulation. 2003; 108:1432-1439.). Primers and probes were from Assays-on-Demand (Applied Biosystems, Foster City, Calif.). cDNA was synthesized from 5 μg of total RNA with Taqman reverse-transcription reagents (Applied Biosystems) and amplified in triplicate at 50° C. for 2 minutes and 95° C. for 10 minutes, followed by 40 cycles of 95° C. for 15 seconds and 60° C. for 1 minute. Reactions without template and/or enzyme were used as negative controls. 18S ribosomal RNA served as an internal control. A standard curve derived from embryonic mouse RNA was plotted for each target gene by linear regression using SPSS software (v. 11.0, Applied Biosystems). RNA quantity was expressed relative to the corresponding 18S control. Fold differences were calculated by dividing the experimental results by the pooled normal results and were plotted on a log 10 scale.

Tissue Cytokine Assays.

Cytokine levels in tail skin were measured in normal controls and mice with untreated, NSAID-treated, and sTNF-R1-treated lymphedema (n=3 per group) sacrificed on postoperative day 7. The Luminex LabMap200 System was used to measure the levels of 42 cytokines from the supernatant of tissue homogenates. Multiplex cytokine kits were purchased from Panomics (Fremont, Calif.), and the assay was performed according to the manufacturer's recommendation with the following modifications: 25-50 μl of samples, standards, and controls were added in duplicate to 96-well filter plates pre-configured with a panel of anti-cytokine antibodies covalently linked to unique polystyrene beads. The plate was incubated overnight at 4° C. in the dark with shaking at 500 rpm, vacuum aspirated, and washed three times with 140 µl of wash buffer to remove unbound antigen. Biotinylated detection antibody solution (25 µl) was added to each well and incubated for 1 hour with shaking at 500 rpm at room temperature. The plate was incubated with 50 µl of streptavidin-phycoerythrin for 35 minutes and then with 120 µl of reading buffer for 3 minutes at room temperature with shaking. After laser excitation, digital images of the bead array were captured with a CCD camera and analyzed on a computer workstation with BeadView software.

Statistical analysis. Two-sample t tests (equal variance) and one-way ANOVA were used to analyze the significance of difference for the tail volume, gene expression, and cytokine assays. $P<0.05$ was considered statistically significant. Standard deviations were calculated for all data.

Results

Lymphedema is Reduced by NSAID and Exacerbated by sTNF-R1.

Figure 13:
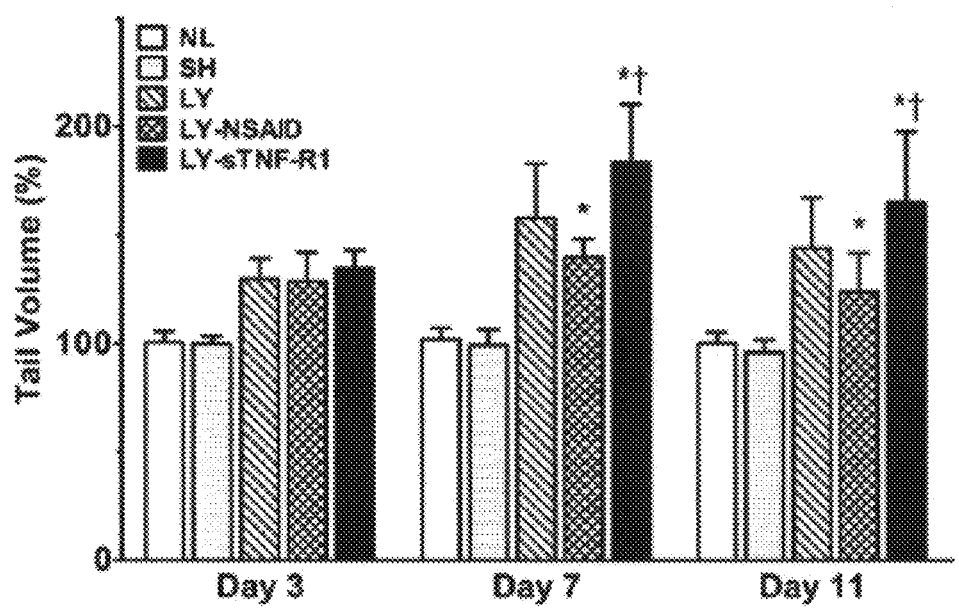
FIG. 13. Tail volume response to pharmacotherapy. Changes in tail volume are expressed as a percentage of the volume on day 0. By day 7, lymphedema (LY) mice demonstrate significant increase in tail volume. NSAID-treated lymphedema (LY-NSAID) mice were significantly less edematous than normal controls (NL) or sham surgery control (SH) mice. Conversely, sTNF-R1-treated lymphedema (LY-sTNF-R1) mice were significantly more edematous. *$P<0.05$ vs LY, †$P<0.05$ vs LY-NSAID.

Changes in tail volume are shown in FIG. 13. By day 3, tail volume had increased modestly in all three surgical cohorts. On day 7, however, tail volume was 158.0±25.0% of baseline in untreated mice with lymphedema ($P<5 \times 10^{-7}$ vs sham surgery controls), 139.8±8.5% in NSAID-treated mice ($P<0.05$ vs lymphedema), and 183.7±26.8% in sTNF-R1-treated mice ($P<0.005$ vs lymphedema). Tail volume changes persisted until sacrifice on day 11. sTNF-R1 had no discernable effect on tail volume in normal and sham surgery mice.

NSAID Therapy Normalizes Histological Changes in Mice with Lymphedema.

Figure 14:
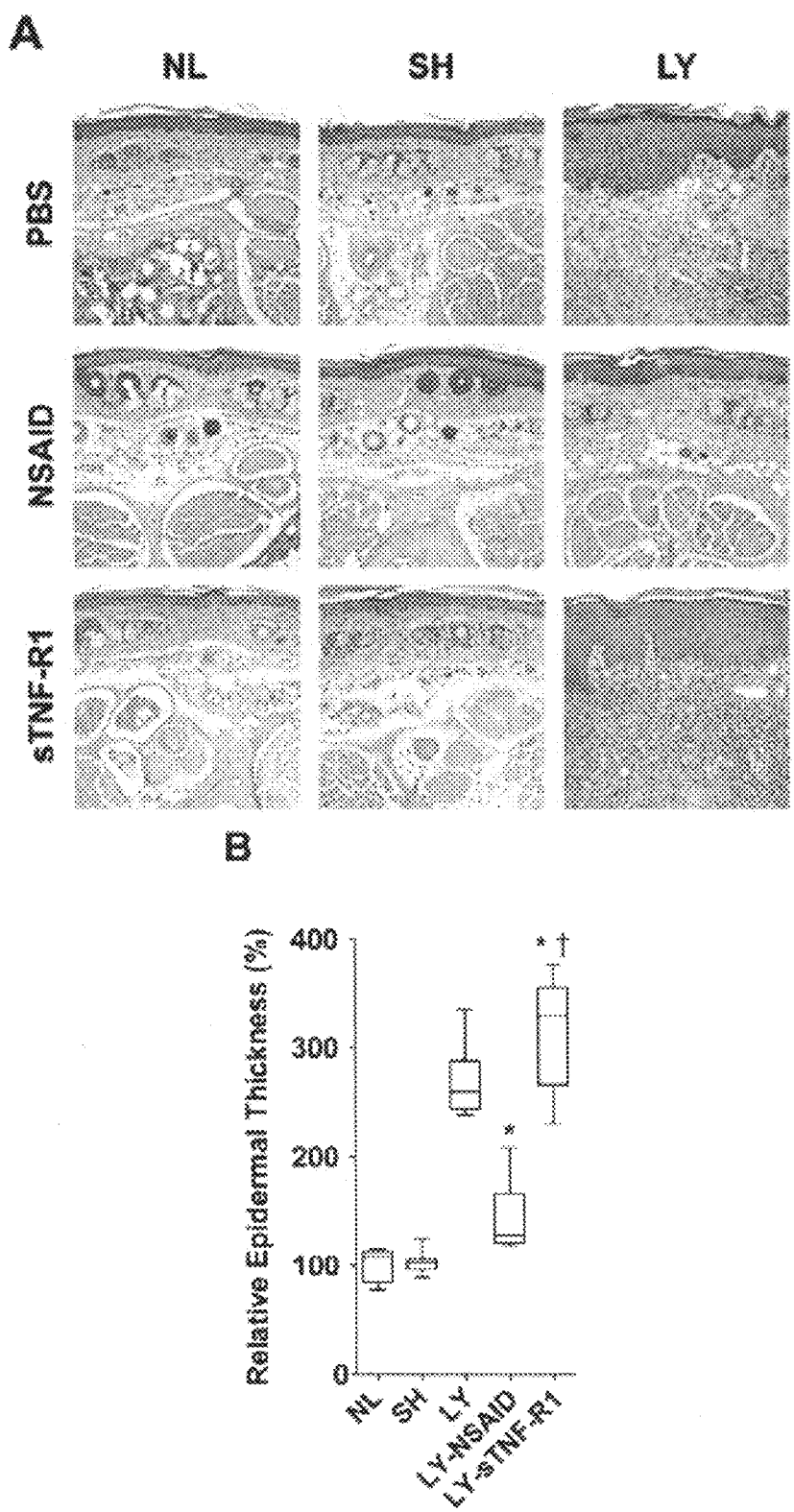
FIG. 14. Histological responses to pharmacotherapy. Tail sections were harvested 16 mm from the base of the tail, stained with hematoxylin/eosin, and examined by light microscopy. (A) Representative histology. Specimens from normal control (NL) mice, sham surgery control (SH) mice, and lymphedema (LY) mice treated with either PBS, ketoprofen (NSAID), or the TNF-α inhibitor sTNFR-1. Untreated LY show hyperkeratosis, epidermal spongiosis and edema, irregularity of the epidermal/dermal junction, elongation of the dermal papillae, and a 2- to 3-fold expansion of tissue between the bone and the epidermis. There are numerous dilated microlymphatics and increased cellularity, including a large infiltration of neutrophils. Treatment with NSAID normalizes these pathological findings whereas treatment with sTNFR-1 exacerbates the pathology. (B) Quantification of epidermal thickness (ET). Changes in ET are expressed as a percentage of the average ET of NL. ET of NSAID-treated lymphedema (LY-NSAID) mice was significantly reduced compared to untreated LY mice ($P<0.0005$) and were not significantly different than NL or SH control mice. ET of sTNF-R1 treated lymphedema (LY-sTNF-R1) mice was significantly increased compared to untreated LY mice (P<0.05). *P<0.05 vs LY, †P<0.0005 vs LY-NSAID.
Figure 15:
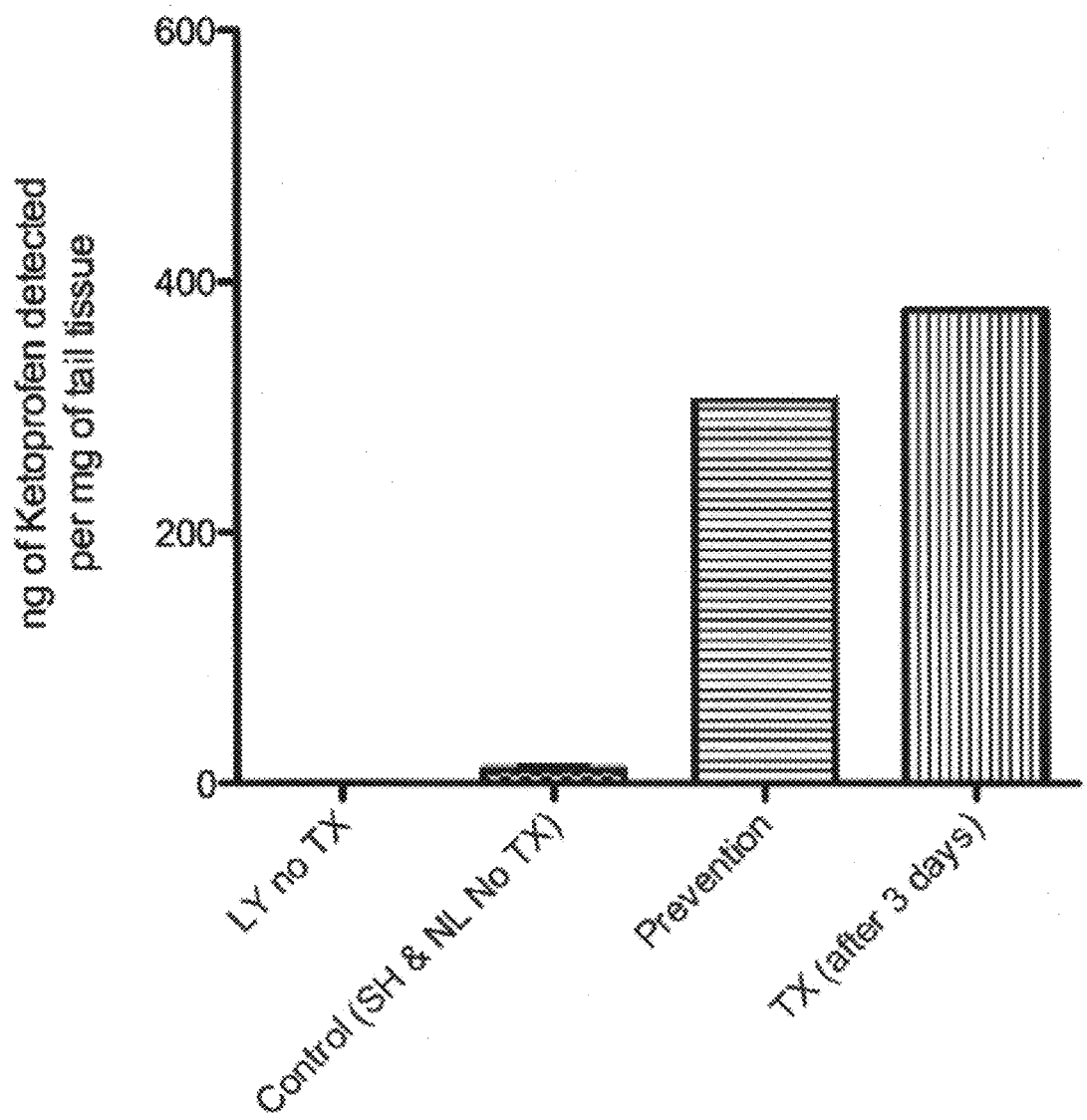
FIG. 15. Mass spectrometry of ketoprofen in tissue following topical administration demonstrates that topically administered ketoprofen permeates into the deepest layers of the skin. Ketoprofen was formulated as a topical preparation and delivered daily to mice. "LY no TX": biopsy from tissue surgically treated to induce lymphedema, no ketoprofen administered. "Control": biopsy from sham-treated and non-affected tissue, no ketoprofen administered. "Prevention": biopsy from tissue surgically treated to induce lymphedema, ketoprofen administered at the time of surgical treatment. "Tx (after 3 days)": biopsy from tissue surgically treated to induce lymphedema, ketoprofen administered regularly after surgical treatment.

Qualitative and histomorphometric analysis of paraffin-embedded, hematoxylin/eosin-stained skin sections obtained on day 11 revealed acute inflammatory changes in mice with untreated lymphedema (FIG. 14), as we have observed previously (Cheung L, et al. BioDrugs. 2006; 20:363-370; Tabibiazar R, et al. PLoS Med. 2006; 3:e254). Normal controls had a thin dermis and epidermis and a normal epidermal/dermal junction. In contrast, mice with untreated lymphedema had hyperkeratosis, epidermal spongiosis and edema, an irregular epidermal/dermal junction, elongated dermal papillae, and a 2- to 3-fold expansion of tissue between the bone and the epidermis. Epidermal thickness of lymphedema mice was 267.0±29.3% of normal control mice ($P<0.0005$). In addition, numerous dilated microlymphatics were evident in the dermis and subdermis, and there was a notable increase in the number of fibroblasts and histiocytes and a large infiltration of neutrophils. There were no histological differences between sham surgery and normal controls.

NSAID therapy resulted in normalization of histological changes, including restoration of normal dermal-epidermal architecture, disappearance of dilated microlymphatics, and marked resolution of inflammatory changes. Epidermal thickness was decreased 47.0±5.1% compared to untreated lymphedema mice ($P<0.0005$) and not significantly different than normal control mice. In contrast, sTNFR1 therapy produced no discernible amelioration; indeed, the epidermal thickness of sTNFR1-treated mice was significantly increased 16.0±2.5% compared to untreated mice with lymphedema ($P<0.05$). Neither therapy affected the histological appearance of post-mortem specimens from normal and sham surgery controls.

NSAID Therapy Prevents Lymphedema.

Figure 16:
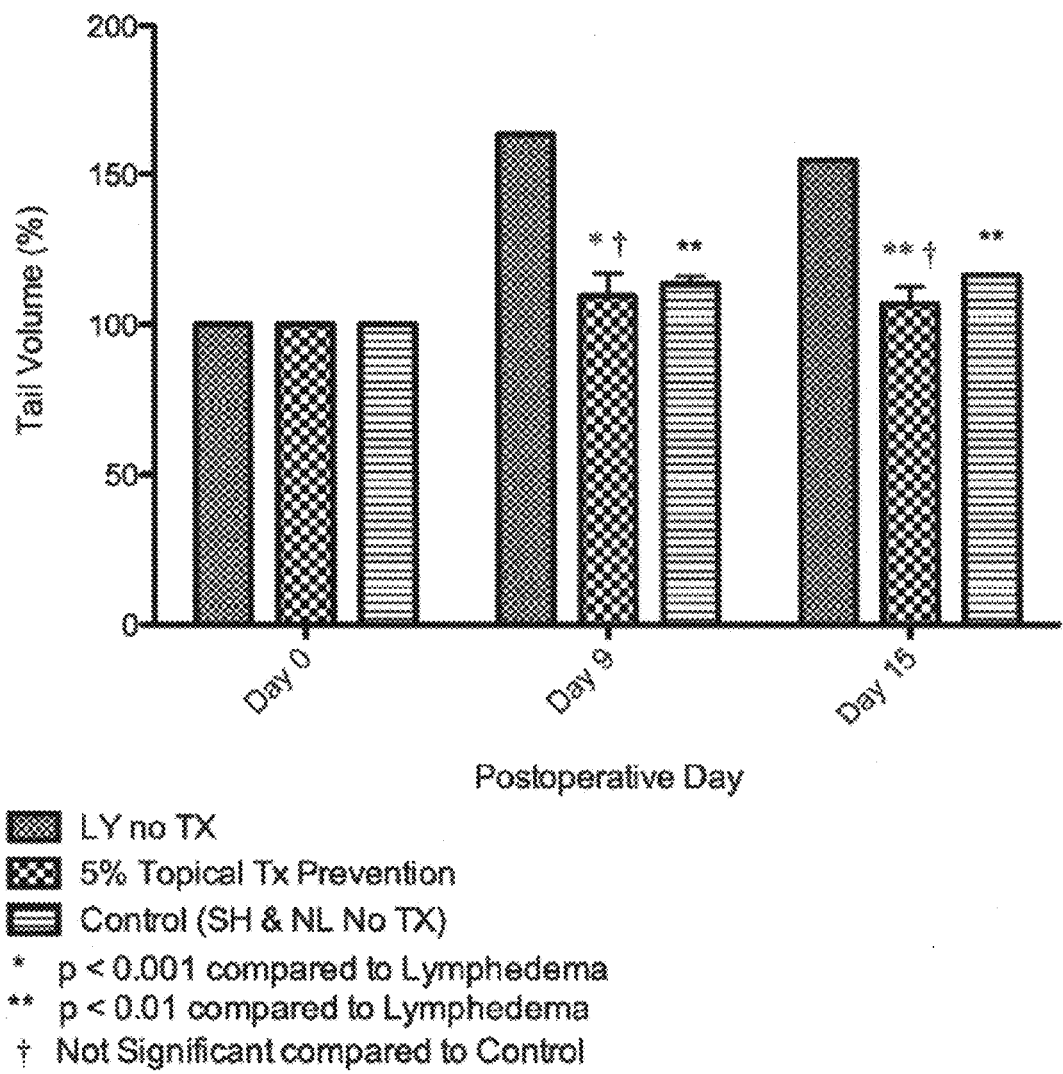
FIG. 16. Tail volume in mice treated prophylactically with ketoprofen prior to the induction of experimental lymphedema. In the absence of ketoprofen treatment, measurable lymphedema is observed by day 9 and day 15 following the surgical induction of lymphedema. In contrast, 5% topical pretreatment completely prevents lymphedema. "Ly no TX": volume of tissue surgically treated to induce lymphedema when no ketoprofen administered. "5% Topical TX prevention": volume of tissue in surgically treated animals pretreated with a 5% topical formulation of ketoprofen; "Control (SH &NL no Tx)": sham surgery control mice and normal mice, not treated with ketoprofen.
Figure 17:
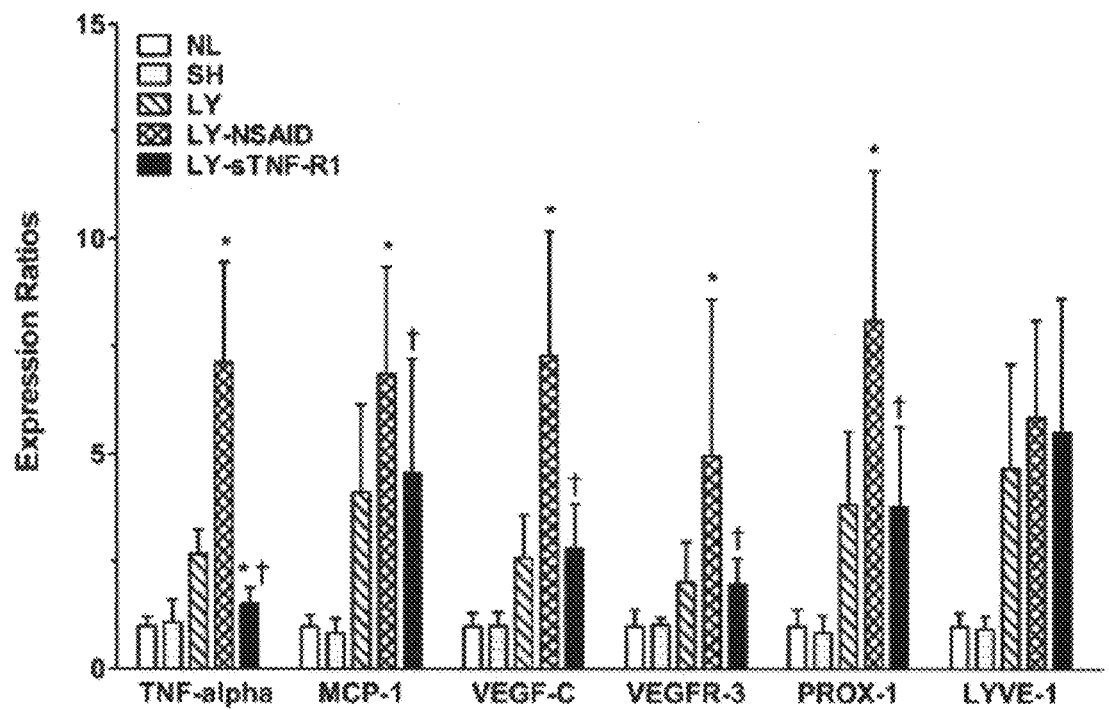
FIG. 17. Targeted gene expression analysis by quantitative real-time PCR. Fold-changes of gene expression are relative to normal (NL) controls on day 11. NSAID treatment significantly induced the expression of TNF-α, MCP-1, VEGF-C, VEGFR-3 and Prox1 in lymphedema (LY) mice. The TNF-α inhibitor sTNF-R1 downregulated TNF-α but did not affect other genes. *P<0.05 vs LY, †P<0.05 vs LY-NSAID.

In view of the growing evidence that lymphedema as an established disease involves inflammation, and that this inflammation can be pharmacology reverse, we hypothesized that inhibiting or abrogating the early inflammatory signals through pharmacological means might prevent the earliest expression of the disease. To test this hypothesis, we altered the traditional model of surgically induced lymphedema (which, untreated, produces lymphedema in 100% animal subjects), administering ketoprofen at the time that lymphedema was surgically induced rather than after ymphedema was established. As illustrated in FIG. 16, pretreatment and continued treatment with ketoprofen completely prevented the developments of lymphedema, which otherwise would have occurred. *Targeted Gene Expression Analysis by PCR*. Differential expression of six targeted, representative genes was quantitated by RT-PCR (FIG. 17). Skin was harvested for RNA extraction at the time of sacrifice, on day 11. TNF-α expression was up-regulated in untreated lymphedema. NSAID treatment further increased TNF-α expression ($P<0.5$), while treatment with sTNF-R1 reduced TNF-α expression to control levels ($P<0.05$ vs NSAID). A similar pattern of MCP-1 expression was observed. The NSAID-induced up-regulation of these pro-inflammatory cytokines was accompanied by significant, parallel up-regulation of VEGF-C, VEGFR-3, and Prox1 expression. Expression of LYVE-1 did not differ significantly among experimental cohorts.

Tissue Cytokine Analysis.

Figure 18:
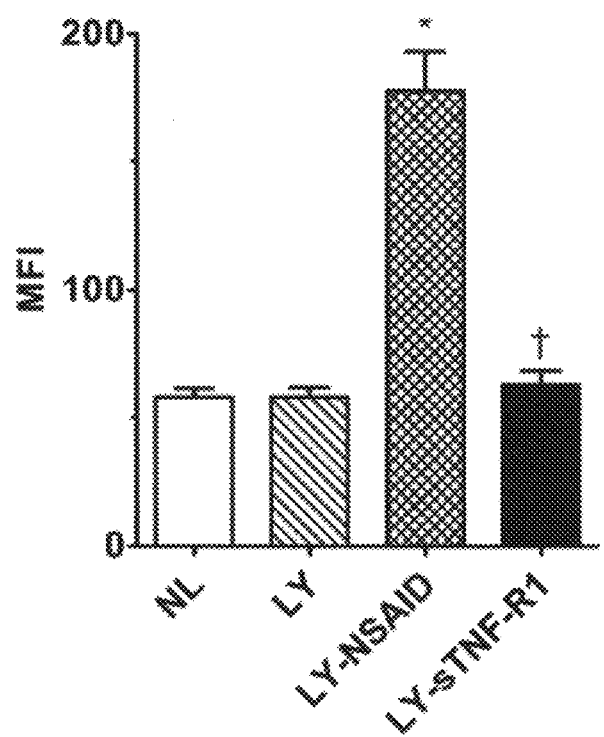
FIG. 18. TNF-α levels in tissue homogenates of tail skin. Median fluorescence intensity was used to assess the relative tissue concentrations of TNF-α. TNF-α levels were significantly higher in mice with NSAID-treated lymphedema (LY-NSAID) (P<0.005) than in normal controls or mice with untreated or sTNF-R1-treated lymphedema (LY-sTNF-R1). *P<0.005 vs untreated lymphedema, †P<0.005 vs LY-NSAID.
Figure 19:
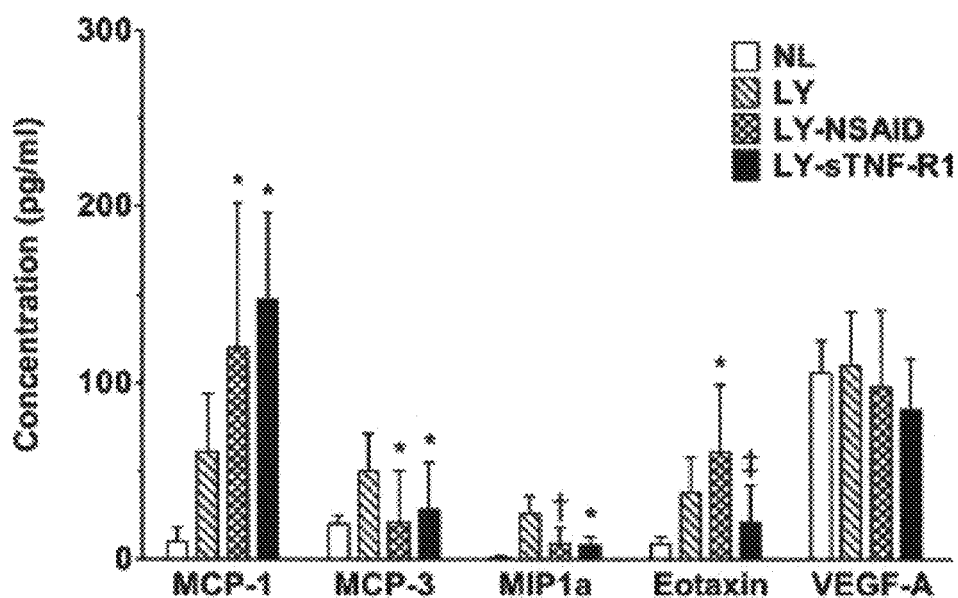
FIG. 19. Inflammatory cytokine levels in tissue homogenates of tail skin. Median fluorescence intensity was used to assess the relative tissue concentrations of MCP-1, MCP-3, MIP1a, Eotaxin, and VEGF-A. MCP-1 levels were elevated in mice with lymphedema (LY) and further increased by both ketoprofen and sTNF-R1 anti-inflammatory treatments. MCP-3 levels were also elevated in lymphedema but were significantly reduced by both treatments. A similar pattern was observed for macrophage inflammatory protein 1a (MIP1a). Like TNF-α, eotaxin levels were reduced by NSAID therapy and decreased by sTNF-R1. No effect on the blood vascular growth factor VEGF-A was observed. *P<0.04 vs to LY, †P=0.05 vs LY, ‡P<0.05 vs LY-NSAID.

In view of the disparate effects of the two systemic anti-inflammatory treatments on relative TNF-α gene expression, we quantitated tissue protein levels of this and other cytokines by direct assay of tail skin homogenates (FIGS. 17 & 18). TNF-α tissue levels were significantly higher in mice with NSAID-treated lymphedema ($P<0.005$) than in normal controls or mice with untreated or sTNF-R1-treated lymphedema. MCP-1 levels, too, were elevated in untreated mice with lymphedema and were further increased by NSAID and sTNF-R1 therapy ($P<0.04$). MCP-3 levels were also elevated in lymphedema, but were significantly reduced by both treatments ($P<0.04$). A similar pattern was observed for macrophage inflammatory protein 1a. Like TNF-α, eotaxin, a potent chemokine for neutrophils, was increased by NSAID therapy ($P<0.04$) and decreased by sTNF-R1 ($P<0.05$). The remaining cytokines assayed (TNF-β; RANTES; interleukins 1a and b, 2-7, 10, and 23; interleukin 12 p40 and p70; interferon-γ; granulocyte and granulocyte-macrophage colony-stimulating factors; IP10; and VEGF-A) showed no significant differences between treated and untreated lymphedema cohorts.

Discussion

Effective treatment of acquired lymphedema will likely require reversal of both lymphatic vascular insufficiency and inflammation. Our results indicate that systemic attenuation of inflammation and induction of pro-lymphangiogenic factors by the NSAID ketoprofen is an effective therapy for experimental surgically-induced lymphedema.

In the murine tail model, NSAID treatment lessens the profound cellular and molecular inflammatory response that has been described in clinical (Rockson S G. J Am Coll Cardiol. 2008; 52:799-806; Rockson S G. Am J Med. 2001; 110:288-295) and experimental lymphedema (Tabibiazar R, et al. PLoS Med. 2006; 3:e254; Olszewski W L, et al. Lymphology. 1990; 23:23-33). We have demonstrated that systemic anti-inflammatory therapy with ketoprofen can ameliorate lymphedema, but the impact upon tissue edema was marginal. Full resolution of the pathology and return to normal microvascular function appear to require more than generic anti-inflammatory intervention alone. Interestingly, the anti-inflammatory effects of ketoprofen were accompanied by robust transcriptional and translational up-regulation of TNF-α, consistent with in vitro and in vivo studies that demonstrate the direct induction of TNF-α by NSAIDs (Appleyard C B, et al. Am J Physiol. 1996; 270:G42-48.), including ketoprofen (Ghezzi P, et al. J Pharmacol Exp Ther. 1998; 287:969-974. Tsuboi I, et al. Cytokine. 1995; 7:372-379). This relationship is said to constitute a critical role in NSAID-related gastric intolerance (Santucci L, et al. Gut. 1994; 35:909-915) and is thought to be mediated by the inhibition of prostaglandin E2 (Jorres A, et al. Cytokine. 1997; 9:119-125; Kunkel S L, et al. Methods Achiev Exp Pathol. 1988; 13:240-259; Renz H, et al. J Immunol. 1988; 141:2388-2393; Sironi M, et al. Int J Immunopharmacol. 1992; 14:1045-1050; Tannenbaum C S, et al. J Immunol. 1989; 142:1274-1280), a feedback inhibitor of TNF-α expression. NSAID use is associated with relapse of inflammatory bowel disease (Meyer A M, et al. Dig Dis Sci. 2006; 51:168-172), further suggesting that up-regulation of TNF-α due to NSAID therapy is clinically relevant.

NSAID treatment significantly increased mRNA and protein levels of TNF-α while other inflammatory mediators such as MCP-3 and MIP1a were inhibited by NSAID treatment in lymphedema mice. This suggests that NSAID treatment specifically induces TNF-α while exerting otherwise anti-inflammatory effects. MCP-3 is a pro-inflammatory β-chemokine bound by β-Chemokine receptor D6 on a subset of lymphatics (Hub E, et al. Am J Pathol. 1998; 152:749-757). The pattern of D6 expression on lymphatics suggests that it may regulate chemokine-driven trafficking of leukocytes across lymphatics or during lymphangiogenesis (Scavelli C, et al. J Anat. 2004; 204:433-449.). Both NSAID and sTNFR-1 treatment inhibited MCP-3 protein levels, supporting their function as generally anti-inflammatory. The reduction of edema volume after NSAID treatment suggests that anti-inflammatory therapy may also facilitate the normalization of lymphatic vascular function. However, the functional status of the lymphatic vasculature in our model is not directly assessed. We have previous published that MRI can be used to assess the function of lymphatics (Pan D, et al. Lymphat Res Biol. 2006; 4:211-216.), but the modality remains costly and cumbersome. Functional assessment will be important to further elucidate the mechanism of our observations in future studies.

Across all study categories, the increases in TNF-α mRNA and protein levels correlated with increased expression of the pro-lymphangiogenic factor VEGF-C and its cognate receptor, VEGFR-3. Exogenous administration of VEGF-C lessens the severity and slows the progression of experimental lymphedema, including the murine tail model we used (Szuba A, et al. Faseb J. 2002; 16:1985-1987; Cheung L, et al. BioDrugs. 2006; 20:363-370; Jin da P, et al. Lymphat Res Biol. 2009; 7:47-57). TNF-α specifically induces VEGF-C (Ristimaki A, et al. J Biol Chem. 1998; 273:8413-8418; Cha H S, et al. J Rheumatol. 2007; 34:16-19; Paavonen K, et al. J Rheumatol. 2002; 29:39-45; Wauke K, et al. J Rheumatol. 2002; 29:34-38; Mouta C, et al. Lymphat Res Biol. 2003; 1:201-218) and Baluk et al. recently reported that TNF-α induces lymphangiogenesis in a murine model of airway inflammation (Baluk P, et al. J Clin Invest. 2009; 119:2954-2964). While the effects of TNF-α appear to directly affect the endothelium of the blood vasculature, effects on the lymphatic system may require the inflammatory mediators of recruited leukocytes. The role of the blood vasculature in our model has yet to be explored fully, but the blood vascular growth factor VEGF-A does not appear to be involved in our model. Our studies suggest that modulation of the complex interactions between the lymphatic and blood vasculatures and the inflammatory response during lymph stasis is a viable strategy that may yield clinically relevant therapies.

Figure 20:
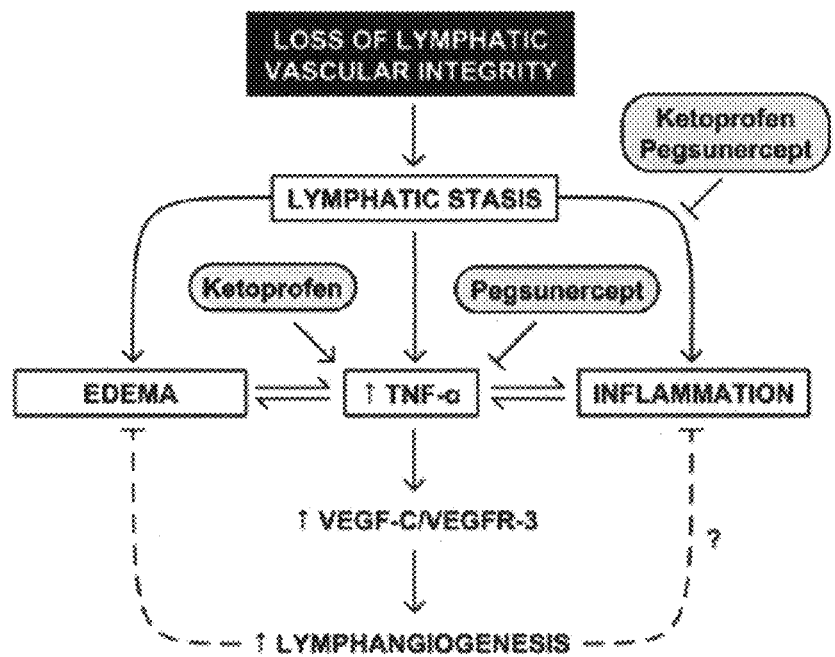
FIG. 20. Model of inflammation and lymphedema. Loss of lymphatic vascular integrity leads to diminished lymph transport, which promotes both edema and inflammation. TNF-α, a potent mediator of inflammation, is also a known inducer of the pro-lymphangiogenic factor, VEGF-C. Both ketoprofen and pegsunercept have general inhibitory effects on inflammation, ketoprofen promotes endogenous repair mechanisms mediated by VEGF-C and VEGFR-3 by simultaneous inducing TNF-α. In contrast, pegsunercept directly inhibits TNF-α and therefore exacerbates the disease state by disrupting pro-lymphangiogenic processes driven by VEGF-C and VEGFR-3.
Figure 21:
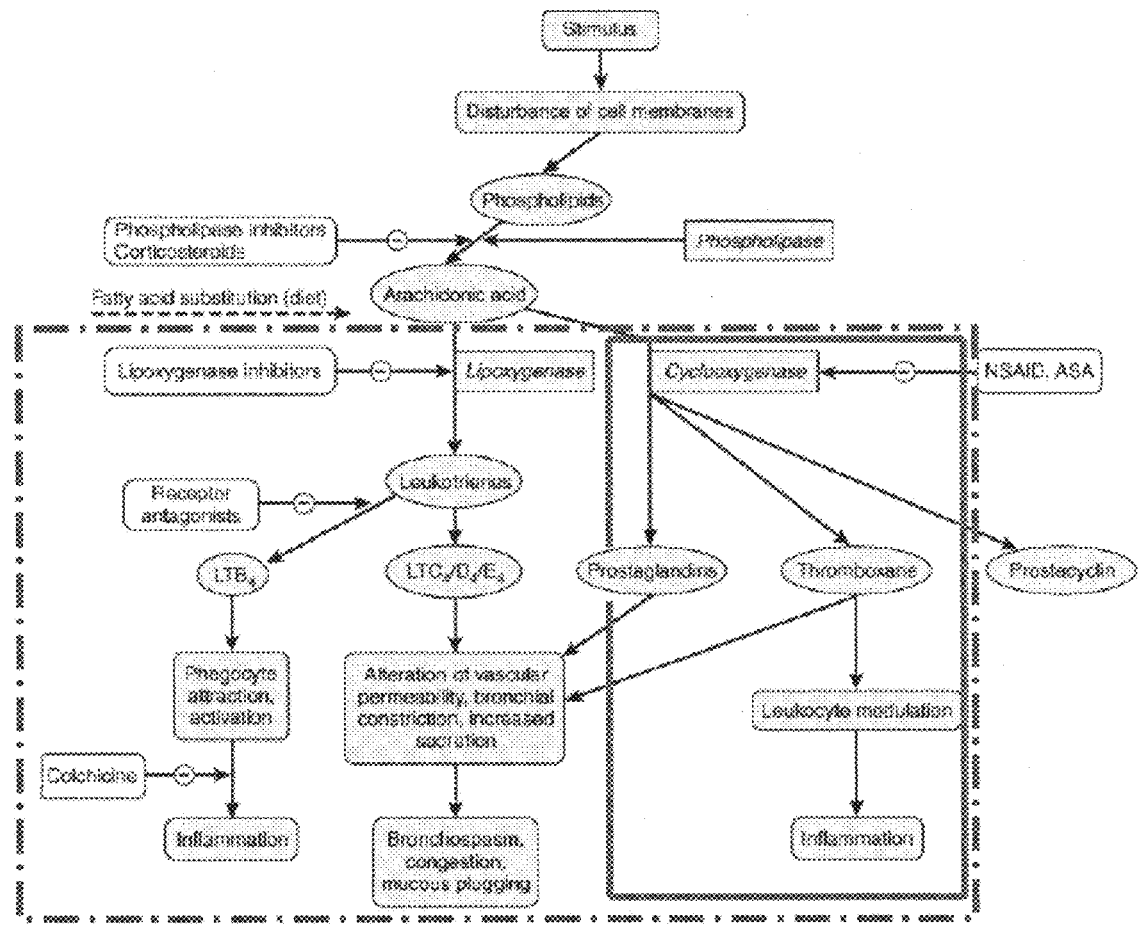
FIG. 21. Mechanism of action of propionic acid derivative NSAIDS. The dashed line represents biochemical pathways impacted by ketoprofen. The bold line represents biochemical pathways impacted by the remainder of the class.

We found that direct inhibition of TNF-α by sTNF-R1 decreased VEGF-C and VEGFR-3 transcription and expression and correlated with increased disease severity. Reciprocally, in addition to reducing inflammation and consequent tissue edema, ketoprofen may promote VEGF-C-mediated lymphangiogenesis through the induction of TNF-α (FIG. 20). These findings suggest that TNF-α-mediated up-regulation of VEGF-C expression may be a protective mechanism following lymphatic injury. TNF-α may be required for tissue repair as it appears to exert a permissive ameliorating effect in our model of acquired lymphedema. We tested this hypothesis by inhibiting TNF-α, which worsened the disease state. Although the mechanisms of VEGF-C-mediated therapy can be debated (Goldman J, et al. Circ Res. 2005; 96:1193-1199), the positive therapeutic response of augmented VEGF-C signaling can be plausibly linked, at least in part, to enhanced lymphatic repair and increased lymphatic function.

Lymphedema has the distinct morphological attributes of a cutaneous inflammatory disorder (Tabibiazar R, et al. PLoS Med. 2006; 3:e254). We demonstrated that systemic anti-inflammatory therapy with ketoprofen can ameliorate lymphedema, but the response on end-tissue edema was marginal. Full resolution of the pathology and return to normal microvascular function appear to require more than generic anti-inflammatory intervention alone. We propose that uncoupling the deleterious manifestations of inflammation from the desired pro-lymphangiogenic effects of endogenous repair mechanisms is a logical therapeutic strategy. The present study represents a novel and preliminary step toward the development of pharmacotherapeutics for the treatment of acquired lymphedema.

In summary, these data demonstrate the successful application of data obtained from the transcriptional profiling of experimental acquired lymphedema. Anti-inflammatory treatment reduced the edema response and substantially normalized the histopathological attributes of lymphedema. Furthermore, the administration of ketoprofen is associated with a clear cut upregulation of VEGF-C, VEGF-D and VEGFR-3 expression in the affected tissues, demonstrating a mechanistic benefit derived from enhanced lymphatic repair.

Example 5

Responsiveness of Lymphedema in Humans to Nonsteroidal Anti-Inflammatory Agent

Figure 22:
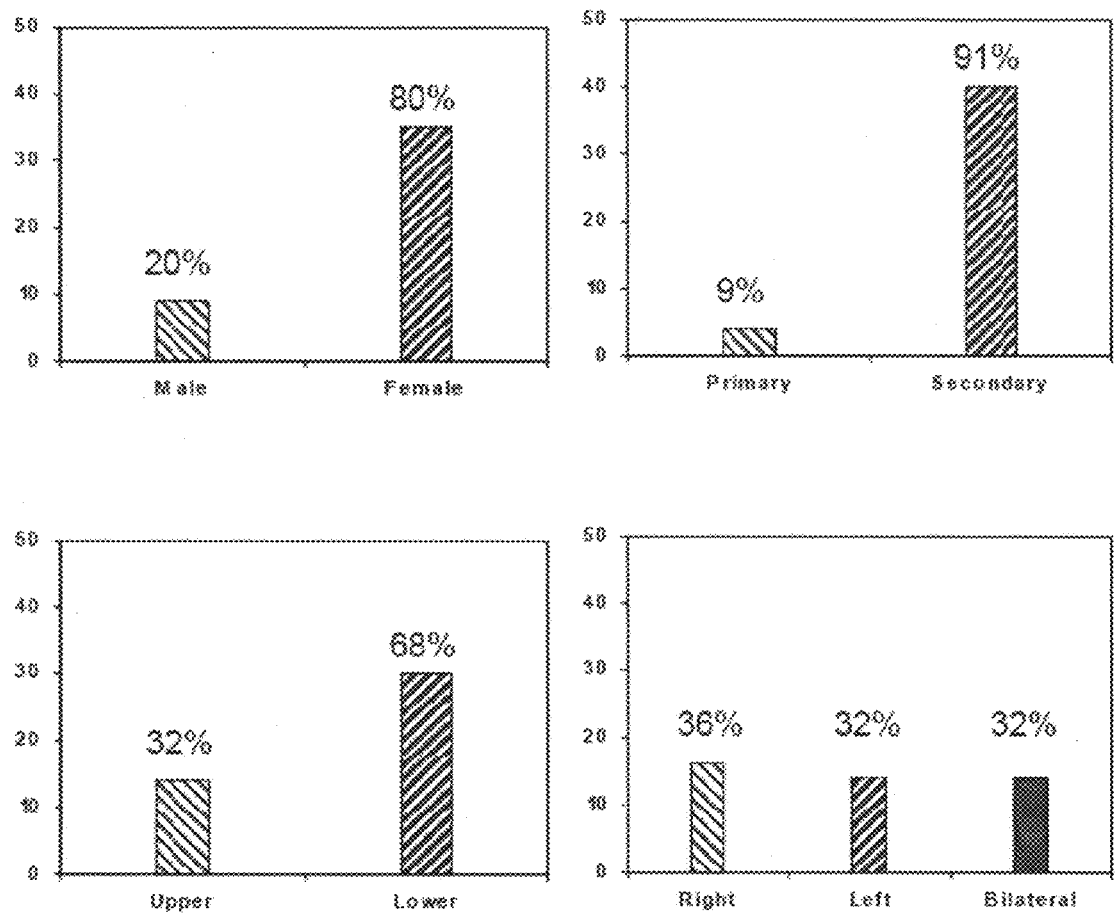
FIG. 22. Demographics of individuals enrolled in human study to assess responsiveness of lymphedema in humans to ketoprofen as of filing the present application. "Upper" and "Lower" refer to the location of the lymphedema in the patient, i.e. upper extremities or lower extremities. "Right", "Left" and "Bilateral" refer to the location of the lymphedema relative to the midline, i.e. on the right side of the patient, the left side of the patient, or both sides of the patient.

To determine the responsiveness of Lymphedema in humans to nonsteroidal anti-inflammatory agent, 75 mg ketoprofen was administered orally twice or three times per day for 90 days to patients with lymphedema. Biopsies were taken pre- and post-treatment, and clinical responses were reassessed monthly. 44 participants were enrolled (FIG. 22), 38 of which had completed the study at the time the data was collected. Average age of the patient was 57 years+/−14 years (24-85 years of age). The average length of time that the patient had had lymphedema was 10+/−10 years (0.5-40 years). Lymphedema was due to the following: breast cancer (12 patients (27.3%)); cervical cancer (6 patients (13.6%)); uterine cancer (2 patients (4.5%)); ovarian cancer (2 patients (4.5%)); penile cancer (1 patient (2.3%)); Hodgkin's lymphoma (2 patients (4.5%)); trauma (5 patients (11.4%)); infection (3 patients (6.8%)); venous insufficiency (3 patients (6.8%)); May-Thurner syndrome (2 patients (4.5%)); primary lymphedema (3 patients (4.5%)); other (2 patients (4.5%)).

Figure 23:
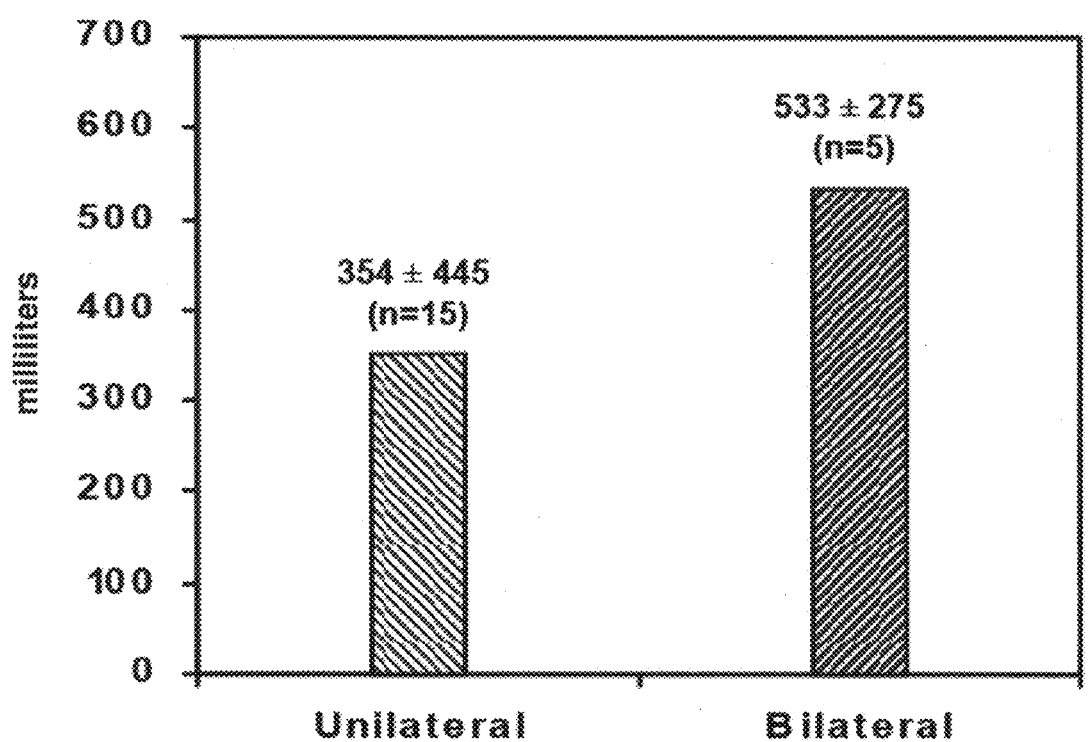
FIG. 23. Volume of fluid lost from tissue 90 days after the start of ketoprofen treatment. For the purposes of comparing bilateral results to unilateral results, volume lost in bilateral lymphedema was calculated by determining the total volume lost and dividing by 2.
Figure 24:
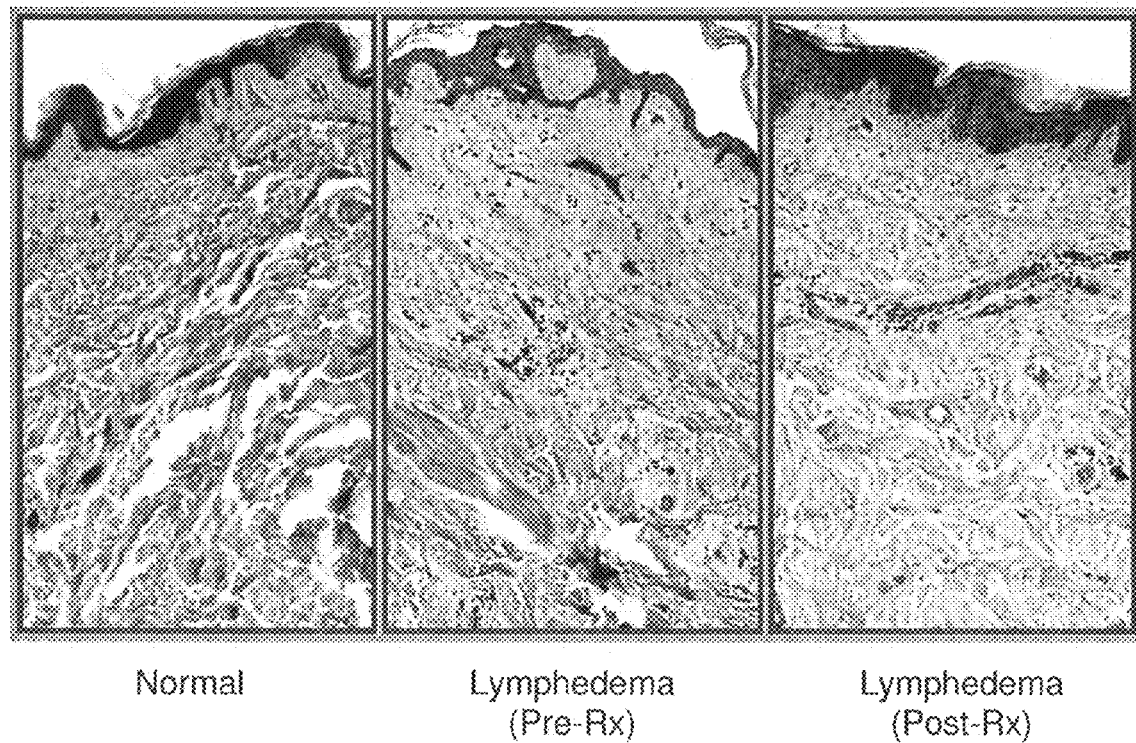
FIG. 24. Tissue architecture before and after ketoprofen treatment. (A) Cutaneous biopsies stained with Hematoxylin and Eosin. (B) Cutaneous biopsies stained with Hoechst. "Normal": unaffected contralateral limb. "Lymphedema, Pre-Rx": affected tissue at the start of treatment. "Lymphedema post-Rx": affected tissue 90 days following treatment.
Figure 24:
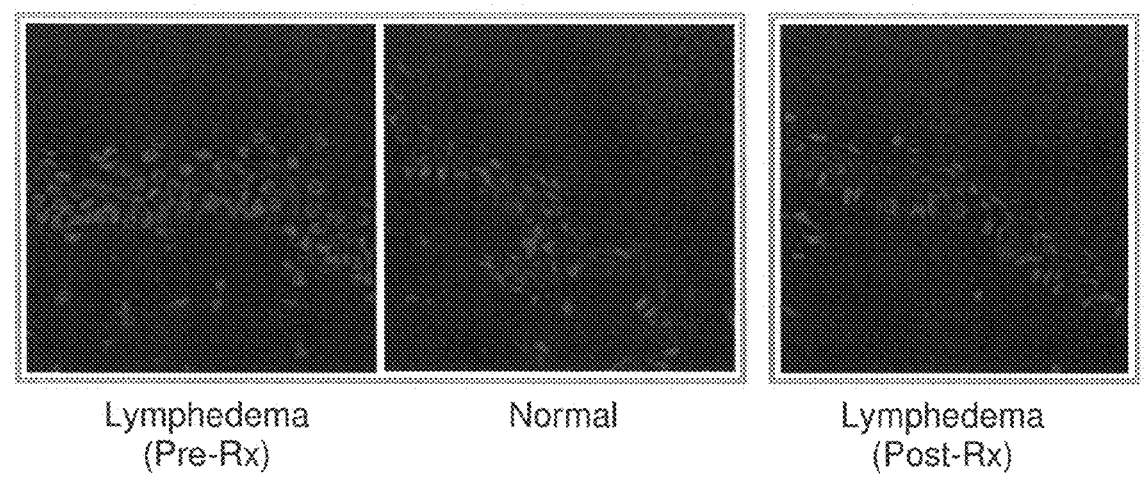
Figure 25:
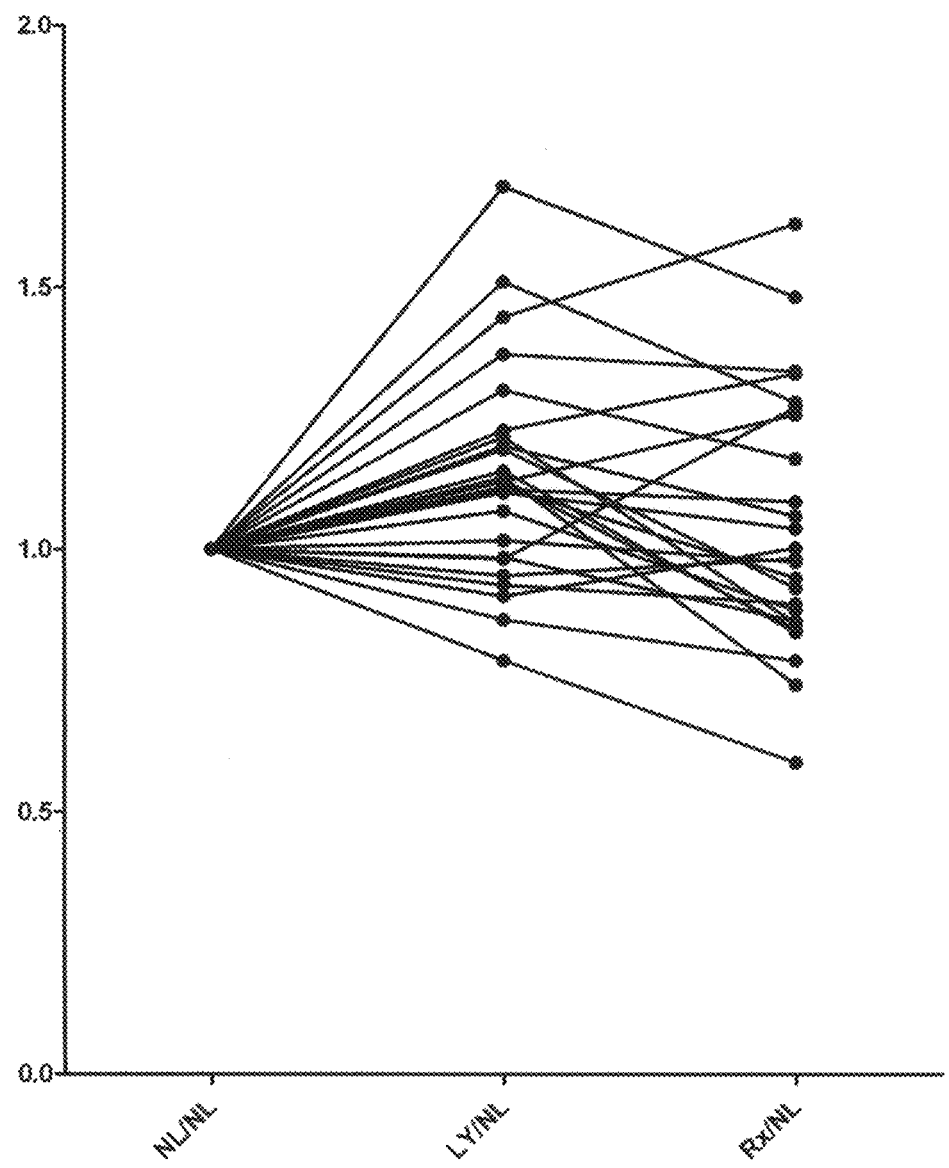
FIG. 25. Analysis of skin fibrosis by staining with Sirius Red demonstrates that ketoprofen treatment abrogates the inflammation that leads to a fibrotic response in the skin. Fibrotic response (thickening tissue, collagen deposition in dermis and subdermis) is quantified by measuring the mean pixel intensity of Sirius Red uptake. 3 cutaneous samples were taken from each patient: NL (unaffected tissue), LY (affected tissue at the start of treatment), and Rx (affected tissue 3 months after treatment with ketoprofen). In lymphedemous tissue (LY), an increase in fibrotic tissue is observed. Three months after the start of treatment (Rx/NL), the tissue has returned to a healthy state. Y axis is the ratio of paired samples. "NL/NL": fibrosis in unaffected tissue, normalized to the pixel intensity of Sirius Red uptake in the unaffected tissue. "LY/NL": fibrosis at the start of treatment, normalized to the pixel intensity of Sirius Red uptake in the unaffected tissue. "Rx/NL": fibrosis after 3 months treatment, normalized to the pixel intensity of Sirius Red uptake in the unaffected tissue.

On average, 354 milliliters of fluid was lost from the affected limb in patients with unilateral lymphedema that were treated with ketoprofen, and 533 milliliters of fluid was lost from one affected limb in patients with bilateral lymphedema (FIG. 23). Histological analysis of cutaneous biopsies by Hematoxylin and Eosin (FIG. 24) and by Sirius Red (FIG. 25) revealed a reversal of disease-associated protein deposition and fibrosis.

Figure 26:
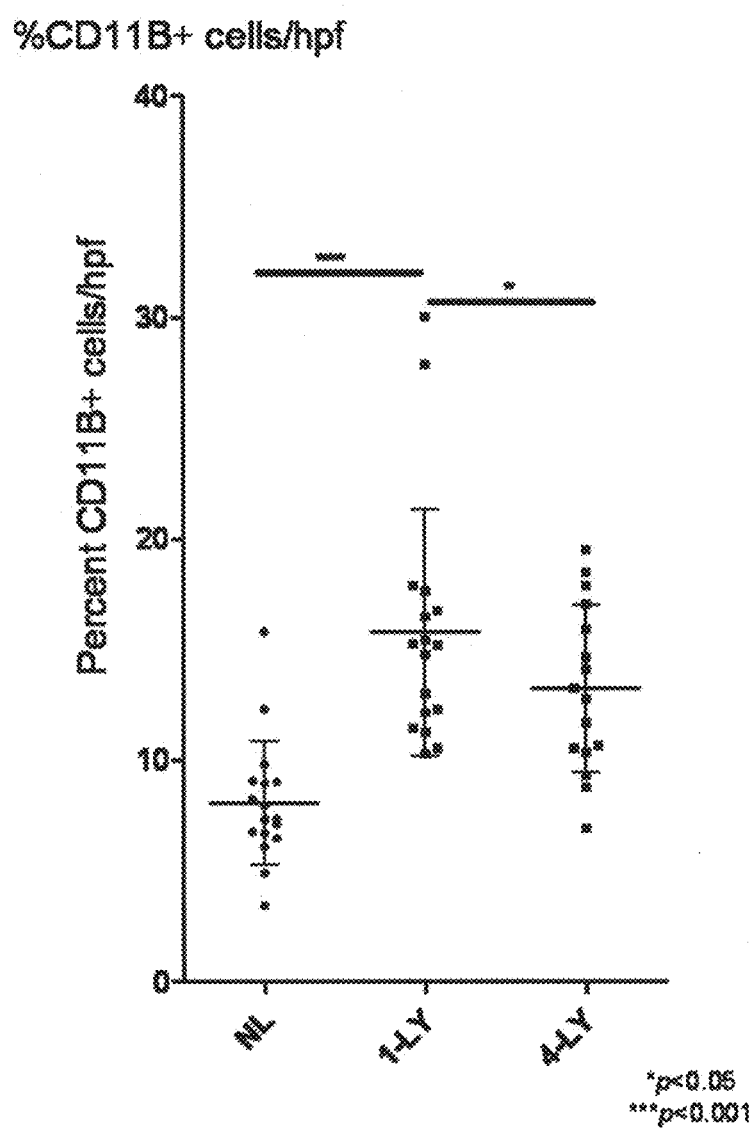
FIG. 26. Quantification of immunohistochemical analysis of CD11b+ leukocyte, monocyte, macrophage, and NK cell cell-infiltrates in lymphedemous tissue of patients treated with ketoprofen. 3 samples from each patient were analyzed by paired analysis: NL (biopsy from an unaffected limb), 1-LY (biopsy from affected limb), and 4-LY (4$^{th}$ clinical follow up visit). Lymphedema was specifically associated with an increase in cutaneous CD11B+ cells, indicative of inflammatory response. Treatment with ketoprofen statistically consistently returns CD11b counts to normal.
Figure 27:
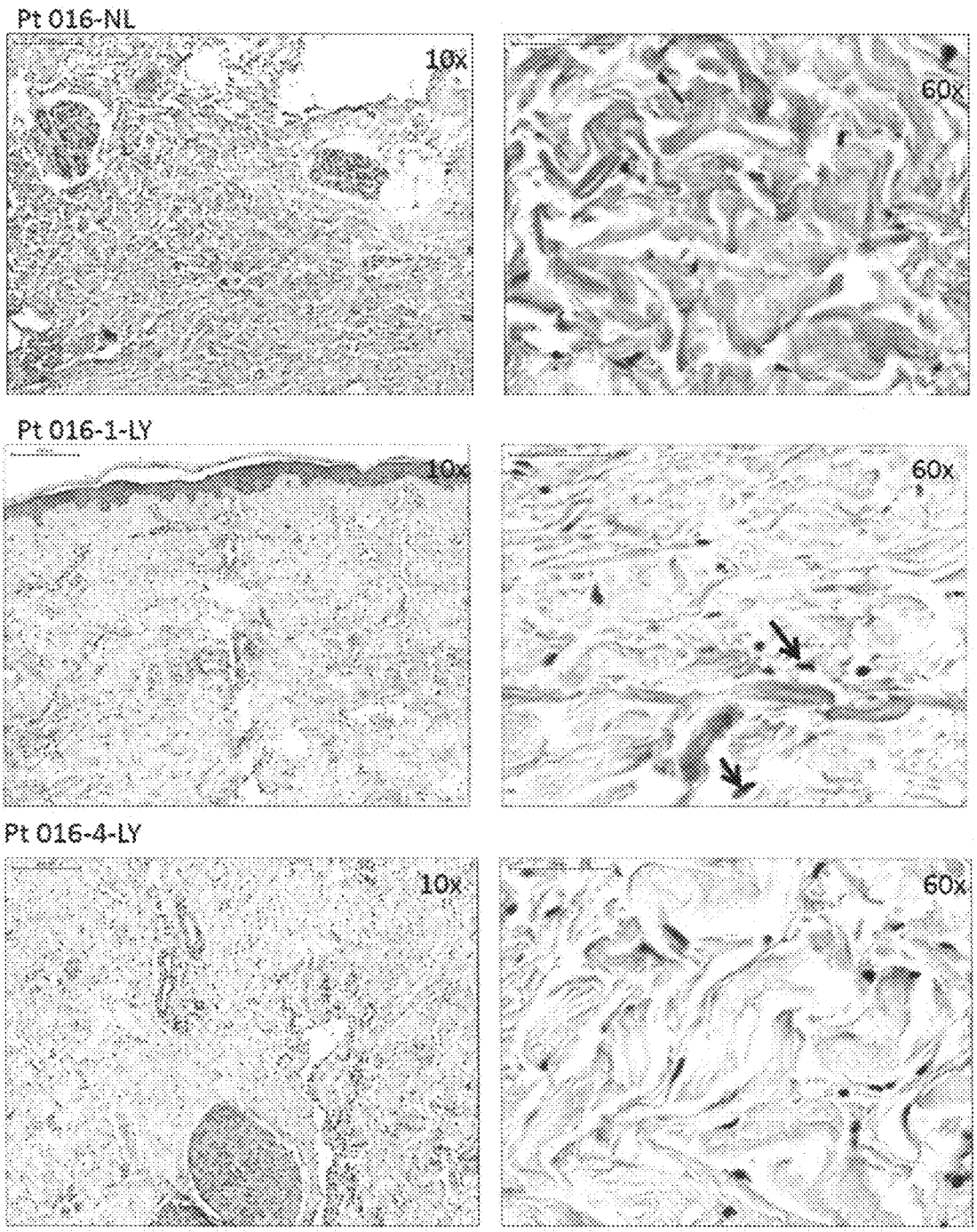
FIG. 27. Immunohistochemistry of CD11b+ cells in a representative patient (Patient 016). Arrows and brown staining indicate the presence of CD11b+ cells at the start of treatment with ketoprofen ("1-LY"). CD11b+ cells are absent by the 4$^{th}$ clinical follow up visit ("4-LY").
Figure 28:
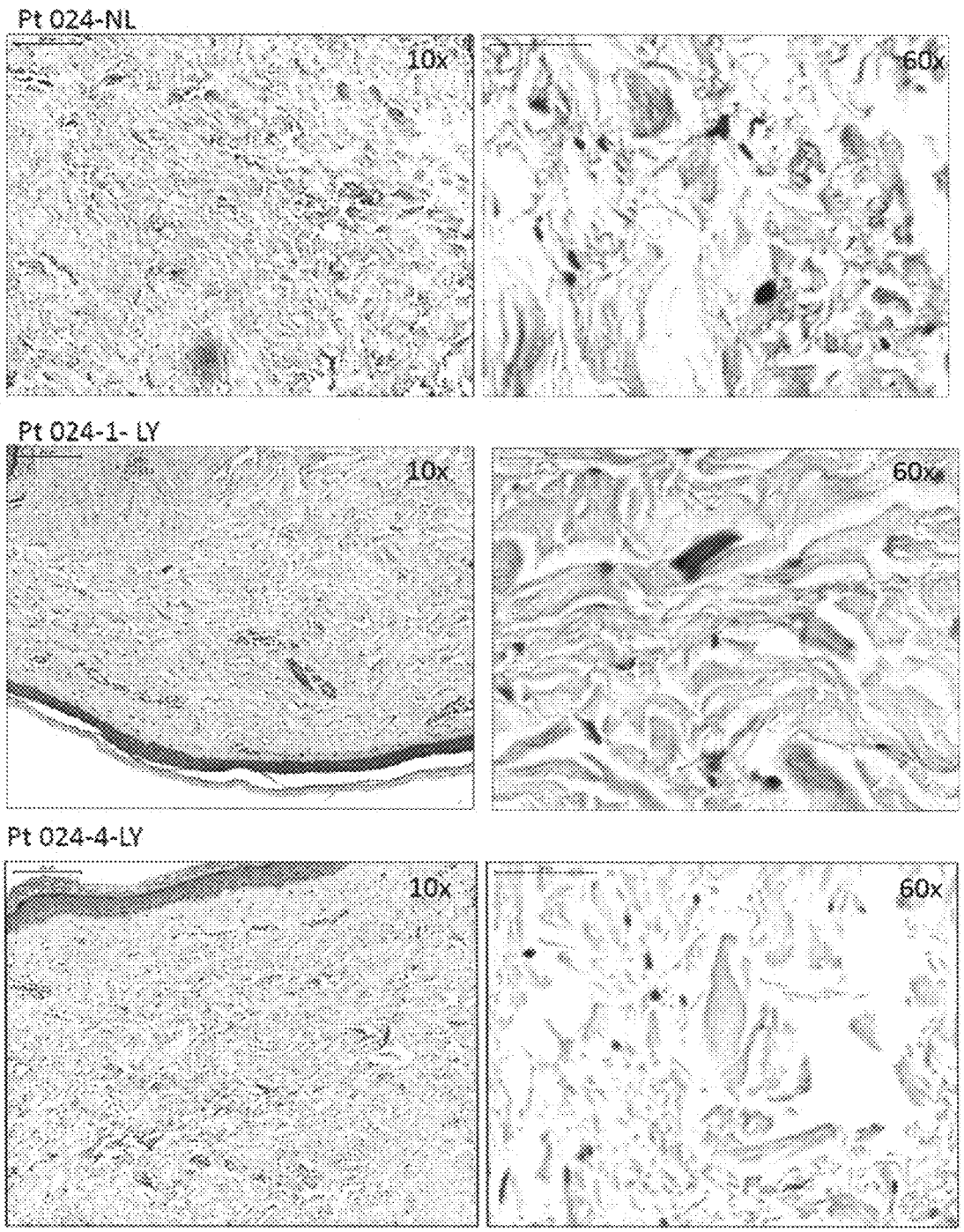
FIG. 28. Immunohistochemistry of CD11b+ cells in a representative patient (Patient 024). See FIG. 27 for details.
Figure 29:
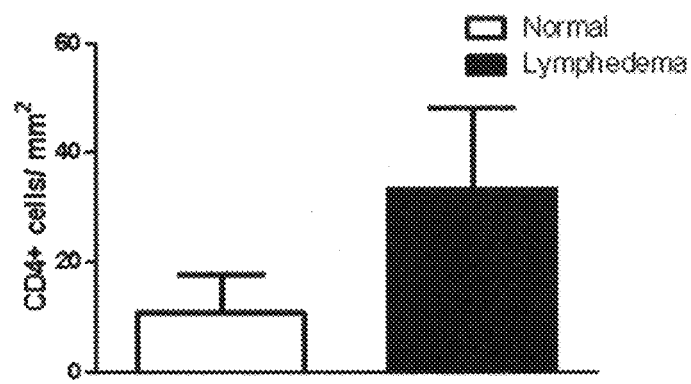
FIG. 29. Quantification of CD4+ helper T cell involvement in lymphedema pathology. 3 samples from each patient were analyzed by paired analysis: NL (biopsy from an unaffected limb), 1-LY (biopsy from affected limb), and 4-LY (4$^{th}$ clinical follow up visit). Lymphedema was specifically associated with an increase in cutaneous CD4+ T cells, indicative of inflammatory response. Treatment with ketoprofen statistically consistently returns CD11b counts to normal, indicating that anti-inflammatory therapy is normalizing the leukocyte population.
Figure 29:
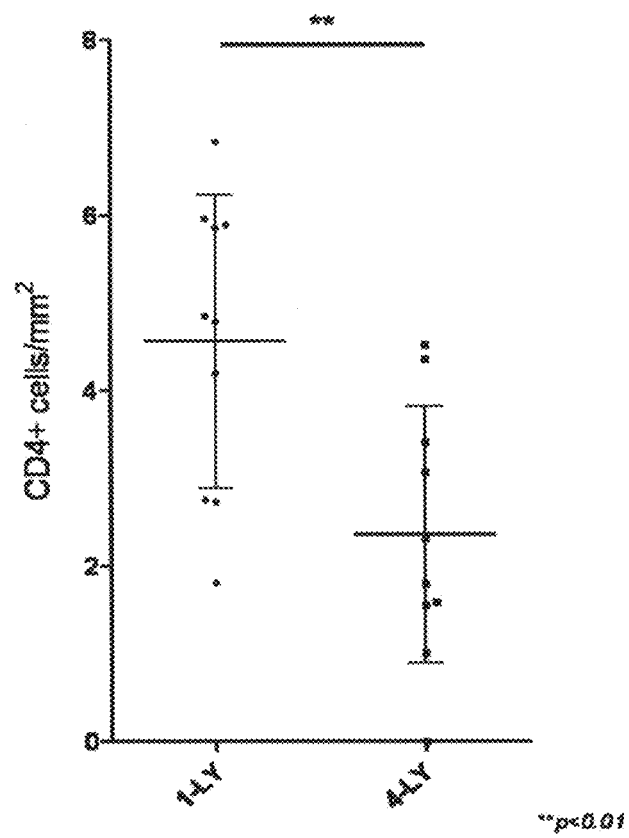
Figure 30:
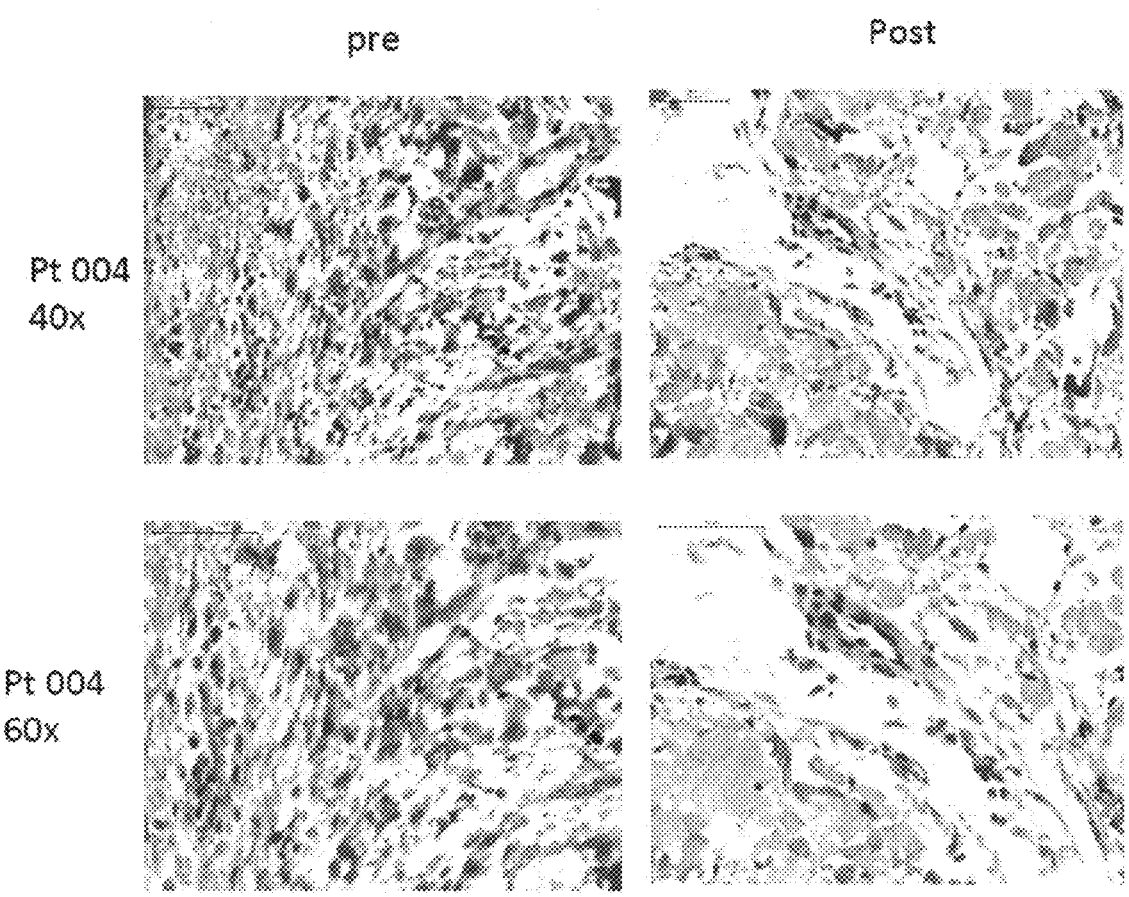
FIG. 30. Immunohistochemistry of CD4+ cells in a representative patient (Patient 004). Brown staining indicates the presence of CD11b+ cells at the start of treatment with ketoprofen ("1-LY"). CD11b+ cells are significantly reduced by the 4$^{th}$ clinical follow up visit ("4-LY").
Figure 31:
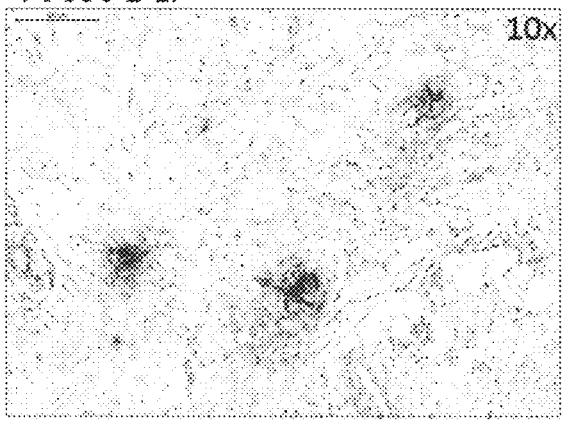
FIG. 31. Immunohistochemistry of CD4+ cells in a representative patient (Patient 030). Blue staining indicates the presence of CD11b+ cells at the start of treatment with ketoprofen ("1-LY"). CD11b+ cells are significantly reduced by the 4$^{th}$ clinical follow up visit ("4-LY").
Figure 31:
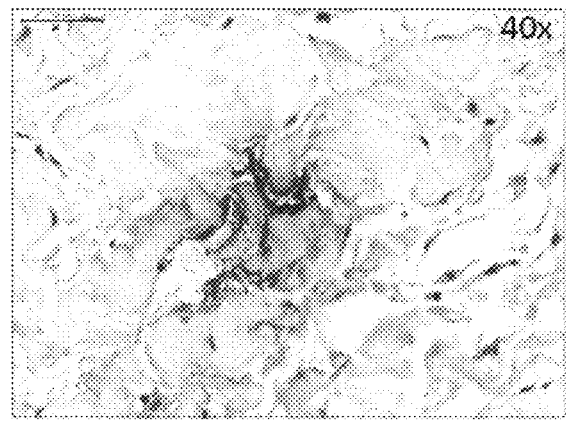
Figure 31:
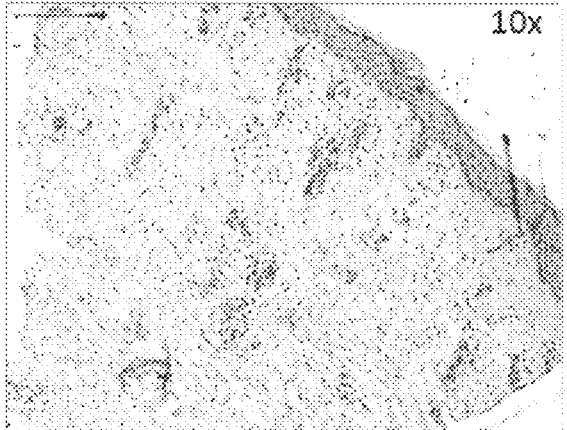
Figure 31:
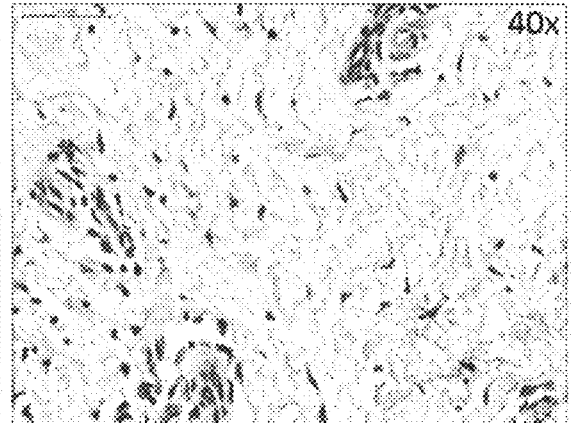
Figure 32:
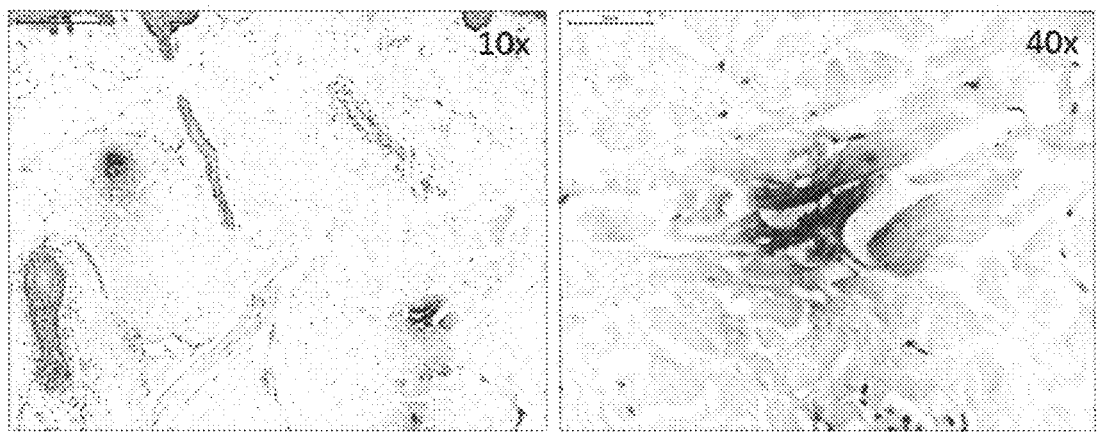
FIG. 32. Immunohistochemistry of CD4+ cells in a representative patient (Patient 033). Blue staining indicates the presence of CD11b+ cells at the start of treatment with ketoprofen ("1-LY"). CD11b+ cells are significantly reduced by the 4$^{th}$ clinical follow up visit ("4-LY").
Figure 32:
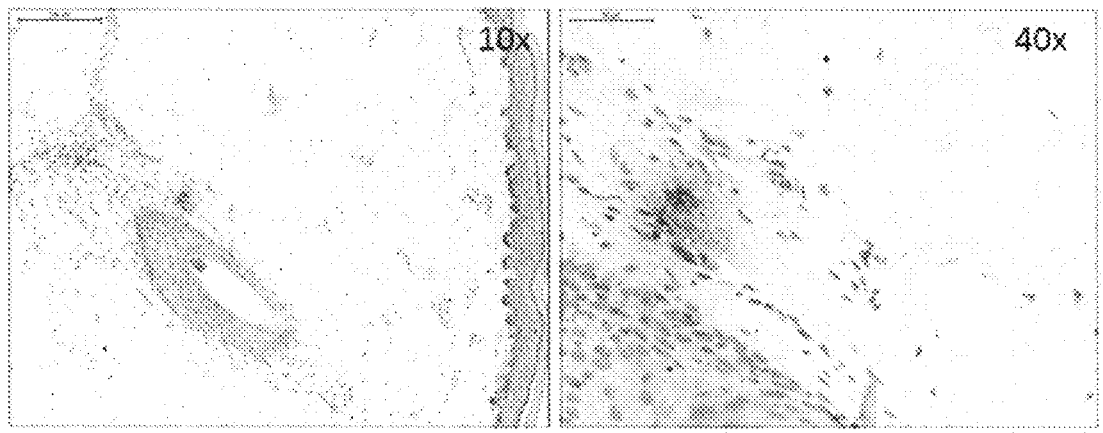

To determine the cellular basis for the lymphedema pathology, lymphedemous tissue was analyzed for the aberrant presence of immune cells. Matched human punch biopsies showed a 2-fold increase in CD11B+ cells (FIGS. 26-28) and a 3-fold increase in CD4+ helper T cells (FIG. 29-32) in the affected tissue as compared to normal tissue (p<0.05), and the clinical lymphedema grade correlated with the extent of CD11B+ and CD4+ infiltrate (Spearman r=0.6332, p<0.016). IL-13 localization revealed a 2-fold increase in the number of IL-13-positive mononuclear cells in lymphedemous samples compared to normal tissue (p<0.03). Serum analysis revealed a decrease in both CD30 and IgE levels from pre to post treatment with ketoprofen: CD30 amounts decreased an average of 13% after treatment (p=0.0587) and IgE amount decreased an average of −22% (p=0.007). These findings are consistent with decreased Th2 differentiation in lymphedemous tissue.

Strikingly, CD11B+ and CD4+ cells are absent from affected tissue after treatment with ketoprofen (FIGS. 26-32). Thus, loss of fluid following treatment with ketoprofen is accompanied by a partial to complete normalization of the tissue architecture with regard to inflammatory cell infiltrates.

Following the clinical trial, 100% of participants elected to continue off-label treatment of their lymphedema with ketoprofen, 9% discontinued chronic use of compression garments, 7% described relief from pain, 7% noted that the affected limb feels lighter, 2% describe the affected limb as normal in size, and 2% noted that the compression garment is loose. It was noted that in those patients that did not experience a decrease in volume, a restoration in the tissue architecture was still observed.

Example 6

Ketoprofen Derivatives with Improved Bioavailability

Ketoprofen is one of the commercially available 2-arylpropionic acids non-steroidal anti-inflammatory drugs (NSAIDs). Administration via transdermal routes are limited by its poor aqueous solubility and low permeability. To improve solubility and permeability, ester modifications were made on ketoprofen to insert methyl, ethyl or isopropyl side groups on the molecule.

Figure 33:
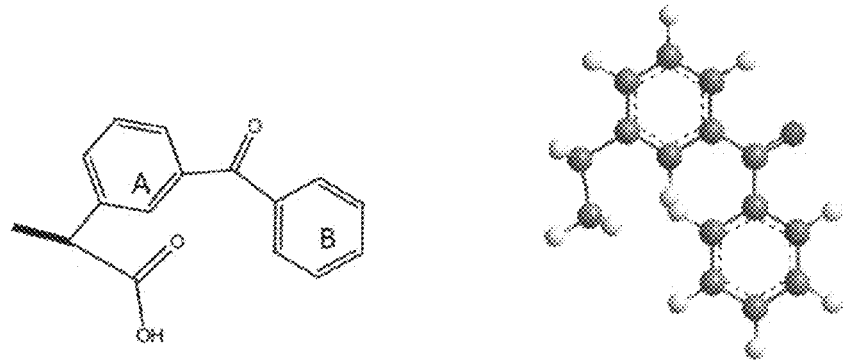
FIG. 33. Ketoprofen chemistry. (A) Chemical formula of ketoprofen. (B) Ester modification to improve bioavailability. Y axis is the cumulative permeation of microgram/cm$^2$/Ketoprofen Ester delivered through the Stratum Corneum layer of human cadaver skin. x axis=time in hours. Closed triangles: Methyl ester. Open circles: ethyl ester. Open squares: isopropyl ester. x axis=time in hours.
Figure 33:
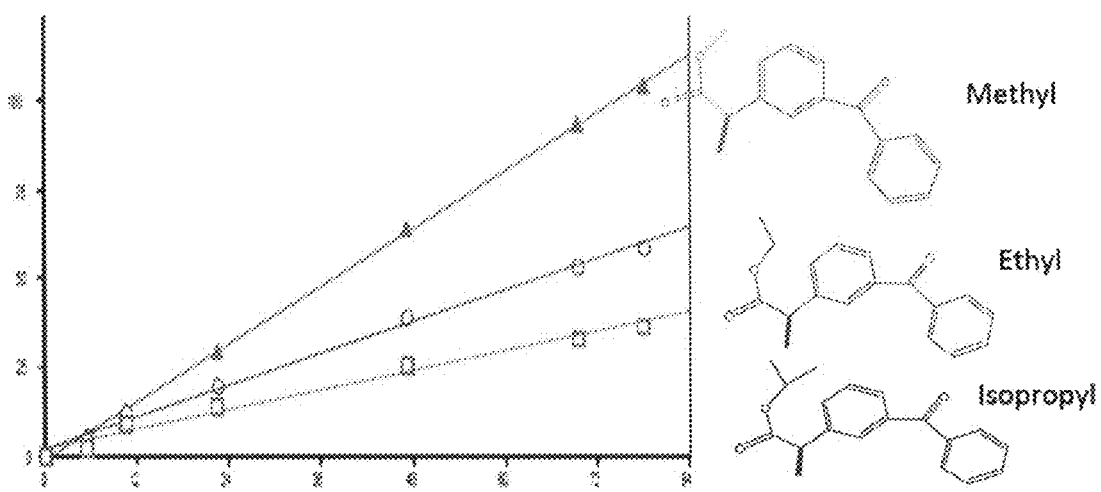

Ketoprofen (molecular weight of 254.29 and a Log $K_{ow}$ of 3.00), ketoprofen methyl ester (molecular weight of 268.31 and a Log $K_{ow}$ of 3.65), ketoprofen ethyl ester (molecular weight of 282.34 and a Log $K_{ow}$ of 4.14) and ketoprofen isopropyl ester (molecular weight of 296.37 and a Log $K_{ow}$ of 4.56) were prepared and assayed for their ability to permeate the stratum corneum of human cadaver skin. As illustrated in FIG. 33, derivatizations improved the ability of ketoprofen to penetrate the skin, with methyl derivatization providing for the most penetration and hence drug delivery.

Ketoprofen was formulated as a 5% ketoprofen cream by complexing 250 mg of Ketoprofen with 350 mg of 2-Hydroxpropyl-β-cyclodextrin. This complex was well dispersed in a cream base containing lipids, cetyl alcohol and tween surfactants.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

What is claimed is:

1. A method for the treatment of acquired lymphedema in a subject, the method comprising: administering ketoprofen or a derivative thereof to a subject having acquired lymphedema in an amount effective to reduce volume of the lymphedema in said subject.

2. The method according to claim 1, wherein said administering comprises topical administration.

3. The method according to claim 1, wherein said method further comprises the step of administering an effective amount of a diuretic agent.

4. The method according to claim 1, wherein said ketoprofen derivative is a derivative having a methyl ester, ethyl ester or isopropyl ester side group.

5. The method according to claim 1, wherein the method further comprises measuring the lymphedema in the subject before and after said administering.

* * * * *

SEQUENCE LISTING

```
<160> NUMBER OF SEQ ID NOS: 15

<210> SEQ ID NO 1
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 1
gacttcaaga aaatggtcac tactgagt                                        28

<210> SEQ ID NO 2
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 2
tgtccaattc tctgaacaag ttttcga                                         27
```

```
<210> SEQ ID NO 3
<211> LENGTH: 18
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 1
<223> OTHER INFORMATION: 6-carboxyfluorescein (FAM)
<220> FEATURE:
<221> NAME/KEY: misc_feature
<222> LOCATION: 18
<223> OTHER INFORMATION: non-fluorescent quencher (NFQ)

<400> SEQUENCE: 3
tcagtttgtg cagaatat                                                18

<210> SEQ ID NO 4
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 4
agacaaatgg tggaagcaca gtt                                          23

<210> SEQ ID NO 5
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 5
ccaggtcctc catgatgtca tttat                                        25

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 1
<223> OTHER INFORMATION: 6-carboxyfluorescein (FAM)
<220> FEATURE:
<221> NAME/KEY: misc_feature
<222> LOCATION: 24
<223> OTHER INFORMATION: non-fluorescent quencher (NFQ)

<400> SEQUENCE: 6
ttctctttct tcataaaggt tgcc                                         24

<210> SEQ ID NO 7
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 7
agggcgaaga caagtactac ctt                                          23

<210> SEQ ID NO 8
<211> LENGTH: 19
<212> TYPE: DNA
```

```
<213> ORGANISM: Artificial Sequence
<220> FEATURE:
<223> OTHER INFORMATION: synthetic oligonucleotide

<400> SEQUENCE: 8
caccaccacc tcagtgaca                                                19

<210> SEQ ID NO 9
<211> LENGTH: 15
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 1
<223> OTHER INFORMATION: 6-carboxyfluorescein (FAM)
<220> FEATURE:
<221> NAME/KEY: misc_feature
<222> LOCATION: 15
<223> OTHER INFORMATION: non-fluorescent quencher (NFQ)

<400> SEQUENCE: 9
ccaccgtgac caccc                                                    15

<210> SEQ ID NO 10
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 10
tcccgtttcc atctctctca aga                                           23

<210> SEQ ID NO 11
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 11
gggtaccacg aggacatcag                                               20

<210> SEQ ID NO 12
<211> LENGTH: 17
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 1
<223> OTHER INFORMATION: 6-carboxyfluorescein (FAM)
<220> FEATURE:
<221> NAME/KEY: misc_feature
<222> LOCATION: 17
<223> OTHER INFORMATION: non-fluorescent quencher (NFQ)

<400> SEQUENCE: 12
tccctctatg gaactcc                                                  17

<210> SEQ ID NO 13
<211> LENGTH: 19
<212> TYPE: DNA
<213> ORGANISM: Artificial Sequence
<220> FEATURE:
<223> OTHER INFORMATION: synthetic oligonucleotide
```

-continued

```
<400> SEQUENCE: 13
cccaaggcag caacttcag                                           19

<210> SEQ ID NO 14
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 14
cctggaggta ggtagccata ctg                                      23

<210> SEQ ID NO 15
<211> LENGTH: 16
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: 1
<223> OTHER INFORMATION: 6-carboxyfluorescein (FAM)
<220> FEATURE:
<221> NAME/KEY: misc_feature
<222> LOCATION: 16
<223> OTHER INFORMATION: non-fluorescent quencher (NFQ)

<400> SEQUENCE: 15
cccgaagcct ggctgc                                              16
```